US009988346B2

(12) United States Patent
Weerasooriya et al.

(10) Patent No.: US 9,988,346 B2
(45) Date of Patent: Jun. 5, 2018

(54) LARGE HYDROPHOBE SURFACTANTS

(75) Inventors: Upali P. Weerasooriya, Austin, TX (US); Gary A. Pope, Cedar Park, TX (US); Peter Radford, Shawnee, KS (US); Howard Stevenson, Kansas City, KS (US)

(73) Assignees: Board of Regents, The University of Texas System, Austin, TX (US); Harcros Chemicals, Inc., Kansas City, KS (US)

(*) Notice: Subject to any disclaimer, the term of this patent is extended or adjusted under 35 U.S.C. 154(b) by 727 days.

(21) Appl. No.: 14/237,805

(22) PCT Filed: Apr. 17, 2012

(86) PCT No.: PCT/US2012/033972
§ 371 (c)(1),
(2), (4) Date: Nov. 24, 2015

(87) PCT Pub. No.: WO2012/154376
PCT Pub. Date: Nov. 15, 2012

(65) Prior Publication Data
US 2017/0334840 A1    Nov. 23, 2017

Related U.S. Application Data

(60) Provisional application No. 61/478,434, filed on Apr. 22, 2011.

(51) Int. Cl.
*C07C 309/10* (2006.01)
*C07C 305/10* (2006.01)
(Continued)

(52) U.S. Cl.
CPC .......... *C07C 309/10* (2013.01); *C07C 59/125* (2013.01); *C07C 305/10* (2013.01); *C09K 8/584* (2013.01)

(58) Field of Classification Search
CPC ... C07C 309/10; C07C 305/10; C07C 59/325; C07C 8/584; C09K 8/584
See application file for complete search history.

(56) References Cited

U.S. PATENT DOCUMENTS 4,446,079 A * 5/1984 Hoskin ............... B01F 17/0057
507/255
4,515,701 A   5/1985 Hoskin
(Continued)

FOREIGN PATENT DOCUMENTS

| WO | 2009088778 A1 | 7/2009 |
| WO | 2011037975 A2 | 3/2011 |
| WO | 2012145274 A2 | 11/2012 |

OTHER PUBLICATIONS

International Search Report and Written Opinion of the International Searching Authority for PCT/US2012/033972, dated Jan. 24, 2013.
(Continued)

*Primary Examiner* — James Goloboy
(74) *Attorney, Agent, or Firm* — Muenier Carlin & Curfman LLC

(57) ABSTRACT

Provided herein are inter alia novel compositions and methods having application in the field of enhanced oil recovery. In particular, the large hydrophobe compounds and mixtures thereof presented herein can be used, inter alia, for the recovery of a large range of crude oil compositions from challenging reservoirs.

30 Claims, 13 Drawing Sheets

(51) Int. Cl.
*C07C 59/125* (2006.01)
*C09K 8/584* (2006.01)

(56) References Cited

U.S. PATENT DOCUMENTS

| | | |
|---|---|---|
| 4,738,789 A | 4/1988 | Jones |
| 5,523,470 A | 6/1996 | Karlsson et al. |
| 7,119,125 B1 | 10/2006 | O'Lenick et al. |
| 2009/0264598 A1* | 10/2009 | Bittner ............... B01F 17/0021 525/231 |

OTHER PUBLICATIONS

European Search Report and Opinion for related European Application No. 12781995, dated Aug. 6, 2015.

* cited by examiner $\gamma = 0.3/40^2 = 1.87 \times 10^{-4}$ dynes/cm

LARGE HYDROPHOBE SURFACTANTS

CROSS-REFERENCES TO RELATED APPLICATIONS

This application is a national phase application of PCT Application No. PCT/US2012/033972 filed Apr. 17, 2012, which claims the benefit of U.S. Provisional Application No. 61/478,434 filed Apr. 22, 2011, which is hereby incorporated in its entirety and for all purposes.

BACKGROUND OF THE INVENTION

Enhanced Oil Recovery (abbreviated EOR) refers to techniques for increasing the amount of unrefined petroleum, or crude oil, that may be extracted from an oil reservoir (e.g. an oil field). Using EOR, 40-60% of the reservoir's original oil can typically be extracted compared with only 20-40% using primary and secondary recovery (e.g. by water injection or natural gas injection). Enhanced oil recovery may also be referred to as improved oil recovery or tertiary recovery (as opposed to primary and secondary recovery).

Enhanced oil recovery may be achieved by a variety of methods including miscible gas injection (which includes carbon dioxide flooding), chemical injection (which includes polymer flooding, alkaline flooding and surfactant flooding), microbial injection, or thermal recovery (which includes cyclic steam, steam flooding, and fire flooding). The injection of various chemicals, usually as dilute aqueous solutions, has been used to improve oil recovery. Injection of alkaline or caustic solutions into reservoirs with oil that has organic acids naturally occurring in the oil will result in the production of soap that may lower the interfacial tension enough to increase production. Injection of a dilute solution of a water soluble polymer to increase the viscosity of the injected water can increase the amount of oil recovered in some formations. Dilute solutions of surfactants such as petroleum sulfonates may be injected to lower the interfacial tension or capillary pressure that impedes oil droplets from moving through a reservoir. Special formulations of oil, water and surfactant microemulsions, have also proven useful. Application of these methods is usually limited by the cost of the chemicals and their adsorption and loss onto the rock of the oil containing formation.

Some unrefined petroleum contains carboxylic acids having, for example, $C_{11}$ to $C_{20}$ alkyl chains, including napthenic acid mixtures. The recovery of such "reactive" oils may be performed using alkali (e.g. NaOH or $Na_2CO_3$) in a surfactant composition. The alkali reacts with the acid in the reactive oil to form soap. These soaps serve as an additional source of surfactants enabling the use of much lower level of surfactants initially added to effect enhanced oil recovery (EOR). However, when the available water supply is hard, the added alkali causes precipitation of cations, such as $Ca^{+2}$ or $Mg^{+2}$. In order to prevent such precipitation an expensive chelant such as EDTA may be required in the surfactant composition. Alternatively, expensive water softening processes may be used.

Therefore, there is a need in the art for cost effective methods for enhanced oil recovery using chemical injection. Provided herein are methods and compositions addressing these and other needs in the art.

BRIEF SUMMARY OF THE INVENTION

Figure 1:
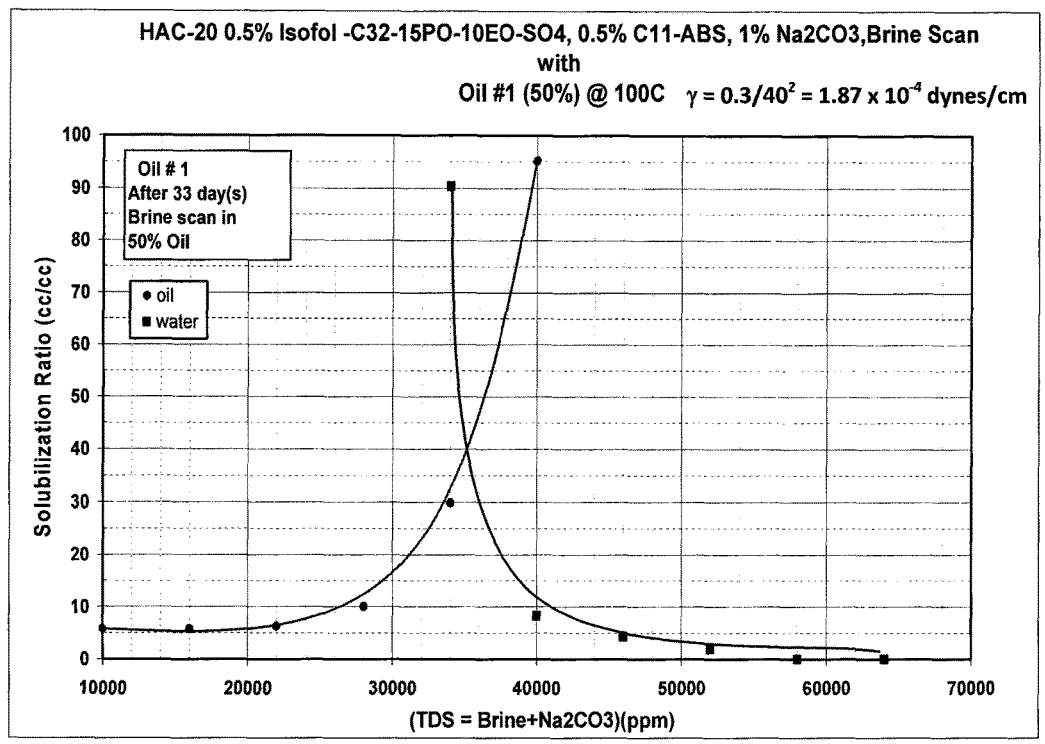
FIG. 1. Phase behavior plot for a study with HAC-20 0.5% Isofol (Guerbet)-C32-15PO-10EO-SO4, 0.5% C11-ABS (Alkylbenzene sulfonate), 1% $Na_2CO_3$, Brine Scan with Oil #1 (50%) at 100° C. (a control study).

In a first aspect, the present invention provides a compound having the formula:

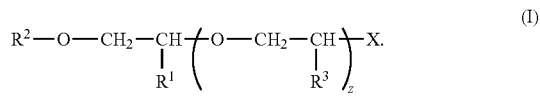

$$R^2-O-CH_2-CH(R^1)-(O-CH_2-CH(R^3))_z-X. \quad (I)$$

In formula (I), $R^1$ is $R^{10}$-substituted or unsubstituted $C_8$-$C_{50}$ alkyl, $R^4$-substituted or unsubstituted heteroalkyl, $R^4$-substituted or unsubstituted aryl or $R^4$-substituted or unsubstituted cycloalkyl. $R^4$ is $R^5$-substituted or unsubstituted $C_1$-$C_{50}$ alkyl, $R^5$-substituted or unsubstituted heteroalkyl, $R^5$-substituted or unsubstituted aryl or $R^5$-substituted or unsubstituted cycloalkyl. $R^5$ is $R^6$-substituted or unsubstituted $C_1$-$C_{50}$ alkyl, $R^6$-substituted or unsubstituted heteroalkyl, $R^6$-substituted or unsubstituted aryl or $R^6$-substituted or unsubstituted cycloalkyl. $R^6$ is $R^7$-substituted or unsubstituted $C_1$-$C_{50}$ alkyl, $R^7$-substituted or unsubstituted heteroalkyl, $R^7$-substituted or unsubstituted aryl or $R^7$-substituted or unsubstituted cycloalkyl. $R^7$ is $R^8$-substituted or unsubstituted $C_1$-$C_{50}$ alkyl, $R^8$-substituted or unsubstituted heteroalkyl, $R^8$-substituted or unsubstituted heteroalkyl, $R^8$-substituted or unsubstituted aryl or $R^8$-substituted or unsubstituted cycloalkyl. $R^8$ is $R^9$-substituted or unsubstituted $C_1$-$C_{50}$ alkyl, $R^9$-substituted or unsubstituted heteroalkyl, $R^9$-substituted or unsubstituted aryl or $R^9$-substituted or unsubstituted cycloalkyl. $R^9$ is unsubstituted $C_1$-$C_{50}$ alkyl, unsubstituted heteroalkyl, unsubstituted aryl or unsubstituted cycloalkyl. $R^{10}$ is unsubstituted hetreroalkyl, unsubstituted aryl or unsubstituted cycloalkyl. $R^2$ is $R^{10a}$-substituted or unsubstituted $C_8$-$C_{50}$ alkyl, $R^{4a}$-substituted or unsubstituted heteroalkyl, $R^{4a}$-substituted or unsubstituted aryl or $R^{4a}$-substituted or unsubstituted cycloalkyl. $R^{4a}$ is $R^{5a}$-substituted or unsubstituted $C_1$-$C_{50}$ alkyl, $R^{5a}$-substituted or unsubstituted heteroalkyl, $R^{5a}$-substituted or unsubstituted aryl or $R^{5a}$-substituted or unsubstituted cycloalkyl. $R^{5a}$ is $R^{6a}$-substituted or unsubstituted $C_1$-$C_{50}$ alkyl, $R^{6a}$-substituted or unsubstituted heteroalkyl, $R^{6a}$-substituted or unsubstituted aryl or $R^{6a}$-substituted or unsubstituted cycloalkyl. $R^{6a}$ is $R^{7a}$-substituted or unsubstituted $C_1$-$C_{50}$ alkyl, $R^{7a}$-substituted or unsubstituted heteroalkyl, $R^{7a}$-substituted or unsubstituted aryl or $R^{7a}$-substituted or unsubstituted cycloalkyl. $R^{7a}$ is $R^{8a}$-substituted or unsubstituted $C_1$-$C_{50}$ alkyl, $R^{8a}$-substituted or unsubstituted heteroalkyl, $R^{8a}$-substituted or unsubstituted heteroalkyl, $R^{8a}$-substituted or unsubstituted aryl or $R^{8a}$-substituted or unsubstituted cycloalkyl. $R^{8a}$ is $R^{9a}$-substituted or unsubstituted $C_1$-$C_{50}$ alkyl, $R^{9a}$-substituted or unsubstituted heteroalkyl, $R^{9a}$-substituted or unsubstituted aryl or $R^{9a}$-substituted or unsubstituted cycloalkyl. $R^{9a}$ is unsubstituted $C_1$-$C_{50}$ alkyl, unsubstituted heteroalkyl, unsubstituted aryl or unsubstituted cycloalkyl. $R^{10a}$ is unsubstituted heteroalkyl, unsubstituted aryl or unsubstituted cycloalkyl. $R^3$ is independently hydrogen or unsubstituted $C_1$-$C_6$ alkyl. The symbol z is an integer from 2 to 100. X is

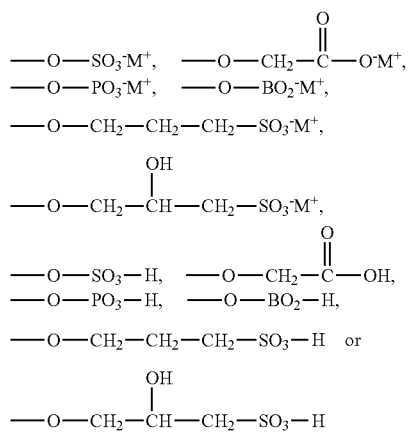

and $M^+$ is a monovalent, divalent or trivalent cation.

In another aspect, an aqueous composition is provided including a co-surfactant and a compound described herein (e.g. a compound of formula (I), (II), (III), (IV), or (V)).

In another aspect, an emulsion composition is provided including an unrefined petroleum phase and an aqueous. The aqueous phase includes the compound described herein (e.g. a compound of formula (I), (II), (III), (IV), or (V)).

In another aspect, a method of displacing a hydrocarbon material in contact with a solid material is provided. The method includes contacting a hydrocarbon material with the compound described herein (e.g. a compound of formula (I), (II), (III), (IV), or (V)), wherein the hydrocarbon material is in contact with a solid material. The hydrocarbon material is allowed to separate from the solid material thereby displacing the hydrocarbon material in contact with the solid material.

In another aspect, a method of converting an unrefined petroleum acid into a surfactant is provided. The method includes contacting a petroleum material with an aqueous composition thereby forming an emulsion in contact with the petroleum material, wherein the aqueous composition includes the compound described herein (e.g. a compound of formula (I), (II), (III), (IV), or (V)) and a co-surfactant. A unrefined petroleum acid within said unrefined petroleum material is allowed to enter into the emulsion, thereby converting the unrefined petroleum acid into a surfactant.

In another aspect, a method of making a compound described herein (e.g. a compound of formula (I), (II), (III), (IV), or (V)) is provided. The method includes contacting an epoxide compound with an alcohol thereby forming an epoxide-alcohol mixture. The temperature of the epoxide-alcohol mixture is increased thereby forming an epoxide-alcohol adduct. The epoxide-alcohol adduct is contacted with a $C_1$-$C_4$ alkoxide thereby forming an alkoxylated hydrophobe and the alkoxylated hydrophobe is contacted with one or more anionic functional groups thereby forming the compound.

DETAILED DESCRIPTION OF THE INVENTION

I. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl". An alkoxy is an alkyl attached to the remainder of the molecule via an oxygen linker (—O—).

The term "alkylene" by itself or as part of another substituent means a divalent radical derived from an alkyl, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si and S, and wherein the nitrogen and sulfur atoms may optionally be oxidized, and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The term "aryl" means, unless otherwise stated, a polyunsaturated, aromatic, hydrocarbon substituent which can be a single ring or multiple rings (preferably from 1 to 3 rings) which are fused together (i.e. a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e. multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent means a divalent radical derived from an aryl and heteroaryl, respectively.

The term "oxo" as used herein means an oxygen that is double bonded to a carbon atom.

Where a substituent of a compound provided herein is "R-substituted" (e.g. $R^7$-substituted), it is meant that the substituent is substituted with one or more of the named R groups (e.g. $R^7$) as appropriate. In some embodiments, the substituent is substituted with only one of the named R groups.

The symbol "〜" denotes the point of attachment of a chemical moiety to the remainder of a molecule or chemical formula.

Each R-group as provided in the formulae provided herein can appear more than once. Where an R-group appears more than once each R group can be optionally different.

The term "contacting" as used herein, refers to materials or compounds being sufficiently close in proximity to react or interact. For example, in methods of contacting a hydrocarbon material bearing formation and/or a well bore, the term "contacting" includes placing an aqueous composition (e. g. chemical, surfactant or polymer) within a hydrocarbon material bearing formation using any suitable manner known in the art (e.g., pumping, injecting, pouring, releasing, displacing, spotting or circulating the chemical into a well, well bore or hydrocarbon bearing formation).

The terms "unrefined petroleum" and "crude oil" are used interchangeably and in keeping with the plain ordinary usage of those terms. "Unrefined petroleum" and "crude oil" may be found in a variety of petroleum reservoirs (also referred to herein as a "reservoir," "oil field deposit" "deposit" and the like) and in a variety of forms including oleaginous materials, oil shales (i.e. organic-rich fine-grained sedimentary rock), tar sands, light oil deposits, heavy oil deposits, and the like. "Crude oils" or "unrefined petroleums" generally refer to a mixture of naturally occurring hydrocarbons that may be refined into diesel, gasoline, heating oil, jet fuel, kerosene, and other products called fuels or petrochemicals. Crude oils or unrefined petroleums are named according to their contents and origins, and are classified according to their per unit weight (specific gravity). Heavier crudes generally yield more heat upon burning, but have lower gravity as defined by the American Petroleum Institute (API) and market price in comparison to light (or sweet) crude oils. Crude oil may also be characterized by its Equivalent Alkane Carbon Number (EACN).

Crude oils vary widely in appearance and viscosity from field to field. They range in color, odor, and in the properties they contain. While all crude oils are mostly hydrocarbons, the differences in properties, especially the variation in molecular structure, determine whether a crude oil is more or less easy to produce, pipeline, and refine. The variations may even influence its suitability for certain products and the quality of those products. Crude oils are roughly classified into three groups, according to the nature of the hydrocarbons they contain. (i) Paraffin based crude oils contain higher molecular weight paraffins, which are solid at room temperature, but little or no asphaltic (bituminous) matter. They can produce high-grade lubricating oils. (ii) Asphaltene based crude oils contain large proportions of asphaltic matter, and little or no paraffin. Some are predominantly naphthenes and so yield lubricating oils that are sensitive to temperature changes than the paraffin-based crudes. (iii) Mixed based crude oils contain both paraffin and naphthenes, as well as aromatic hydrocarbons. Most crude oils fit this latter category.

"Reactive" crude oil as referred to herein is crude oil containing natural organic acidic components. More terms used interchangeably for oil throughout this disclosure are hydrocarbon material or petroleum material. An "oil bank" or "oil cut" as referred to herein, is the crude oil that does not contain the injected chemicals and is pushed by the injected fluid during an enhanced oil recovery process.

The term "polymer" refers to a molecule having a structure that essentially includes the multiple repetitions of units derived, actually or conceptually, from molecules of low relative molecular mass. In some embodiments, the polymer is an oligomer.

The term "bonded" refers to having at least one of covalent bonding, hydrogen bonding, ionic bonding, Van Der Waals interactions, pi interactions, London forces or electrostatic interactions.

The term "productivity" as applied to a petroleum or oil well refers to the capacity of a well to produce hydrocarbons (e.g. unrefined petroleum); that is, the ratio of the hydrocarbon flow rate to the pressure drop, where the pressure drop is the difference between the average reservoir pressure and the flowing bottom hole well pressure (i.e., flow per unit of driving force).

The term "oil solubilization ratio" is defined as the volume of oil solubilized divided by the volume of surfactant in microemulsion. All the surfactant is presumed to be in the microemulsion phase. The oil solubilization ratio is applied for Winsor type I and type III behavior. The volume of oil solubilized is found by reading the change between initial aqueous level and excess oil (top) interface level. The oil solubilization ratio is calculated as follows:

$$\sigma_o = \frac{V_o}{V_s},$$

wherein
$\sigma_o$=oil solubilization ratio;
$V_o$=volume of oil solubilized;
$V_s$=volume of surfactant.

The term "water solubilization ratio" is defined as the volume of water solubilized divided by the volume of surfactant in microemulsion. All the surfactant is presumed to be in the microemulsion phase. The water solubilization ratio is applied for Winsor type III and type II behavior. The volume of water solubilized is found by reading the change between initial aqueous level and excess water (bottom) interface level. The water solubilization parameter is calculated as follows:

$$\sigma_w = \frac{V_w}{V_s},$$

wherein
$\sigma_w$=water solubilization ratio;
$V_w$=volume of water solubilized.

The optimum solubilization ratio occurs where the oil and water solubilization ratios are equal. The coarse nature of phase behavior screening often does not include a data point at optimum, so the solubilization ratio curves are drawn for the oil and water solubilization ratio data and the intersection of these two curves is defined as the optimum. The following is true for the optimum solubilization ratio:
$\sigma_o = \sigma_w = \sigma^*$;
$\sigma^*$=optimum solubilization ratio.

The term "solubility" or "solubilization" in general refers to the property of a solute, which can be a solid, liquid or gas, to dissolve in a solid, liquid or gaseous solvent thereby forming a homogenous solution of the solute in the solvent. Solubility occurs under dynamic equilibrium, which means that solubility results from the simultaneous and opposing processes of dissolution and phase joining (e.g. precipitation of solids). The solubility equilibrium occurs when the two processes proceed at a constant rate. The solubility of a given solute in a given solvent typically depends on temperature. For many solids dissolved in liquid water, the solubility increases with temperature. In liquid water at high temperatures, the solubility of ionic solutes tends to decrease due to the change of properties and structure of liquid water. In more particular, solubility and solubilization as referred to herein is the property of oil to dissolve in water and vice versa.

"Viscosity" refers to a fluid's internal resistance to flow or being deformed by shear or tensile stress. In other words, viscosity may be defined as thickness or internal friction of a liquid. Thus, water is "thin", having a lower viscosity, while oil is "thick", having a higher viscosity. More generally, the less viscous a fluid is, the greater its ease of fluidity.

The term "salinity" as used herein, refers to concentration of salt dissolved in a aqueous phases. Examples for such salts are without limitation, sodium chloride, magnesium and calcium sulfates, and bicarbonates. In more particular, the term salinity as it pertains to the present invention refers to the concentration of salts in brine and surfactant solutions.

The term "aqueous solution or aqueous formulation" refers to a solution in which the solvent is water. The term "emulsion, emulsion solution or emulsion formulation" refers to a mixture of two or more liquids which are normally immiscible. A non-limiting example for an emulsion is a mixtures of oil and water.

II. Compositions

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not limit the scope of the invention.

Provided herein, inter alia, are large hydrophobe compounds and methods of using the same for a variety of applications including enhanced oil recovery. The compounds provided herein may be used with broad oil concentrations, at a wide range of salinities, at high reservoir temperatures and over a broad pH range. The large hydrophobe compounds of the present invention represent a cost effective alternative to commonly used EOR surfactants derived from Guerbet alcohols. The compounds described herein may also significantly improve the effectiveness of co-surfactant sulfonate compounds such as ABS or IOS to a surprising degree.

Where sulfonate compounds are combined with the compounds provided herein, the combination may be more stable and effective when compared to the stability and effectiveness of the sulfonate compounds in the absence of the compounds provided herein (e.g. a compound of formula (I), (II), (III), (IV), or (V)).

In a first aspect, the present invention provides a compound having the formula:

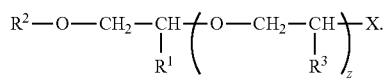

(I)

In formula (I), $R^1$ is $R^{10}$-substituted or unsubstituted $C_8$-$C_{50}$ alkyl, $R^4$-substituted or unsubstituted heteroalkyl, $R^4$-substituted or unsubstituted aryl or $R^4$-substituted or unsubstituted cycloalkyl. $R^4$ is $R^5$-substituted or unsubstituted $C_1$-$C_{50}$ alkyl, $R^5$-substituted or unsubstituted heteroalkyl, $R^5$-substituted or unsubstituted aryl or $R^5$-substituted or unsubstituted cycloalkyl. $R^5$ is $R^6$-substituted or unsubstituted $C_1$-$C_{50}$ alkyl, $R^6$-substituted or unsubstituted heteroalkyl, $R^6$-substituted or unsubstituted aryl or $R^6$-substituted or unsubstituted cycloalkyl. $R^6$ is $R^7$-substituted or unsubstituted $C_1$-$C_{50}$ alkyl, $R^7$-substituted or unsubstituted heteroalkyl, $R^7$-substituted or unsubstituted aryl or $R^7$-substituted or unsubstituted cycloalkyl. $R^7$ is $R^8$-substituted or unsubstituted $C_1$-$C_{50}$ alkyl, $R^8$-substituted or unsubstituted heteroalkyl, $R^8$-substituted or unsubstituted aryl or $R^8$-substituted or unsubstituted cycloalkyl. $R^8$ is $R^9$-substituted or unsubstituted $C_1$-$C_{50}$ alkyl, $R^9$-substituted or unsubstituted heteroalkyl, $R^9$-substituted or unsubstituted aryl or $R^9$-substituted or unsubstituted cycloalkyl. $R^9$ is unsubstituted $C_1$-$C_{50}$ alkyl, unsubstituted heteroalkyl, unsubstituted aryl or unsubstituted cycloalkyl. $R^{10}$ is unsubstituted hetreroalkyl, unsubstituted aryl or unsubstituted cycloalkyl. $R^2$ is $R^{10a}$-substituted or unsubstituted $C_8$-$C_{50}$ alkyl, $R^{4a}$-substituted or unsubstituted heteroalkyl, $R^{4a}$-substituted or unsubstituted aryl or $R^{4a}$-substituted or unsubstituted cycloalkyl. $R^{4a}$ is $R^{5a}$-substituted or unsubstituted $C_1$-$C_{50}$ alkyl, $R^{5a}$-substituted or unsubstituted heteroalkyl, $R^{5a}$-substituted or unsubstituted aryl or $R^{5a}$-substituted or unsubstituted cycloalkyl. $R^{5a}$ is $R^{6a}$-substituted or unsubstituted $C_1$-$C_{50}$ alkyl, $R^{6a}$-substituted or unsubstituted heteroalkyl, $R^{6a}$-substituted or unsubstituted aryl or $R^{6a}$-substituted or unsubstituted cycloalkyl. $R^{6a}$ is $R^{7a}$-substituted or unsubstituted $C_1$-$C_{50}$ alkyl, $R^{7a}$-substituted or unsubstituted heteroalkyl, $R^{7a}$-substituted or unsubstituted aryl or $R^{7a}$-substituted or unsubstituted cycloalkyl. $R^{7a}$ is $R^{8a}$-substituted or unsubstituted $C_1$-$C_{50}$ alkyl, $R^{8a}$-substituted or unsubstituted heteroalkyl, $R^{8a}$-substituted or unsubstituted heteroalkyl, $R^{8a}$-substituted or unsubstituted aryl or $R^{8a}$-substituted or unsubstituted cycloalkyl. $R^{8a}$ is $R^{9a}$-substituted or unsubstituted $C_1$-$C_{50}$ alkyl, $R^{9a}$-substituted or unsubstituted heteroalkyl, $R^{9a}$-substituted or unsubstituted aryl or $R^{9a}$-substituted or unsubstituted cycloalkyl. $R^{9a}$ is unsubstituted $C_1$-$C_{50}$ alkyl, unsubstituted heteroalkyl, unsubstituted aryl or unsubstituted cycloalkyl. $R^{10a}$ is unsubstituted hetreroalkyl, unsubstituted aryl or unsubstituted cycloalkyl. Where $R^4$-$R^{10}$ or $R^{4a}$-$R^{10a}$ are each alkyls, the total number of carbons does not exceed 150. $R^3$ is independently hydrogen or unsubstituted $C_1$-$C_6$ alkyl. The symbol z is an integer from 2 to 100. X is

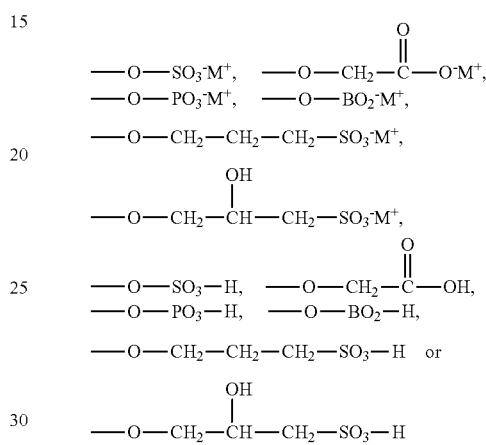

and $M^+$ is a monovalent, divalent or trivalent cation. In formula (I) each of $R^3$, $R^4$, $R^5$, $R^6$, $R^7$, $R^8$, $R^9$, and $R^{10}$, and $R^{4a}$, $R^{5a}$, $R^{6a}$, $R^{7a}$, $R^{8a}$, $R^{9a}$, and $R^{10a}$, can appear more than once and can be optionally different. For example, in some embodiments where z is 4, $R^3$ appears four times and can be optionally different. In other embodiments, where z is 6, $R^3$ appears six times and can be optionally different. X is a functional group as described above or an acid or salt thereof and H is hydrogen.

In some embodiments, the symbol z is an integer from 5 to 100. In other embodiments, the symbol z is an integer from 10 to 100. In other embodiments, the symbol z is an integer from 15 to 100. In other embodiments, the symbol z is an integer from 20 to 100. In other embodiments, the symbol z is an integer from 25 to 100. In other embodiments, the symbol z is an integer from 30 to 100. In other embodiments, the symbol z is an integer from 35 to 100. In other embodiments, the symbol z is an integer from 40 to 100. In other embodiments, the symbol z is an integer from 45 to 100. In other embodiments, the symbol z is an integer from 50 to 100. In other embodiments, the symbol z is an integer from 55 to 100. In other embodiments, the symbol z is an integer from 60 to 100. In other embodiments, the symbol z is an integer from 10 to 80. In other embodiments, the symbol z is an integer from 15 to 80. In other embodiments, the symbol z is an integer from 20 to 80. In other embodiments, the symbol z is an integer from 25 to 80. In other embodiments, the symbol z is an integer from 30 to 80. In other embodiments, the symbol z is an integer from 35 to 80. In other embodiments, the symbol z is an integer from 40 to 80. In other embodiments, the symbol z is an integer from 45 to 80. In other embodiments, the symbol z is an integer from 50 to 80. In other embodiments, the symbol z is an integer from 55 to 80. In other embodiments, the symbol z is an integer from 60 to 80. In other embodiments, the symbol z is an integer from 10 to 60. In other embodiments, the symbol z is an integer from 15 to 60. In other embodiments, the symbol z is an integer from 20 to 60. In other embodiments, the symbol z is an integer from 25 to 60. In other embodiments, the symbol z is an integer from 30 to 60. In other embodiments, the symbol z is an integer from 35 to 60. In other embodiments, the symbol z is an integer from 40 to 60. In other embodiments, the symbol z is an integer from 45 to 60. In other embodiments, the symbol z is an integer from 50 to 60. In other embodiments, the symbol z is an integer from 55 to 60. In some embodiments, z is 10. In other embodiments, z is 18. In other embodiments, z is 25. In some embodiments, z is 30. In some embodiments, z is 35. In some related embodiments, $R^1$ is $R^{10}$-substituted or unsubstituted $C_{10}$-$C_{50}$ alkyl. In some other related embodiments, $R^1$ is $R^{10}$-substituted or unsubstituted $C_{12}$-$C_{50}$ alkyl. In some other related embodiments, $R^1$ is $R^{10}$-substituted or unsubstituted $C_{14}$-$C_{50}$ alkyl. In some other related embodiments, $R^1$ is $R^{10}$-substituted or unsubstituted $C_{16}$-$C_{50}$ alkyl. In other related embodiments, $R^1$ is $R^{10}$-substituted or unsubstituted $C_{10}$-$C_{30}$ alkyl. In some other related embodiments, $R^1$ is $R^{10}$-substituted or unsubstituted $C_{12}$-$C_{30}$ alkyl. In some other related embodiments, $R^1$ is $R^{10}$-substituted or unsubstituted $C_{14}$-$C_{30}$ alkyl. In some other related embodiments, $R^1$ is $R^{10}$-substituted or unsubstituted $C_{16}$-$C_{30}$ alkyl.

$R^1$ may be $R^{10}$-substituted unsubstituted alkyl. In some embodiments, $R^1$ is $R^{10}$-substituted or unsubstituted $C_8$-$C_{50}$ alkyl. In some embodiments, $R^1$ is $R^{10}$-substituted or unsubstituted $C_{10}$-$C_{50}$ alkyl. In some embodiments, $R^1$ is $R^{10}$-substituted or unsubstituted $C_{12}$-$C_{50}$ alkyl. In some embodiments, $R^1$ is $R^{10}$-substituted or unsubstituted $C_{14}$-$C_{50}$ alkyl. In some embodiments, $R^1$ is $R^{10}$-substituted or unsubstituted $C_{16}$-$C_{50}$ alkyl. In some embodiments, $R^1$ is $R^{10}$-substituted or unsubstituted $C_{18}$-$C_{50}$ alkyl. In some embodiments, $R^1$ is $R^{10}$-substituted or unsubstituted $C_{20}$-$C_{50}$ alkyl. In some embodiments, $R^1$ is $R^{10}$-substituted or unsubstituted $C_{22}$-$C_{50}$ alkyl. In some embodiments, $R^1$ $R^{10}$-substituted or unsubstituted $C_{24}$-$C_{50}$ alkyl. In some embodiments, $R^1$ is $R^{10}$-substituted or unsubstituted $C_{26}$-$C_{50}$ alkyl. In some embodiments, $R^1$ is $R^{10}$-substituted or unsubstituted $C_{28}$-$C_{50}$ alkyl. In some embodiments, $R^1$ is $R^{10}$-substituted or unsubstituted $C_{30}$-$C_{50}$ alkyl. In some embodiments, $R^1$ is $R^{10}$-substituted or unsubstituted $C_8$-$C_{45}$ alkyl. In some embodiments, $R^1$ is $R^{10}$-substituted or unsubstituted $C_{10}$-$C_{45}$ alkyl. In some embodiments, $R^1$ is $R^{10}$-substituted or unsubstituted $C_{12}$-$C_{45}$ alkyl. In some embodiments, $R^1$ is $R^{10}$-substituted or unsubstituted $C_{14}$-$C_{45}$ alkyl. In some embodiments, $R^1$ is $R^{10}$-substituted or unsubstituted $C_{16}$-$C_{45}$ alkyl. In some embodiments, $R^1$ is $R^{10}$-substituted or unsubstituted $C_{18}$-$C_{45}$ alkyl. In some embodiments, $R^1$ is $R^{10}$-substituted or unsubstituted $C_{20}$-$C_{45}$ alkyl. In some embodiments, $R^1$ is $R^{10}$-substituted or unsubstituted $C_{22}$-$C_{45}$ alkyl. In some embodiments, $R^1$ is $R^{10}$-substituted or unsubstituted $C_{24}$-$C_{45}$ alkyl. In some embodiments, $R^1$ is $R^{10}$-substituted or unsubstituted $C_{26}$-$C_{45}$ alkyl. In some embodiments, $R^1$ is $R^{10}$-substituted or unsubstituted $C_{28}$-$C_{45}$ alkyl. In some embodiments, $R^1$ is $R^{10}$-substituted or unsubstituted $C_{30}$-$C_{45}$ alkyl. In some embodiments, $R^1$ is $R^{10}$-substituted or unsubstituted $C_8$-$C_{40}$ alkyl. In some embodiments, $R^1$ is $R^{10}$-substituted or unsubstituted $C_{10}$-$C_{40}$ alkyl. In some embodiments, $R^1$ is $R^{10}$-substituted or unsubstituted $C_{12}$-$C_{40}$ alkyl. In some embodiments, $R^1$ is $R^{10}$-substituted or unsubstituted $C_{14}$-$C_{40}$ alkyl. In some embodiments, $R^1$ is $R^{10}$-substituted or unsubstituted $C_{16}$-$C_{40}$ alkyl. In some embodiments, $R^1$ is $R^{10}$-substituted or unsubstituted $C_{18}$-$C_{40}$ alkyl. In some embodiments, $R^1$ is $R^{10}$-substituted or unsubstituted $C_{20}$-$C_{40}$ alkyl. In some embodiments, $R^1$ is $R^{10}$-substituted or unsubstituted $C_{22}$-$C_{40}$ alkyl. In some embodiments, $R^1$ is $R^{10}$-substituted or unsubstituted $C_{24}$-$C_{40}$ alkyl. In some embodiments, $R^1$ is $R^{10}$-substituted or unsubstituted $C_{26}$-$C_{40}$ alkyl. In some embodiments, $R^1$ is $R^{10}$-substituted or unsubstituted $C_{28}$-$C_{40}$ alkyl. In some embodiments, $R^1$ is $R^{10}$-substituted or unsubstituted $C_{30}$-$C_{40}$ alkyl. In some embodiments, $R^1$ is $R^{10}$-substituted or unsubstituted $C_8$-$C_{35}$ alkyl. In some embodiments, $R^1$ is $R^{10}$-substituted or unsubstituted $C_{10}$-$C_{35}$ alkyl. In some embodiments, $R^1$ is $R^{10}$-substituted or unsubstituted $C_{12}$-$C_{35}$ alkyl. In some embodiments, $R^1$ is $R^{10}$-substituted or unsubstituted $C_{14}$-$C_{35}$ alkyl. In some embodiments, $R^1$ is $R^{10}$-substituted or unsubstituted $C_{16}$-$C_{35}$ alkyl. In some embodiments, $R^1$ is $R^{10}$-substituted or unsubstituted $C_{18}$-$C_{35}$ alkyl. In some embodiments, $R^1$ is $R^{10}$-substituted or unsubstituted $C_{20}$-$C_{35}$ alkyl. In some embodiments, $R^1$ is $R^{10}$-substituted or unsubstituted $C_{22}$-$C_{35}$ alkyl. In some embodiments, $R^1$ is $R^{10}$-substituted or unsubstituted $C_{24}$-$C_{35}$ alkyl. In some embodiments, $R^1$ is $R^{10}$-substituted or unsubstituted $C_{26}$-$C_{35}$ alkyl. In some embodiments, $R^1$ is $R^{10}$-substituted or unsubstituted $C_{28}$-$C_{35}$ alkyl. In some embodiments, $R^1$ is $R^{10}$-substituted or unsubstituted $C_{30}$-$C_{35}$ alkyl. In some related embodiments, the alkyl is a saturated alkyl. In other related embodiments, z is as defined in an embodiment above (e.g. z is at least 5, or at least 25, e.g. 10 to 35).

In some embodiments, $R^1$ is $R^{10}$-substituted or unsubstituted $C_{10}$-$C_{30}$ alkyl. In some embodiments, $R^1$ is $R^{10}$-substituted or unsubstituted $C_{12}$-$C_{30}$ alkyl. In some embodiments, $R^1$ is $R^{10}$-substituted or unsubstituted $C_{14}$-$C_{30}$ alkyl. In some embodiments, $R^1$ is $R^{10}$-substituted or unsubstituted $C_{16}$-$C_{30}$ alkyl. In some embodiments, the alkyl is a branched alkyl. In other embodiments, the alkyl is a saturated alkyl. In other related embodiments, z is as defined in an embodiment above (e.g. z is at least 5, or at least 25, e.g. 10 to 35).

In other embodiments, $R^1$ is $R^{10}$-substituted or unsubstituted $C_{10}$-$C_{20}$ alkyl. In some embodiments, $R^1$ is $R^{10}$-substituted or unsubstituted $C_{12}$-$C_{20}$ alkyl. In some embodiments, $R^1$ is $R^{10}$-substituted or unsubstituted $C_{14}$-$C_{20}$ alkyl. In some embodiments, $R^1$ is $R^{10}$-substituted or unsubstituted $C_{16}$-$C_{20}$ alkyl. In some embodiments, the alkyl is a branched alkyl. In other embodiments, the alkyl is a saturated alkyl. In other related embodiments, z is as defined in an embodiment above (e.g. z is at least 5, or at least 25, e.g. 10 to 35).

In some embodiments, $R^1$ is branched unsubstituted $C_8$-$C_{50}$ alkyl. In other embodiments, $R^1$ is linear unsubstituted $C_8$-$C_{50}$ alkyl. In some embodiments, $R^1$ is branched unsubstituted $C_{10}$-$C_{50}$ alkyl. In other embodiments, $R^1$ is linear unsubstituted $C_{10}$-$C_{50}$ alkyl. In some embodiments, $R^1$ is branched unsubstituted $C_{12}$-$C_{50}$ alkyl. In other embodiments, $R^1$ is linear unsubstituted $C_{12}$-$C_{50}$ alkyl. In some embodiments, $R^1$ is branched unsubstituted $C_{14}$-$C_{50}$ alkyl. In other embodiments, $R^1$ is linear unsubstituted $C_{14}$-$C_{50}$ alkyl. In some embodiments, $R^1$ is branched unsubstituted $C_{16}$-$C_{50}$ alkyl. In other embodiments, $R^1$ is linear unsubstituted $C_{16}$-$C_{50}$ alkyl. In some embodiments, $R^1$ is branched unsubstituted $C_{18}$-$C_{50}$ alkyl. In other embodiments, $R^1$ is linear unsubstituted $C_{18}$-$C_{50}$ alkyl. In some embodiments, $R^1$ is branched unsubstituted $C_{20}$-$C_{50}$ alkyl. In other embodiments, $R^1$ is linear unsubstituted $C_{20}$-$C_{50}$ alkyl. In some embodiments, $R^1$ is branched unsubstituted $C_{22}$-$C_{50}$ alkyl. In other embodiments, $R^1$ is linear unsubstituted $C_{22}$-$C_{50}$ alkyl. In some embodiments, $R^1$ is branched unsubstituted $C_{24}$-$C_{50}$ alkyl. In other embodiments, $R^1$ is linear unsubstituted $C_{24}$-$C_{50}$ alkyl. In some embodiments, $R^1$ is branched unsubstituted $C_{26}$-$C_{50}$ alkyl. In other embodiments, $R^1$ is linear unsubstituted $C_{26}$-$C_{50}$ alkyl. In some embodiments, $R^1$ is branched unsubstituted $C_{28}$-$C_{50}$ alkyl. In other embodiments, $R^1$ is linear unsubstituted $C_{28}$-$C_{50}$ alkyl. In some embodiments, $R^1$ is branched unsubstituted $C_{30}$-$C_{50}$ alkyl. In other embodiments, $R^1$ is linear unsubstituted $C_{30}$-$C_{50}$ alkyl. In some embodiments, $R^1$ is branched unsubstituted $C_{32}$-$C_{50}$ alkyl. In other embodiments, $R^1$ is linear unsubstituted $C_{32}$-$C_{50}$ alkyl. In some embodiments, $R^1$ is branched unsubstituted $C_{34}$-$C_{50}$ alkyl. In other embodiments, $R^1$ is linear unsubstituted $C_{34}$-$C_{50}$ alkyl. In other related embodiments, z is as defined in an embodiment above (e.g. z is at least 5, or at least 25, e.g. 10 to 35).

In some embodiments, $R^1$ is branched unsubstituted $C_8$-$C_{40}$ alkyl. In other embodiments, $R^1$ is linear unsubstituted $C_8$-$C_{40}$ alkyl. In some embodiments, $R^1$ is branched unsubstituted $C_{10}$-$C_{40}$ alkyl. In other embodiments, $R^1$ is linear unsubstituted $C_{10}$-$C_{40}$ alkyl. In some embodiments, $R^1$ is branched unsubstituted $C_{12}$-$C_{40}$ alkyl. In other embodiments, $R^1$ is linear unsubstituted $C_{12}$-$C_{40}$ alkyl. In some embodiments, $R^1$ is branched unsubstituted $C_{14}$-$C_{40}$ alkyl. In other embodiments, $R^1$ is linear unsubstituted $C_{14}$-$C_{40}$ alkyl. In some embodiments, $R^1$ is branched unsubstituted $C_{16}$-$C_{40}$ alkyl. In other embodiments, $R^1$ is linear unsubstituted $C_{16}$-$C_{40}$ alkyl. In some embodiments, $R^1$ is branched unsubstituted $C_{18}$-$C_{40}$ alkyl. In other embodiments, $R^1$ is linear unsubstituted $C_{18}$-$C_{40}$ alkyl. In some embodiments, $R^1$ is branched unsubstituted $C_{20}$-$C_{40}$ alkyl. In other embodiments, $R^1$ is linear unsubstituted $C_{20}$-$C_{40}$ alkyl. In some embodiments, $R^1$ is branched unsubstituted $C_{22}$-$C_{40}$ alkyl. In other embodiments, $R^1$ is linear unsubstituted $C_{22}$-$C_{40}$ alkyl. In some embodiments, $R^1$ is branched unsubstituted $C_{24}$-$C_{40}$ alkyl. In other embodiments, $R^1$ is linear unsubstituted $C_{24}$-$C_{40}$ alkyl. In some embodiments, $R^1$ is branched unsubstituted $C_{26}$-$C_{40}$ alkyl. In other embodiments, $R^1$ is linear unsubstituted $C_{26}$-$C_{40}$ alkyl. In some embodiments, $R^1$ is branched unsubstituted $C_{28}$-$C_{40}$ alkyl. In other embodiments, $R^1$ is linear unsubstituted $C_{28}$-$C_{40}$ alkyl. In some embodiments, $R^1$ is branched unsubstituted $C_{30}$-$C_{40}$ alkyl. In other embodiments, $R^1$ is linear unsubstituted $C_{30}$-$C_{40}$ alkyl. In some embodiments, $R^1$ is branched unsubstituted $C_{32}$-$C_{40}$ alkyl. In other embodiments, $R^1$ is linear unsubstituted $C_{32}$-$C_{40}$ alkyl. In some embodiments, $R^1$ is branched unsubstituted $C_{34}$-$C_{40}$ alkyl. In other embodiments, $R^1$ is linear unsubstituted $C_{34}$-$C_{40}$ alkyl. In other related embodiments, z is as defined in an embodiment above (e.g. z is at least 5, or at least 25, e.g. 10 to 35).

In some embodiments, $R^1$ is branched unsubstituted $C_8$-$C_{30}$ alkyl. In other embodiments, $R^1$ is linear unsubstituted $C_8$-$C_{30}$ alkyl. In some embodiments, $R^1$ is branched unsubstituted C10-$C_{30}$ alkyl. In other embodiments, $R^1$ is linear unsubstituted $C_{10}$-$C_{30}$ alkyl. In some embodiments, $R^1$ is branched unsubstituted $C_{12}$-$C_{30}$ alkyl. In other embodiments, $R^1$ is linear unsubstituted $C_{12}$-$C_{30}$ alkyl. In some embodiments, $R^1$ is branched unsubstituted $C_{14}$-$C_{30}$ alkyl. In other embodiments, $R^1$ is linear unsubstituted $C_{14}$-$C_{30}$ alkyl. In some embodiments, $R^1$ is branched unsubstituted $C_{16}$-$C_{30}$ alkyl. In other embodiments, $R^1$ is linear unsubstituted $C_{16}$-$C_{30}$ alkyl. In some embodiments, $R^1$ is branched unsubstituted $C_{18}$-$C_{30}$ alkyl. In other embodiments, $R^1$ is linear unsubstituted $C_{18}$-$C_{30}$ alkyl. In some embodiments, $R^1$ is branched unsubstituted $C_{20}$-$C_{30}$ alkyl. In other embodiments, $R^1$ is linear unsubstituted $C_{20}$-$C_{30}$ alkyl. In some embodiments, $R^1$ is branched unsubstituted $C_{22}$-$C_{30}$ alkyl. In other embodiments, $R^1$ is linear unsubstituted $C_{22}$-$C_{30}$ alkyl. In some embodiments, $R^1$ is branched unsubstituted $C_{24}$-$C_{30}$ alkyl. In other embodiments, $R^1$ is linear unsubstituted $C_{24}$-$C_{30}$ alkyl. In some embodiments, $R^1$ is branched unsubstituted $C_{26}$-$C_{30}$ alkyl. In other embodiments, $R^1$ is linear unsubstituted $C_{26}$-$C_{30}$ alkyl. In some embodiments, $R^1$ is branched unsubstituted $C_{28}$-$C_{30}$ alkyl. In other embodiments, $R^1$ is linear unsubstituted $C_{28}$-$C_{30}$ alkyl. In other related embodiments, z is as defined in an embodiment above (e.g. z is at least 10, or at least 25, e.g. 15 to 35).

In some embodiments, where $R^1$ is a linear or branched unsubstituted alkyl (e.g. branched unsubstituted $C_{10}$-$C_{50}$ alkyl), the alkyl is a saturated alkyl (e.g. a linear or branched unsubstituted saturated alkyl or branched unsubstituted $C_{10}$-$C_{50}$ saturated alkyl). A "saturated alkyl," as used herein, refers to an alkyl consisting only of hydrogen and carbon atoms and are bonded exclusively by single bonds. Thus, in some embodiments, $R^1$ may be linear or branched unsubstituted saturated alkyl. In some embodiments, $R^1$ is branched unsubstituted $C_{10}$-$C_{50}$ saturated alkyl. In other embodiments, $R^1$ is linear unsubstituted $C_{10}$-$C_{50}$ saturated alkyl. In some embodiments, $R^1$ is branched unsubstituted $C_{16}$-$C_{50}$ saturated alkyl. In other embodiments, $R^1$ is linear unsubstituted $C_{16}$-$C_{50}$ saturated alkyl. In some embodiments, $R^1$ is branched unsubstituted $C_{12}$-$C_{16}$ saturated alkyl. In other embodiments, $R^1$ is linear unsubstituted $C_{12}$-$C_{16}$ saturated alkyl. In other embodiments, $R^1$ is linear unsubstituted $C_{12}$-$C_{16}$ saturated alkyl. In other embodiments, $R^1$ is branched unsubstituted $C_{12}$-$C_{16}$ saturated alkyl.

$R^2$ may be $R^{10a}$-substituted or unsubstituted $C_8$-$C_{50}$ alkyl. In some embodiments, $R^2$ is $R^{10a}$-substituted or unsubstituted $C_{10}$-$C_{50}$ alkyl. In some embodiments, $R^2$ is $R^{10a}$-substituted or unsubstituted $C_{12}$-$C_{50}$ alkyl. In some embodiments, $R^2$ is $R^{10a}$-substituted or unsubstituted $C_{14}$-$C_{150}$ alkyl. In some embodiments, $R^2$ is $R^{10a}$-substituted or unsubstituted $C_{16}$-$C_{50}$ alkyl. In some embodiments, $R^2$ is $R^{10a}$-substituted or unsubstituted $C_{18}$-$C_{50}$ alkyl. In some embodiments, $R^2$ is $R^{10a}$-substituted or unsubstituted $C_{20}$-$C_{50}$ alkyl. In some embodiments, $R^2$ is $R^{10a}$-substituted or unsubstituted $C_{22}$-$C_{50}$ alkyl. In some embodiments, $R^2$ is $R^{10a}$-substituted or unsubstituted $C_{24}$-$C_{50}$ alkyl. In some embodiments, $R^2$ is $R^{10a}$-substituted or unsubstituted $C_{26}$-$C_{50}$ alkyl. In some embodiments, $R^2$ is $R^{10a}$-substituted or unsubstituted $C_{28}$-$C_{50}$ alkyl. In some embodiments, $R^2$ is $R^{10a}$-substituted or unsubstituted $C_{30}$-$C_{50}$ alkyl. In some embodiments, $R^2$ is $R^{10a}$-substituted or unsubstituted $C_8$-$C_{45}$ alkyl. In some embodiments, $R^2$ is $R^{10a}$-substituted or unsubstituted $C_{10}$-$C_{100}$ alkyl. In some embodiments, $R^2$ is $R^{10a}$-substituted or unsubstituted $C_{12}$-$C_{100}$ alkyl. In some embodiments, $R^2$ is $R^{10a}$-substituted or unsubstituted $C_{14}$-$C_{100}$ alkyl. In some embodiments, $R^2$ is $R^{10a}$-substituted or unsubstituted $C_{16}$-$C_{100}$ alkyl. In some embodiments, $R^2$ is $R^{10a}$-substituted or unsubstituted $C_{18}$-$C_{100}$ alkyl. In some embodiments, $R^2$ is $R^{10a}$-substituted or unsubstituted $C_{20}$-$C_{100}$ alkyl. In some embodiments, $R^2$ is $R^{10a}$-substituted or unsubstituted $C_{22}$-$C_{100}$ alkyl. In some embodiments, $R^2$ is $R^{10a}$-substituted or unsubstituted $C_{24}$-$C_{100}$ alkyl. In some embodiments, $R^2$ is $R^{10a}$-substituted or unsubstituted $C_{26}$-$C_{100}$ alkyl. In some embodiments, $R^2$ is $R^{10a}$-substituted or unsubstituted $C_{28}$-$C_{100}$ alkyl. In some embodiments, $R^2$ is $R^{10a}$-substituted or unsubstituted $C_{30}$-$C_{100}$ alkyl. In some embodiments, $R^2$ is $R^{10a}$-substituted or unsubstituted $C_8$-$C_{50}$ alkyl. In some embodiments, $R^2$ is $R^{10a}$-substituted or unsubstituted $C_{10}$-$C_{50}$ alkyl. In some embodiments, $R^2$ is $R^{10a}$-substituted or unsubstituted $C_{12}$-$C_{50}$ alkyl. In some embodiments, $R^2$ is $R^{10a}$-substituted or unsubstituted $C_{14}$-$C_{50}$ alkyl. In some embodiments, $R^2$ is $R^{10a}$-substituted or unsubstituted $C_{16}$-$C_{50}$ alkyl. In some embodiments, $R^2$ is $R^{10a}$-substituted or unsubstituted $C_{18}$-$C_{50}$ alkyl. In some embodiments, $R^2$ is $R^{10a}$-substituted or unsubstituted $C_{50}$-$C_{40}$ alkyl. In some embodiments, $R^2$ is $R^{10a}$-substituted or unsubstituted $C_{22}$-$C_{50}$ alkyl. In some embodiments, $R^2$ is $R^{10a}$-substituted or unsubstituted $C_{24}$-$C_{50}$ alkyl. In some embodiments, $R^2$ is $R^{10a}$-substituted or unsubstituted $C_{26}$-$C_{50}$ alkyl. In some embodiments, $R^2$ is $R^{10a}$-substituted or unsubstituted $C_{28}$-$C_{50}$ alkyl. In some embodiments, $R^2$ is $R^{10a}$-substituted or unsubstituted $C_{30}$-$C_{50}$ alkyl. In some related embodiments, the alkyl is a saturated alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, $R^2$ is $R^{10a}$-substituted or unsubstituted $C_8$-$C_{35}$ alkyl. In some embodiments, $R^2$ is $R^{10a}$-substituted or unsubstituted $C_{10}$-$C_{35}$ alkyl. In some embodiments, $R^2$ is $R^{10a}$-substituted or unsubstituted $C_{12}$-$C_{35}$ alkyl. In some embodiments, $R^2$ is $R^{10a}$-substituted or unsubstituted $C_{14}$-$C_{35}$ alkyl. In some embodiments, $R^2$ is $R^{10a}$-substituted or unsubstituted $C_{16}$-$C_{35}$ alkyl. In some embodiments, $R^2$ is $R^{10a}$-substituted or unsubstituted $C_{18}$-$C_{35}$ alkyl. In some embodiments, $R^2$ is $R^{10a}$-substituted or unsubstituted $C_{20}$-$C_{35}$ alkyl. In some embodiments, $R^2$ is $R^{10a}$-substituted or unsubstituted $C_{22}$-$C_{35}$ alkyl. In some embodiments, $R^2$ is $R^{10a}$-substituted or unsubstituted $C_{24}$-$C_{35}$ alkyl. In some embodiments, $R^2$ is $R^{10a}$-substituted or unsubstituted $C_{26}$-$C_{35}$ alkyl. In some embodiments, $R^2$ is $R^{10a}$-substituted or unsubstituted $C_{28}$-$C_{35}$ alkyl. In some embodiments, $R^2$ is $R^{10a}$-substituted or unsubstituted $C_{30}$-$C_{35}$ alkyl. In some related embodiments, the alkyl is a saturated alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, $R^2$ is $R^{10a}$-substituted or unsubstituted $C_{10}$-$C_{30}$ alkyl. In some embodiments, $R^2$ is $R^{10a}$-substituted or unsubstituted $C_{12}$-$C_{30}$ alkyl. In some embodiments, $R^2$ is $R^{10a}$-substituted or unsubstituted $C_{14}$-$C_{30}$ alkyl. In some embodiments, $R^2$ is $R^{10a}$-substituted or unsubstituted $C_{16}$-$C_{30}$ alkyl. In some embodiments, the alkyl is a branched alkyl. In other embodiments, the alkyl is a saturated alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is $R^{10a}$-substituted or unsubstituted $C_{10}$-$C_{20}$ alkyl. In some embodiments, $R^2$ is $R^{10a}$-substituted or unsubstituted $C_{12}$-$C_{20}$ alkyl. In some embodiments, $R^2$ is $R^{10a}$-substituted or unsubstituted $C_{14}$-$C_{20}$ alkyl. In some embodiments, $R^2$ is $R^{10a}$-substituted or unsubstituted $C_{16}$-$C_{20}$ alkyl. In some embodiments, the alkyl is a branched alkyl. In other embodiments, the alkyl is a saturated alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, $R^2$ is branched unsubstituted $C_8$-$C_{50}$ alkyl. In other embodiments, $R^2$ is linear unsubstituted $C_8$-$C_{50}$ alkyl. In some embodiments, $R^2$ is branched unsubstituted $C_{10}$-$C_{50}$ alkyl. In other embodiments, $R^2$ is linear unsubstituted $C_{10}$-$C_{50}$ alkyl. In some embodiments, $R^2$ is branched unsubstituted $C_{12}$-$C_{50}$ alkyl. In other embodiments, $R^2$ is linear unsubstituted $C_{12}$-$C_{50}$ alkyl. In some embodiments, $R^2$ is branched unsubstituted $C_{14}$-$C_{50}$ alkyl. In other embodiments, $R^2$ is linear unsubstituted $C_{14}$-$C_{50}$ alkyl. In some embodiments, $R^2$ is branched unsubstituted $C_{16}$-$C_{50}$ alkyl. In other embodiments, $R^2$ is linear unsubstituted $C_{16}$-$C_{50}$ alkyl. In some embodiments, $R^2$ is branched unsubstituted $C_{18}$-$C_{50}$ alkyl. In other embodiments, $R^2$ is linear unsubstituted $C_{18}$-$C_{50}$ alkyl. In some embodiments, $R^2$ is branched unsubstituted $C_{20}$-$C_{50}$ alkyl. In other embodiments, $R^2$ is linear unsubstituted $C_{20}$-$C_{50}$ alkyl. In some embodiments, $R^2$ is branched unsubstituted $C_{22}$-$C_{50}$ alkyl. In other embodiments, $R^2$ is linear unsubstituted $C_{22}$-$C_{50}$ alkyl. In some embodiments, $R^2$ is branched unsubstituted $C_{24}$-$C_{50}$ alkyl. In other embodiments, $R^2$ is linear unsubstituted $C_{24}$-$C_{50}$ alkyl. In some embodiments, $R^2$ is branched unsubstituted $C_{26}$-$C_{50}$ alkyl. In other embodiments, $R^2$ is linear unsubstituted $C_{26}$-$C_{50}$ alkyl. In some embodiments, $R^2$ is branched unsubstituted $C_{28}$-$C_{50}$ alkyl. In other embodiments, $R^2$ is linear unsubstituted $C_{28}$-$C_{50}$ alkyl. In some embodiments, $R^2$ is branched unsubstituted $C_{30}$-$C_{50}$ alkyl. In other embodiments, $R^2$ is linear unsubstituted $C_{30}$-$C_{50}$ alkyl. In some embodiments, $R^2$ is branched unsubstituted $C_{32}$-$C_{50}$ alkyl. In other embodiments, $R^2$ is linear unsubstituted $C_{32}$-$C_{50}$ alkyl. In some embodiments, $R^2$ is branched unsubstituted $C_{34}$-$C_{50}$ alkyl. In other embodiments, $R^2$ is linear unsubstituted $C_{34}$-$C_{50}$ alkyl. In some embodiments, $R^2$ is branched unsubstituted $C_{20}$-$C_{50}$ alkyl or linear unsubstituted $C_{16}$-$C_{40}$ alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, $R^2$ is branched unsubstituted $C_8$-$C_{40}$ alkyl. In other embodiments, $R^2$ is linear unsubstituted $C_8$-$C_{40}$ alkyl. In some embodiments, $R^2$ is branched unsubstituted $C_{10}$-$C_{40}$ alkyl. In other embodiments, $R^2$ is linear unsubstituted $C_{10}$-$C_{40}$ alkyl. In some embodiments, $R^2$ is branched unsubstituted $C_{12}$-$C_{40}$ alkyl. In other embodiments, $R^2$ is linear unsubstituted $C_{12}$-$C_{40}$ alkyl. In some embodiments, $R^2$ is branched unsubstituted $C_{14}$-$C_{40}$ alkyl. In other embodiments, $R^2$ is linear unsubstituted $C_{14}$-$C_{40}$ alkyl. In some embodiments, $R^2$ is branched unsubstituted $C_{16}$-$C_{40}$ alkyl. In other embodiments, $R^2$ is linear unsubstituted $C_{16}$-$C_{40}$ alkyl. In some embodiments, $R^2$ is branched unsubstituted $C_{18}$-$C_{40}$ alkyl. In other embodiments, $R^2$ is linear unsubstituted $C_{18}$-$C_{40}$ alkyl. In some embodiments, $R^2$ is branched unsubstituted $C_{20}$-$C_{40}$ alkyl. In other embodiments, $R^2$ is linear unsubstituted $C_{20}$-$C_{40}$ alkyl. In some embodiments, $R^2$ is branched unsubstituted $C_{22}$-$C_{40}$ alkyl. In other embodiments, $R^2$ is linear unsubstituted $C_{22}$-$C_{40}$ alkyl. In some embodiments, $R^2$ is branched unsubstituted $C_{24}$-$C_{40}$ alkyl. In other embodiments, $R^2$ is linear unsubstituted $C_{24}$-$C_{40}$ alkyl. In some embodiments, $R^2$ is branched unsubstituted $C_{26}$-$C_{40}$ alkyl. In other embodiments, $R^2$ is linear unsubstituted $C_{26}$-$C_{40}$ alkyl. In some embodiments, $R^2$ is branched unsubstituted $C_{28}$-$C_{40}$ alkyl. In other embodiments, $R^2$ is linear unsubstituted $C_{28}$-$C_{40}$ alkyl. In some embodiments, $R^2$ is branched unsubstituted $C_{30}$-$C_{40}$ alkyl. In other embodiments, $R^2$ is linear unsubstituted $C_{30}$-$C_{40}$ alkyl. In some embodiments, $R^2$ is branched unsubstituted $C_{32}$-$C_{40}$ alkyl. In other embodiments, $R^2$ is linear unsubstituted $C_{32}$-$C_{40}$ alkyl. In some embodiments, $R^2$ is branched unsubstituted $C_{34}$-$C_{40}$ alkyl. In other embodiments, $R^2$ is linear unsubstituted $C_{34}$-$C_{40}$ alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, $R^2$ is branched unsubstituted $C_8$-$C_{30}$ alkyl. In other embodiments, $R^2$ is linear unsubstituted $C_8$-$C_{30}$ alkyl. In some embodiments, $R^2$ is branched unsubstituted $C_{10}$-$C_{30}$ alkyl. In other embodiments, $R^2$ is linear unsubstituted $C_{10}$-$C_{30}$ alkyl. In some embodiments, $R^2$ is branched unsubstituted $C_{12}$-$C_{30}$ alkyl. In other embodiments, $R^2$ is linear unsubstituted $C_{12}$-$C_{30}$ alkyl. In some embodiments, $R^2$ is branched unsubstituted $C_{14}$-$C_{30}$ alkyl. In other embodiments, $R^2$ is linear unsubstituted $C_{14}$-$C_{30}$ alkyl. In some embodiments, $R^2$ is branched unsubstituted $C_{16}$-$C_{30}$ alkyl. In other embodiments, $R^2$ is linear unsubstituted $C_{16}$-$C_{30}$ alkyl. In some embodiments, $R^2$ is branched unsubstituted $C_{18}$-$C_{30}$ alkyl. In other embodiments, $R^2$ is linear unsubstituted $C_{18}$-$C_{30}$ alkyl. In some embodiments, $R^2$ is branched unsubstituted $C_{20}$-$C_{30}$ alkyl. In other embodiments, $R^2$ is linear unsubstituted $C_{20}$-$C_{30}$ alkyl. In some embodiments, $R^2$ is branched unsubstituted $C_{22}$-$C_{30}$ alkyl. In other embodiments, $R^2$ is linear unsubstituted $C_{22}$-$C_{30}$ alkyl. In some embodiments, $R^2$ is branched unsubstituted $C_{24}$-$C_{30}$ alkyl. In other embodiments, $R^2$ is linear unsubstituted $C_{24}$-$C_{30}$ alkyl. In some embodiments, $R^2$ is branched unsubstituted $C_{26}$-$C_{30}$ alkyl. In other embodiments, $R^2$ is linear unsubstituted $C_{26}$-$C_{30}$ alkyl. In some embodiments, $R^2$ is branched unsubstituted $C_{28}$-$C_{30}$ alkyl. In other embodiments, $R^2$ is linear unsubstituted $C_{28}$-$C_{30}$ alkyl. In other related embodiments, z is as defined in an embodiment above (e.g. z is at least 20, or at least 30, e.g. 25 to 35). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, where $R^2$ is a linear or branched unsubstituted alkyl (e.g. branched unsubstituted $C_{10}$-$C_{50}$ alkyl), the alkyl is a saturated alkyl (e.g. a linear or branched unsubstituted saturated alkyl or branched unsubstituted $C_{10}$-$C_{50}$ saturated alkyl). A "saturated alkyl," as used herein, refers to an alkyl consisting only of hydrogen and carbon atoms and are bonded exclusively by single bonds. Thus, in some embodiments, $R^2$ may be linear or branched unsubstituted saturated alkyl. In some embodiments, $R^2$ is branched unsubstituted $C_{10}$-$C_{50}$ saturated alkyl. In other embodiments, $R^2$ is linear unsubstituted $C_{10}$-$C_{50}$ saturated alkyl. In some embodiments, $R^2$ is branched unsubstituted $C_{16}$-$C_{50}$ saturated alkyl. In other embodiments, $R^2$ is linear unsubstituted $C_{16}$-$C_{50}$ saturated alkyl. In some embodiments, $R^2$ is branched unsubstituted $C_{12}$-$C_{16}$ saturated alkyl. In other embodiments, $R^2$ is linear unsubstituted $C_{12}$-$C_{16}$ saturated alkyl. In other embodiments, $R^2$ is linear unsubstituted $C_{12}$-$C_{16}$ saturated alkyl. In other embodiments, $R^2$ is branched unsubstituted $C_{12}$-$C_{16}$ saturated alkyl.

In some embodiments, $R^2$ is formed using the Guerbet reaction.

$R^2$ may be $R^{4a}$-substituted or unsubstituted heteroalkyl. In some embodiments, $R^2$ is $R^{4a}$-substituted or unsubstituted $C_3$-$C_{100}$ heteroalkyl. In other embodiments, $R^2$ is $R^{4a}$-substituted or unsubstituted $C_6$-$C_{00}$ heteroalkyl. In other embodiments, $R^2$ is $R^{4a}$-substituted or unsubstituted $C_{10}$-$C_{100}$ heteroalkyl. In other embodiments, $R^2$ is $R^{4a}$-substituted or unsubstituted $C_{12}$-$C_{100}$ heteroalkyl. In other embodiments, $R^2$ is $R^{4a}$-substituted or unsubstituted $C_{18}$-$C_{100}$ heteroalkyl. In other embodiments, $R^2$ is $R^{4a}$-substituted or unsubstituted $C_{20}$-$C_{100}$ heteroalkyl. In other embodiments, $R^2$ is $R^{4a}$-substituted or unsubstituted $C_{24}$-$C_{100}$ heteroalkyl. In other embodiments, $R^2$ is $R^{4a}$-substituted or unsubstituted $C_{30}$-$C_{100}$ heteroalkyl. In other embodiments, $R^2$ is $R^{4a}$-substituted or unsubstituted $C_{36}$-$C_{100}$ heteroalkyl. In other embodiments, $R^2$ is $R^{4a}$-substituted or unsubstituted $C_{42}$-$C_{100}$ heteroalkyl. In other embodiments, $R^2$ is $R^{4a}$-substituted or unsubstituted $C_{48}$-$C_{100}$ heteroalkyl. In other embodiments, $R^2$ is $R^{4a}$-substituted or unsubstituted $C_{54}$-$C_{100}$ heteroalkyl. In other embodiments, $R^2$ is $R^{4a}$-substituted or unsubstituted $C_{60}$-$C_{100}$ heteroalkyl. In other embodiments, $R^2$ is $R^{4a}$-substituted or unsubstituted $C_{66}$-$C_{100}$ heteroalkyl. In other embodiments, $R^2$ is $R^{4a}$-substituted or unsubstituted $C_{72}$-$C_{100}$ heteroalkyl. In some embodiments, $R^2$ is $R^{4a}$-substituted or unsubstituted $C_3$-$C_{80}$ heteroalkyl. In other embodiments, $R^2$ is $R^{4a}$-substituted or unsubstituted $C_6$-$C_{80}$ heteroalkyl. In other embodiments, $R^2$ is $R^{4a}$-substituted or unsubstituted $C_{10}$-$C_{80}$ heteroalkyl. In other embodiments, $R^2$ is $R^{4a}$-substituted or unsubstituted $C_{12}$-$C_{80}$ heteroalkyl. In other embodiments, $R^2$ is $R^{4a}$-substituted or unsubstituted $C_{18}$-$C_{80}$ heteroalkyl. In other embodiments, $R^2$ is $R^{4a}$-substituted or unsubstituted $C_{20}$-$C_{80}$ heteroalkyl. In other embodiments, $R^2$ is $R^{4a}$-substituted or unsubstituted $C_{24}$-$C_{80}$ heteroalkyl. In other embodiments, $R^2$ is $R^{4a}$-substituted or unsubstituted $C_{30}$-$C_{80}$ heteroalkyl. In other embodiments, $R^2$ is $R^{4a}$-substituted or unsubstituted $C_{36}$-$C_{80}$ heteroalkyl. In other embodiments, $R^2$ is $R^{4a}$-substituted or unsubstituted $C_{42}$-$C_{80}$ heteroalkyl. In other embodiments, $R^2$ is $R^{4a}$-substituted or unsubstituted $C_{48}$-$C_{80}$ heteroalkyl. In other embodiments, $R^2$ is $R^{4a}$-substituted or unsubstituted $C_{54}$-$C_{80}$ heteroalkyl. In other embodiments, $R^2$ is $R^{4a}$-substituted or unsubstituted $C_{60}$-$C_{80}$ heteroalkyl. In other embodiments, $R^2$ is $R^{4a}$-substituted or unsubstituted $C_{66}$-$C_{80}$ heteroalkyl. In other embodiments, $R^2$ is $R^{4a}$-substituted or unsubstituted $C_{72}$-$C_{80}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is $R^{4a}$-substituted or unsubstituted $C_{14}$-$C_{60}$ heteroalkyl. In some embodiments, $R^2$ is $R^{4a}$-substituted or unsubstituted $C_{14}$-$C_{55}$ heteroalkyl. $R^2$ is $R^{4a}$-substituted or unsubstituted $C_{14}$-$C_{50}$ heteroalkyl. $R^2$ is $R^{4a}$-substituted or unsubstituted $C_{14}$-$C_{45}$ heteroalkyl. $R^2$ is $R^{4a}$-substituted or unsubstituted $C_{14}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is $R^{4a}$-substituted or unsubstituted $C_{16}$-$C_{60}$ heteroalkyl. In some embodiments, $R^2$ is $R^{4a}$-substituted or unsubstituted $C_{16}$-$C_{55}$ heteroalkyl. $R^2$ is $R^{4a}$-substituted or unsubstituted $C_{16}$-$C_{50}$ heteroalkyl. $R^2$ is $R^{4a}$-substituted or unsubstituted $C_{16}$-$C_{45}$ heteroalkyl. $R^2$ is $R^{4a}$-substituted or unsubstituted $C_{16}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is $R^{4a}$-substituted or unsubstituted $C_{18}$-$C_{60}$ heteroalkyl. In some embodiments, $R^2$ is $R^{4a}$-substituted or unsubstituted $C_{18}$-$C_{55}$ heteroalkyl. $R^2$ is $R^{4a}$-substituted or unsubstituted $C_{18}$-$C_{50}$ heteroalkyl. $R^2$ is $R^{4a}$-substituted or unsubstituted $C_{18}$-$C_{45}$ heteroalkyl. $R^2$ is $R^{4a}$-substituted or unsubstituted $C_{18}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is $R^{4a}$-substituted or unsubstituted $C_{20}$-$C_{60}$ heteroalkyl. In some embodiments, $R^2$ is $R^{4a}$-substituted or unsubstituted $C_{20}$-$C_{55}$ heteroalkyl. $R^2$ is $R^{4a}$-substituted or unsubstituted $C_{20}$-$C_{50}$ heteroalkyl. $R^2$ is $R^{4a}$-substituted or unsubstituted $C_{20}$-$C_{45}$ heteroalkyl. $R^2$ is $R^{4a}$-substituted or unsubstituted $C_{20}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is $R^{4a}$-substituted or unsubstituted $C_{22}$-$C_{60}$ heteroalkyl. In some embodiments, $R^2$ is $R^{4a}$-substituted or unsubstituted $C_{22}$-$C_{55}$ heteroalkyl. $R^2$ is $R^{4a}$-substituted or unsubstituted $C_{22}$-$C_{50}$ heteroalkyl. $R^2$ is $R^{4a}$-substituted or unsubstituted $C_{22}$-$C_{45}$ heteroalkyl. $R^2$ is $R^{4a}$-substituted or unsubstituted $C_{22}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

$R^2$ may be $R^{4a}$-substituted or unsubstituted heteroalkyl. Where $R^2$ is $R^{4a}$-substituted or unsubstituted heteroalkyl, the heteroalkyl may be a branched or linear heteroalkyl. In some embodiments, $R^2$ is branched $R^{4a}$-substituted or unsubstituted $C_3$-$C_{100}$ heteroalkyl. In other embodiments, $R^2$ is linear $R^{4a}$-substituted or unsubstituted $C_3$-$C_{100}$ heteroalkyl. In some embodiments, $R^2$ is branched $R^{4a}$-substituted or unsubstituted $C_6$-$C_{100}$ heteroalkyl. In other embodiments, $R^2$ is linear $R^{4a}$-substituted or unsubstituted $C_6$-$C_{100}$ heteroalkyl. In some embodiments, $R^2$ is branched $R^{4a}$-substituted or unsubstituted $C_{12}$-$C_{100}$ heteroalkyl. In other embodiments, $R^2$ is linear $R^{4a}$-substituted or unsubstituted $C_{12}$-$C_{100}$ heteroalkyl. In some embodiments, $R^2$ is branched $R^{4a}$-substituted or unsubstituted $C_{18}$-$C_{100}$ heteroalkyl. In other embodiments, $R^2$ is linear $R^{4a}$-substituted or unsubstituted $C_{18}$-$C_{100}$ heteroalkyl. In some embodiments, $R^2$ is branched $R^{4a}$-substituted or unsubstituted $C_{21}$-$C_{100}$ heteroalkyl. In other embodiments, $R^2$ is linear $R^{4a}$-substituted or unsubstituted $C_{21}$-$C_{100}$ heteroalkyl. In some embodiments, $R^2$ is branched $R^{4a}$-substituted or unsubstituted $C_{24}$-$C_{100}$ heteroalkyl. In other embodiments, $R^2$ is linear $R^{4a}$-substituted or unsubstituted $C_{24}$-$C_{100}$ heteroalkyl. In some embodiments, $R^2$ is branched $R^{4a}$-substituted or unsubstituted $C_{27}$-$C_{100}$ heteroalkyl. In other embodiments, $R^2$ is linear $R^{4a}$-substituted or unsubstituted $C_{27}$-$C_{100}$ heteroalkyl. In some embodiments, $R^2$ is branched $R^{4a}$-substituted or unsubstituted $C_{30}$-$C_{100}$ heteroalkyl. In other embodiments, $R^2$ is linear $R^{4a}$-substituted or unsubstituted $C_{30}$-$C_{100}$ heteroalkyl. In some embodiments, $R^2$ is branched $R^{4a}$-substituted or unsubstituted $C_{35}$-$C_{100}$ heteroalkyl. In other embodiments, $R^2$ is linear $R^{4a}$-substituted or unsubstituted $C_{35}$-$C_{100}$ heteroalkyl. In some embodiments, $R^2$ is branched $R^{4a}$-substituted or unsubstituted $C_{40}$-$C_{100}$ heteroalkyl. In other embodiments, $R^2$ is linear $R^{4a}$-substituted or unsubstituted $C_{40}$-$C_{100}$ heteroalkyl. In some embodiments, $R^2$ is branched $R^{4a}$-substituted or unsubstituted $C_{45}$-$C_{100}$ heteroalkyl. In other embodiments, $R^2$ is linear $R^{4a}$-substituted or unsubstituted $C_{45}$-$C_{100}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is branched $R^{4a}$-substituted $C_{14}$-$C_{60}$ heteroalkyl. In some embodiments, $R^2$ is branched $R^{4a}$-substituted $C_{14}$-$C_{55}$ heteroalkyl. $R^2$ is branched $R^{4a}$-substituted $C_{14}$-$C_{50}$ heteroalkyl. $R^2$ is branched $R^{4a}$-substituted $C_{14}$-$C_{45}$ heteroalkyl. $R^2$ is branched $R^{4a}$-substituted $C_{14}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is branched $R^{4a}$-substituted $C_{16}$-$C_{60}$ heteroalkyl. In some embodiments, $R^2$ is branched $R^{4a}$-substituted $C_{16}$-$C_{55}$ heteroalkyl. $R^2$ is branched $R^{4a}$-substituted $C_{16}$-$C_{50}$ heteroalkyl. $R^2$ is branched $R^{4a}$-substituted $C_{16}$-$C_{45}$ heteroalkyl. $R^2$ is branched $R^{4a}$-substituted $C_{16}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is branched $R^{4a}$-substituted $C_{18}$-$C_{60}$ heteroalkyl. In some embodiments, $R^2$ is branched $R^{4a}$-substituted $C_{18}$-$C_{55}$ heteroalkyl. $R^2$ is branched $R^{4a}$-substituted $C_{18}$-$C_{50}$ heteroalkyl. $R^2$ is branched $R^{4a}$-substituted $C_{18}$-$C_{45}$ heteroalkyl. $R^2$ is branched $R^{4a}$-substituted $C_{18}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is branched $R^{4a}$-substituted $C_{20}$-$C_{60}$ heteroalkyl. In some embodiments, $R^2$ is branched $R^{4a}$-substituted $C_{20}$-$C_{55}$ heteroalkyl. $R^2$ is branched $R^{4a}$-substituted $C_{20}$-$C_{50}$ heteroalkyl. $R^2$ is branched $R^{4a}$-substituted $C_{20}$-$C_{45}$ heteroalkyl. $R^2$ is branched $R^{4a}$-substituted $C_{20}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is branched $R^{4a}$-substituted $C_{30}$-$C_{60}$ heteroalkyl. In some embodiments, $R^2$ is branched $R^{4a}$-substituted $C_{30}$-$C_{55}$ heteroalkyl. $R^2$ is branched $R^{4a}$-substituted $C_{30}$-$C_{50}$ heteroalkyl. $R^2$ is branched $R^{4a}$-substituted $C_{30}$-$C_{45}$ heteroalkyl. $R^2$ is branched $R^{4a}$-substituted $C_{30}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In other embodiments, $R^2$ is branched $R^{4a}$-substituted $C_{22}$-$C_{60}$ heteroalkyl. In some embodiments, $R^2$ is branched $R^{4a}$-substituted $C_{22}$-$C_{55}$ heteroalkyl. $R^2$ branched $R^{4a}$-substituted $C_{22}$-$C_{50}$ heteroalkyl. $R^2$ is branched $R^{4a}$-substituted $C_{22}$-$C_{45}$ heteroalkyl. $R^2$ is branched $R^{4a}$-substituted $C_{22}$-$C_{40}$ heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

In some embodiments, where $R^2$ is a linear or branched substituted heteroalkyl (e.g. branched substituted $C_{10}$-$C_{100}$ heteroalkyl), the heteroalkyl is a saturated heteroalkyl (e.g. a linear or branched substituted saturated heteroalkyl, e.g. a branched substituted $C_{10}$-$C_{100}$ saturated heteroalkyl). A "saturated heteroalkyl," as used herein, refers to a heteroalkyl consisting only of hydrogen, carbon atoms and heteroatoms (e.g. oxygen) bonded exclusively by single bonds. Thus, in some embodiments, $R^2$ may be linear or branched substituted saturated heteroalkyl. In some embodiments, $R^2$ is branched $R^{4a}$-substituted $C_{10}$-$C_{100}$ saturated heteroalkyl. In other embodiments, $R^2$ is linear $R^{4a}$-substituted $C_{10}$-$C_{100}$ saturated heteroalkyl. In some embodiments, $R^2$ is branched $R^{4a}$-substituted $C_{10}$-$C_{50}$ saturated heteroalkyl. In other embodiments, $R^2$ is linear $R^{4a}$-substituted $C_{10}$-$C_{50}$ saturated heteroalkyl. In some embodiments, $R^2$ is branched $R^{4a}$-substituted $C_{10}$-$C_{60}$ saturated heteroalkyl. In other embodiments, $R^2$ is linear $R^{4a}$-substituted $C_{10}$-$C_{60}$ saturated heteroalkyl. In some embodiments, $R^2$ is branched $R^{4a}$-substituted $C_{10}$-$C_{50}$ saturated heteroalkyl. In other embodiments, $R^2$ is linear $R^{4a}$-substituted $C_{10}$-$C_{50}$ saturated heteroalkyl. In some embodiments, $R^2$ is branched $R^{4a}$-substituted $C_{20}$-$C_{100}$ saturated heteroalkyl. In other embodiments, $R^2$ is linear $R^{4a}$-substituted $C_{20}$-$C_{100}$ saturated heteroalkyl. In some embodiments, $R^2$ is branched $R^{4a}$-substituted $C_{20}$-$C_{80}$ saturated heteroalkyl. In other embodiments, $R^2$ is linear $R^{4a}$-substituted $C_{20}$-$C_{80}$ saturated heteroalkyl. In some embodiments, $R^2$ is branched $R^{4a}$-substituted $C_{20}$-$C_{60}$ saturated heteroalkyl. In other embodiments, $R^2$ is linear $R^{4a}$-substituted $C_{20}$-$C_{60}$ saturated heteroalkyl. In some embodiments, $R^2$ is branched $R^{4a}$-substituted $C_{20}$-$C_{50}$ saturated heteroalkyl. In other embodiments, $R^2$ is linear $R^{4a}$-substituted $C_{20}$-$C_{50}$ saturated heteroalkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl).

$R^2$ may be $R^{4a}$-substituted heteroalkyl. In some embodiments, $R^{4a}$ is $R^{5a}$-substituted or unsubstituted $C_1$-$C_{50}$ alkyl. In other embodiments, $R^{4a}$ is $R^5$-substituted or unsubstituted $C_5$-$C_{50}$ alkyl. $R^{4a}$ is $R^{5a}$-substituted or unsubstituted $C_{10}$-$C_{50}$ alkyl. $R^{4a}$ is $R^{5a}$-substituted or unsubstituted $C_{12}$-$C_{50}$ alkyl. $R^{4a}$ is $R^{5a}$-substituted or unsubstituted $C_{14}$-$C_{50}$ alkyl. $R^{4a}$ is $R^{5a}$-substituted or unsubstituted $C_{16}$-$C_{50}$ alkyl. $R^{4a}$ is $R^{5a}$-substituted or unsubstituted $C_{18}$-$C_{50}$ alkyl. In some embodiments, $R^{4a}$ is $R^{5a}$-substituted or unsubstituted $C_1$-$C_{40}$ alkyl. In other embodiments, $R^{4a}$ is $R^{5a}$-substituted or unsubstituted $C_5$-$C_{40}$ alkyl. $R^{4a}$ is $R^{5a}$-substituted or unsubstituted $C_{10}$-$C_{40}$ alkyl. $R^{4a}$ is $R^{5a}$-substituted or unsubstituted $C_{12}$-$C_{40}$ alkyl. $R^{4a}$ is $R^{8a}$-substituted or unsubstituted $C_{14}$-$C_{40}$ alkyl. $R^{4a}$ is $R^{5a}$-substituted or unsubstituted $C_{16}$-$C_{40}$ alkyl. $R^{4a}$ is $R^{5a}$-substituted or unsubstituted $C_{18}$-$C_{40}$ alkyl. In some embodiments, $R^{4a}$ is $R^{5a}$-substituted or unsubstituted $C_1$-$C_{30}$ alkyl. In other embodiments, $R^{4a}$ is $R^{5a}$-substituted or unsubstituted $C_5$-$C_{30}$ alkyl. $R^{4a}$ is $R^{5a}$-substituted or unsubstituted $C_{10}$-$C_{30}$ alkyl. $R^{4a}$ is $R^{5a}$-substituted or unsubstituted $C_{12}$-$C_{30}$ alkyl. $R^{4a}$ is $R^{5a}$-substituted or unsubstituted $C_{14}$-$C_{30}$ alkyl. $R^{4a}$ is $R^{5a}$-substituted or unsubstituted $C_{16}$-$C_{30}$ alkyl. $R^{4a}$ is $R^{5a}$-substituted or unsubstituted $C_{18}$-$C_{30}$ alkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl). In other related embodiments, $R^2$ is branched $R^{4a}$-substituted $C_{20}$-$C_{60}$ heteroalkyl, e.g. branched $R^{4a}$-substituted $C_{21}$ or $C_{45}$ heteroalkyl).

In some embodiments, $R^{4a}$ is unsubstituted $C_{10}$-$C_{50}$ alkyl. In some embodiments, $R^{4a}$ is unsubstituted $C_{12}$-$C_{50}$ alkyl. In some embodiments, $R^{4a}$ is unsubstituted $C_{14}$-$C_{50}$ alkyl. In some embodiments, $R^{4a}$ is unsubstituted $C_{16}$-$C_{50}$ alkyl. In some embodiments, $R^{4a}$ is unsubstituted $C_{18}$-$C_{50}$ alkyl. In some embodiments, $R^{4a}$ is unsubstituted $C_{20}$-$C_{50}$ alkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl). In other related embodiments, $R^2$ is branched $R^{4a}$-substituted $C_{20}$-$C_{60}$ heteroalkyl, e.g. branched $R^{4a}$-substituted $C_{21}$ or $C_{45}$ heteroalkyl).

In some embodiments, $R^{4a}$ is unsubstituted $C_{10}$-$C_{50}$ alkyl. In some embodiments, $R^{4a}$ is unsubstituted $C_{12}$-$C_{40}$ alkyl. In some embodiments, $R^{4a}$ is unsubstituted $C_{14}$-$C_{40}$ alkyl. In some embodiments, $R^{4a}$ is unsubstituted $C_{16}$-$C_{40}$ alkyl. In some embodiments, $R^{4a}$ is unsubstituted $C_{18}$-$C_{40}$ alkyl. In some embodiments, $R^{4a}$ is unsubstituted $C_{20}$-$C_{40}$ alkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl). In other related embodiments, $R^2$ is branched $R^{4a}$-substituted $C_{20}$-$C_{60}$ heteroalkyl, e.g. branched $R^{4a}$-substituted $C_{21}$ or $C_{45}$ heteroalkyl).

In some embodiments, $R^{4a}$ is unsubstituted $C_{10}$-$C_{30}$ alkyl. In some embodiments, $R^{4a}$ is unsubstituted $C_{12}$-$C_{30}$ alkyl. In some embodiments, $R^{4a}$ is unsubstituted $C_{14}$-$C_{30}$ alkyl. In some embodiments, $R^{4a}$ is unsubstituted $C_{16}$-$C_{30}$ alkyl. In some embodiments, $R^{4a}$ is unsubstituted $C_{18}$-$C_{30}$ alkyl. In some embodiments, $R^{4a}$ is unsubstituted $C_{20}$-$C_{30}$ alkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl). In other related embodiments, $R^2$ is branched $R^{4a}$-substituted $C_{20}$-$C_{60}$ heteroalkyl, e.g. branched $R^{4a}$-substituted $C_{21}$ or $C_{45}$ heteroalkyl).

$R^{4a}$ may be unsubstituted alkyl. In some embodiments, $R^{4a}$ is linear unsubstituted $C_{10}$-$C_{50}$ alkyl. In other embodiments, $R^{4a}$ is branched unsubstituted $C_{10}$-$C_{50}$ alkyl. In some embodiments, $R^{4a}$ is linear unsubstituted $C_{12}$-$C_{50}$ alkyl. In other embodiments, $R^{4a}$ is branched unsubstituted $C_{12}$-$C_{50}$ alkyl. In some embodiments, $R^{4a}$ is linear unsubstituted $C_{14}$-$C_{50}$ alkyl. In other embodiments, $R^{4a}$ is branched unsubstituted $C_{14}$-$C_{50}$ alkyl. In some embodiments, $R^{4a}$ is linear unsubstituted $C_{16}$-$C_{50}$ alkyl. In other embodiments, $R^{4a}$ is branched unsubstituted $C_{16}$-$C_{50}$ alkyl. In some embodiments, $R^{4a}$ is linear unsubstituted $C_{18}$-$C_{50}$ alkyl. In other embodiments, $R^{4a}$ is branched unsubstituted $C_{18}$-$C_{50}$ alkyl. In some embodiments, $R^{4a}$ is linear unsubstituted $C_{20}$-$C_{50}$ alkyl. In other embodiments, $R^{4a}$ is branched unsubstituted $C_{20}$-$C_{50}$ alkyl. In other related embodiments, z is as defined in an embodiment above (e.g. z is at least 8, or at least 15, e.g. 10 to 18). In other related embodiments, $R^1$ is defined as above (e.g. linear unsubstituted $C_{10}$-$C_{35}$ alkyl, e.g. unsubstituted $C_{14}$ or $C_{16}$ alkyl). In other related embodiments, $R^2$ is branched $R^{4a}$-substituted $C_{20}$-$C_{60}$ heteroalkyl, e.g. branched $R^{4a}$-substituted $C_{21}$ or $C_{45}$ heteroalkyl).

In some embodiments, where $R^{4a}$ is a linear or branched unsubstituted alkyl (e.g. branched unsubstituted $C_{10}$-$C_{50}$ alkyl), the alkyl is a saturated alkyl (e.g. a linear or branched unsubstituted saturated alkyl or branched unsubstituted $C_{10}$-$C_{50}$ saturated alkyl). A "saturated alkyl," as used herein, refers to an alkyl consisting only of hydrogen and carbon atoms and are bonded exclusively by single bonds. Thus, in some embodiments, $R^{4a}$ may be linear or branched unsubstituted saturated alkyl. In some embodiments, $R^{4a}$ is branched unsubstituted $C_{10}$-$C_{50}$ saturated alkyl. In other embodiments, $R^{4a}$ is linear unsubstituted $C_{10}$-$C_{50}$ saturated alkyl. In some embodiments, $R^{4a}$ is branched unsubstituted $C_{16}$-$C_{50}$ saturated alkyl. In other embodiments, $R^{4a}$ is linear unsubstituted $C_{16}$-$C_{50}$ saturated alkyl. In some embodiments, $R^{4a}$ is branched unsubstituted $C_{12}$-$C_{16}$ saturated alkyl. In other embodiments, $R^{4a}$ is linear unsubstituted $C_{12}$-$C_{16}$ saturated alkyl. In other embodiments, $R^{4a}$ is linear unsubstituted $C_{12}$-$C_{16}$ saturated alkyl. In other embodiments, $R^{4a}$ is branched unsubstituted $C_{12}$-$C_{16}$ saturated alkyl.

In some embodiments, $R^2$ is branched or linear unsubstituted $C_{10}$-$C_{50}$ alkyl or $R^{4a}$-substituted $C_{10}$-$C_{100}$ heteroalkyl, or $R^{4a}$-substituted phenyl. In other embodiments, $R^2$ is branched or linear unsubstituted $C_{14}$-$C_{50}$ alkyl, $R^{4a}$-substituted $C_{20}$-$C_{50}$ heteroalkyl, $(C_6H_5$—$CH_2CH_2)_3C_6H_2$—, $(C_6H_5$—$CH_2CH_2)_2C_6H_3$—, $(C_6H_5$—$CH_2CH_2)_1C_6H_4$—, or $R^{4a}$-substituted or unsubstituted naphthyl. In some embodiments, the naphthyl is a mono-, di-, or tri-alkyl naphthyl or any combination thereof. In some related embodiments, the alkyl is a saturated alkyl. In other related embodiments, z is as defined in an embodiment above (e.g. z is at least 25; or at least 35, e.g. 35 to 100).

In some embodiments, $R^2$ is $R^{4a}$-substituted phenyl. $R^{4a}$ may be $R^{5a}$-substituted or unsubstituted $C_1$-$C_{50}$ alkyl (e.g. $C_2$-$C_6$ alkyl). In some embodiments, $R^{4a}$ is $R^{5a}$-substituted ethyl. $R^{4a}$ may be branched $R^{5a}$-substituted $C_1$-$C_{50}$ alkyl (e.g. branched $C_2$-$C_6$ alkyl). In some embodiments, $R^{4a}$ is branched $R^{5a}$-substituted propyl. In some embodiments, $R^{5a}$ is $R^{6a}$-substituted or unsubstituted alkyl (e.g. unsubstituted methyl), $R^{6a}$-substituted or unsubstituted aryl (e.g. substituted or unsubstituted phenyl), or $R^{6a}$-substituted or unsubstituted cycloalkyl. In some further embodiments, $R^{8a}$ is independently unsubstituted $C_1$-$C_4$ alkyl (e.g. methyl) and $R^{6a}$-substituted aryl (e.g. $R^{6a}$-substituted phenyl). In some further embodiments, $R^{6a}$ is $R^{7a}$-substituted or unsubstituted alkyl or $R^{7a}$-substituted or unsubstituted cycloalkyl. In some embodiments, $R^2$ is having the formula:

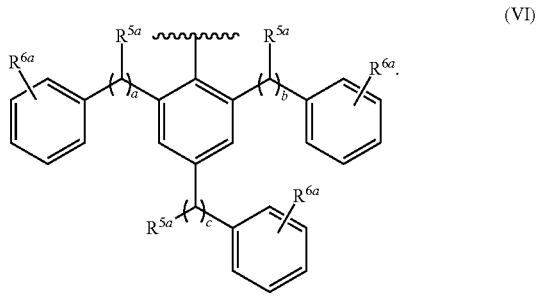

(VI)

In formula (VI), $R^{5a}$ and $R^{6a}$ are as defined above. For example, in some embodiments, $R^{5a}$ is independently $R^{6a}$-substituted or unsubstituted $C_1$-$C_{50}$ alkyl (e.g. a branched and/or saturated alkyl), $R^{6a}$-substituted or unsubstituted aryl or $R^{6a}$-substituted or unsubstituted cycloalkyl. In some embodiments, $R^{5a}$ is independently unsubstituted $C_1$-$C_{25}$ alkyl (e.g. a branched and/or saturated alkyl). In other embodiments, $R^{5a}$ is independently branched unsubstituted $C_1$-$C_{25}$ saturated alkyl. In some embodiments, $R^{6a}$ is independently $R^{7a}$-substituted or unsubstituted $C_1$-$C_{50}$ alkyl (e.g. a branched and/or saturated alkyl), $R^{7a}$-substituted or unsubstituted aryl or $R^{7a}$-substituted or unsubstituted cycloalkyl. $R^{7a}$ may be substituted or unsubstituted alkyl, substituted or unsubstituted heteroalkyl, substituted or unsubstituted aryl, or substituted or unsubstituted cycloalkyl. In some embodiments, $R^{6a}$ is independently $C_1$-$C_{25}$ alkyl. In other embodiments, $R^{6a}$ is branched unsubstituted $C_1$-$C_{25}$ saturated alkyl. The symbols a, b, and c are independently integers from 1 to 15. In some embodiments, a, b, and c are independently integers from 1 to 10. In some embodiments, a, b, and c are independently integers from 1 to 10. In some embodiments, a, b, and c are 1. Each $R^{5a}$ and $R^{6a}$ are optionally different.

In some embodiments, $R^3$ is independently hydrogen or unsubstituted $C_1$-$C_5$ alkyl. In some embodiments, $R^3$ is a branched unsubstituted $C_1$-$C_5$ saturated alkyl. In some embodiments, $R^3$ is hydrogen or unsubstituted $C_1$ or $C_2$ alkyl. In some related embodiments, $R^3$ is hydrogen or branched unsubstituted $C_1$ or $C_2$ saturated alkyl. In some embodiments, $R^3$ is hydrogen or a branched unsubstituted $C_1$ saturated alkyl. In other embodiments, $R^3$ is $C_2$-$C_6$ alkyl. In some embodiments, $R^3$ is a branched unsubstituted $C_2$-$C_6$ saturated alkyl. In some embodiments, $R^3$ is not $C_2$ alkyl. In other embodiments, $R^3$ is $C_1$ alkyl or $C_3$-$C_6$ alkyl. In some embodiments, $R^2$ is a branched unsubstituted $C_3$-$C_6$ saturated alkyl. In other embodiments, $R^3$ is hydrogen.

M may be a monovalent, divalent or trivalent cation. In some embodiments, $M^+$ is a monovalent, divalent or trivalent metal cation. In some embodiments, $M^+$ is a monovalent or divalent cation (e.g. metal cation). In some embodiments, $M^+$ is a monovalent cation (e.g. metal cation). In some embodiments, $M^+$ is a divalent cation (e.g. metal cation). In some embodiments, $M^+$ is $Na^+$, $K^+$, $NH_4^+$, $Ca^{+2}$, $Mg^{+2}$ or $Ba^{+2}$. A person having ordinary skill in the art will immediately recognize that $M^+$ may be a divalent cation where X is a monovalent anion (e.g. where $M^+$ is coordinated with more than one compound provided herein or with an additional anion in the surrounding liquid environment).

In some embodiments the compound of formula (I), or embodiments thereof disclosed herein (e.g. formula (II), (III), (IV), or (V)), the compound has a molecular weight of at least about 1500 g/mol. In some embodiments of the compound of formula (I), or embodiments thereof disclosed herein, the compound has a molecular weight of at least 1 about 600 g/mol. In some embodiments of the compound of formula (I), or embodiments thereof disclosed herein, the compound has a molecular weight of at least about 1700 g/mol. In some embodiments of the compound of formula (I), or embodiments thereof disclosed herein, the compound has a molecular weight of at least about 1800 g/mol. In some embodiments of the compound of formula (I), or embodiments thereof disclosed herein, the compound has a molecular weight of at least about 1900 g/mol. In some embodiments of the compound of formula (I), or embodiments thereof disclosed herein, the compound has a molecular weight of at least about 2000 g/mol. In some embodiments of the compound of formula (I), or embodiments thereof disclosed herein, the compound has a molecular weight of at least about 2100 g/mol. In some embodiments of the compound of formula (I), or embodiments thereof disclosed herein, the compound has a molecular weight of at least about 2200 g/mol. In some embodiments of the compound of formula (I), or embodiments thereof disclosed herein, the compound has a molecular weight of at least about 2300 g/mol. In some embodiments of the compound of formula (I), or embodiments thereof disclosed herein, the compound has a molecular weight of at least about 2400 g/mol. In some embodiments of the compound of formula (I), or embodiments thereof disclosed herein, the compound has a molecular weight of at least about 2500 g/mol. In some embodiments of the compound of formula (I), or embodiments thereof disclosed herein, the compound has a molecular weight of at least about 2600 g/mol. In some embodiments of the compound of formula (I), or embodiments thereof disclosed herein, the compound has a molecular weight of at least about 2700 g/mol. In some embodiments of the compound of formula (I), or embodiments thereof disclosed herein, the compound has a molecular weight of at least about 2800 g/mol. In some embodiments of the compound of formula (I), or embodiments thereof disclosed herein, the compound has a molecular weight of at least about 2900 g/mol. In some embodiments of the compound of formula (I), or embodiments thereof disclosed herein, the compound has a molecular weight of at least about 3000 g/mol.

In some embodiments, where multiple $R^3$ substituents are present and at least two $R$ substituents are different, $R^3$ substituents with the fewest number of carbons are present to the side of the compound of formula (I) bound to the X substituent. In this embodiment, the compound of formula (I) will be increasingly hydrophilic in progressing from the $R^2$ substituent to the side of the compound of formula (I) bound to the X substituent. The term "side of the compound of formula (I) bound to the X substituent" refers to the side of the compound indicated by asterisks in the below structures:

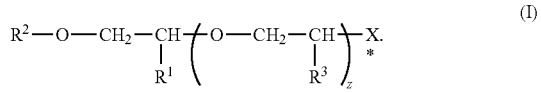
(I)

In some embodiments of the compound of formula (I), or embodiments thereof provided herein, where $R^1$ is unsubstituted $C_{10}$-$C_{25}$ alkyl and $R^2$ is linear unsubstituted $C_{12}$-$C_{25}$ alkyl, the symbol z is an integer from 15 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 20 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 25 to 100. In other embodiments, where $R^1$ is unsubstituted $C_{10}$-$C_{25}$ alkyl and $R^2$ is linear s unsubstituted $C_{12}$-$C_{25}$ alkyl, the symbol z is an integer from 30 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 35 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 40 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 45 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 50 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 55 to 100. In other embodiments, where $R^1$ is unsubstituted $C_{10}$-$C_{25}$ alkyl and $R^2$ is linear unsubstituted $C_{12}$-$C_{25}$ alkyl, the symbol z is an integer from 60 to 100.

In some embodiments of the compound of formula (I), or embodiments thereof provided herein, where $R^1$ is unsubstituted $C_{10}$-$C_{25}$ alkyl and $R^2$ is branched unsubstituted $C_{30}$-$C_{50}$ alkyl, the symbol z is an integer from 15 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 20 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 25 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 30 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 35 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 40 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 45 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 50 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 55 to 100. In other embodiments, where $R^1$ is unsubstituted $C_{10}$-$C_{25}$ alkyl and $R^2$ is branched unsubstituted $C_{30}$-$C_{50}$ alkyl, the symbol z is an integer from 60 to 100.

In some embodiments of the compound of formula (I), or embodiments thereof provided herein, where $R^1$ is unsubstituted $C_{10}$-$C_{25}$ alkyl and $R^2$ is $R^{4a}$-substituted phenyl, the symbol z is an integer from 15 to 100. In other embodiments, where $R^1$ is unsubstituted $C_{10}$-$C_{25}$ alkyl and $R^2$ is $R^{4a}$-substituted phenyl, the symbol z is an integer from 20 to 100. In other embodiments, where $R^1$ is unsubstituted $C_{10}$-$C_{25}$ alkyl and $R^2$ is $R^{4a}$-substituted phenyl, the symbol z is an integer from 25 to 100. In other embodiments, where $R^1$ is unsubstituted $C_{10}$-$C_{25}$ alkyl and $R^2$ is $R^{4a}$-substituted phenyl, the symbol z is an integer from 30 to 100. In other embodiments, where $R^1$ is unsubstituted $C_{10}$-$C_{25}$ alkyl and $R^2$ is $R^{4a}$-substituted phenyl, the symbol z is an integer from 35 to 100. In other embodiments, where $R^1$ is unsubstituted $C_{10}$-$C_{25}$ alkyl and $R^2$ is $R^{4a}$-substituted phenyl, the symbol z is an integer from 40 to 100. In other embodiments, where $R^1$ is unsubstituted $C_{10}$-$C_{25}$ alkyl and $R^2$ is $R^{4a}$-substituted phenyl, the symbol z is an integer from 45 to 100. In other embodiments, where $R^1$ is unsubstituted $C_{10}$-$C_{25}$ alkyl and $R^2$ is $R^{4a}$-substituted phenyl, the symbol z is an integer from 50 to 100. In other embodiments, where $R^1$ is unsubstituted $C_{10}$-$C_{25}$ alkyl and $R^2$ is $R^{4a}$-substituted phenyl, the symbol z is an integer from 55 to 100. In other embodiments, where $R^1$ is unsubstituted $C_{10}$-$C_{25}$ alkyl and $R^2$ is $R^{4a}$-substituted phenyl, the symbol z is an integer from 60 to 100.

In some embodiments of the compound of formula (I), or embodiments thereof provided herein, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 5 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 10 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 12 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 14 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 16 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 18 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 20 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 22 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 24 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 26 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 28 to 50. In other embodiments, where $R^1$ is unsubstituted $C_{10}$-$C_{25}$ alkyl and $R^2$ is $R^{4a}$-substituted $C_{20}$-$C_{100}$ heteroalkyl, the symbol z is an integer from 30 to 50.

In some embodiments, the compound has the formula

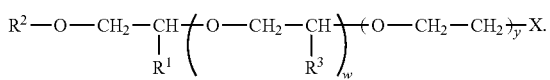
(II)

In formula (II) $R^1$, $R^2$, X is defined as above (e.g. in formula (I)). $R^3$ is independently unsubstituted $C_1$-$C_6$ alkyl, the symbol y is an integer from 1 to 50 and w is an integer from 0 to 60. In some embodiments, $R^3$ is independently unsubstituted $C_1$-$C_4$ alkyl. In some embodiments, $R^2$ is unsubstituted tristyrylphenyl. In some embodiments, $R^3$ is unsubstituted $C_1$-$C_3$ alkyl. In other embodiments, $R^3$ is methyl. In other embodiments, $R^3$ is ethyl. In some embodiments, $R^3$ is independently methyl or ethyl. In some embodiments, y is an integer from 5 to 100 and w is an integer from 0 to 100.

In some embodiments, y is 5 to 90. In some related embodiments, y is 5 to 80. In some related embodiments, y is 5 to 70. In some related embodiments, y is 5 to 60. In some related embodiments, y is 5 to 50. In some related embodiments, y is 5 to 40. In some related embodiments, y is 5 to 30. In some related embodiments, y is 10 to 25. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 10 to 90. In some related embodiments, y is 10 to 80. In some related embodiments, y is 10 to 70. In some related embodiments, y is 10 to 60. In some related embodiments, y is 10 to 50. In some related embodiments, y is 10 to 40. In some related embodiments, y is 10 to 30. In some related embodiments, y is 10 to 25. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 15 to 90. In some related embodiments, y is 15 to 80. In some related embodiments, y is 15 to 70. In some related embodiments, y is 15 to 60. In some related embodiments, y is 15 to 50. In some related embodiments, y is 15 to 40. In some related embodiments, y is 15 to 30. In some related embodiments, y is 15 to 25. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 20 to 90. In some related embodiments, y is 20 to 80. In some related embodiments, y is 20 to 70. In some related embodiments, y is 20 to 60. In some related embodiments, y is 20 to 50. In some related embodiments, y is 20 to 40. In some related embodiments, y is 20 to 30. In some related embodiments, y is 20 to 25. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 25 to 90. In some related embodiments, y is 25 to 80. In some related embodiments, y is 25 to 70. In some related embodiments, y is 25 to 60. In some related embodiments, y is 25 to 50. In some related embodiments, y is 25 to 40. In some related embodiments, y is 25 to 30. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 30 to 90. In some related embodiments, y is 30 to 80. In some related embodiments, y is 30 to 70. In some related embodiments, y is 30 to 60. In some related embodiments, y is 30 to 50. In some related embodiments, y is 30 to 40. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 35 to 90. In some related embodiments, y is 35 to 80. In some related embodiments, y is 35 to 70. In some related embodiments, y is 35 to 60.

In some related embodiments, y is 35 to 50. In some related embodiments, y is 35 to 40. In some further related embodiments, w is 0 to 90. In some further related embodiments, w is 10 to 80. In some further related embodiments, w is 20 to 70. In some further related embodiments, w is 30 to 60. In some further related embodiments, w is 40 to 50. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other still further related embodiments, w is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In other embodiments, the compound has the formula

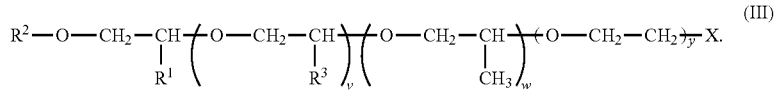
(III)

In formula (III) $R^1$, $R^2$, X is defined as above (e.g. in formula (I), and (II)). $R^3$ is independently unsubstituted $C_2$-$C_6$ alkyl. In some embodiments, $R^3$ is independently unsubstituted $C_2$-$C_4$ alkyl. In some embodiments, $R^3$ is ethyl. The symbol y is an integer from 1 to 30 w is an integer from 0 to 30 and v is an integer from 0 to 30.

In some embodiments, y is 5 to 90. In some related embodiments, y is 5 to 80. In some related embodiments, y is 5 to 70. In some related embodiments, y is 5 to 60. In some related embodiments, y is 5 to 50. In some related embodiments, y is 5 to 40. In some related embodiments, y is 5 to 30. In some further related embodiments, y is 10 to 25. In some further related embodiments, w is 0 to 60. In some further related embodiments, w is 5 to 50. In some further related embodiments, w is 10 to 40. In some further related embodiments, w is 15 to 30. In some further related embodiments, w is 20 to 30. In some further related embodiments, w is 25 to 30. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other further related embodiments, w is 10 to 15. In other still related embodiments, v is 0 to 60. In other still related embodiments, v is 5 to 50. In other still related embodiments, v is 10 to 40. In other still related embodiments, v is 15 to 30. In other still related embodiments, v is 20 to 30. In other still related embodiments, v is 25 to 30. In other still related embodiments, v is 0 to 30. In other still related embodiments, v is 0 to 20. In other still related embodiments, v is 0 to 10. In other still related embodiments, v is more than 5. Moreover, in still further related embodiments, v is 0. In other still related embodiments, v is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 10 to 90. In some related embodiments, y is 10 to 80. In related some embodiments, y is 10 to 70. In some embodiments, y is 10 to 60. In some related embodiments, y is 10 to 50. In some related embodiments, y is 10 to 40. In some related embodiments, y is 10 to 30. In some related embodiments, y is 10 to 25. In some further related embodiments, w is 0 to 60. In some further related embodiments, w is 5 to 50. In some further related embodiments, w is 10 to 40. In some further related embodiments, w is 15 to 30. In some further related embodiments, w is 20 to 30. In some further related embodiments, w is 25 to 30. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other further related embodiments, w is 10 to 15. In other still related embodiments, v is 0 to 60. In other still related embodiments, v is 5 to 50. In other still related embodiments, v is 10 to 40. In other still related embodiments, v is 15 to 30. In other still related embodiments, v is 20 to 30. In other still related embodiments, v is 25 to 30. In other still related embodiments, v is 0 to 30. In other still related embodiments, v is 0 to 20. In other still related embodiments, v is 0 to 10. In other still related embodiments, v is more than 5. Moreover, in still further related embodiments, v is 0. In other still related embodiments, v is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 15 to 90. In some related embodiments, y is 15 to 80. In some related embodiments, y is 15 to 70. In some related embodiments, y is 15 to 60. In some related embodiments, y is 15 to 50. In some related embodiments, y is 15 to 40. In some related embodiments, y is 15 to 30. In some further related embodiments, w is 0 to 60. In some further related embodiments, w is 5 to 50. In some further related embodiments, w is 10 to 40. In some further related embodiments, w is 15 to 30. In some further related embodiments, w is 20 to 30. In some further related embodiments, w is 25 to 30. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other further related embodiments, w is 10 to 15. In other still related embodiments, v is 0 to 60. In other still related embodiments, v is 5 to 50. In other still related embodiments, v is 10 to 40. In other still related embodiments, v is 15 to 30. In other still related embodiments, v is 20 to 30. In other still related embodiments, v is 25 to 30. In other still related embodiments, v is 0 to 30. In other still related embodiments, v is 0 to 20. In other still related embodiments, v is 0 to 10. In other still related embodiments, v is more than 5. Moreover, in still further related embodiments, v is 0. In other still related embodiments, v is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 20 to 90. In some related embodiments, y is 20 to 80. In some related embodiments, y is 20 to 70. In some related embodiments, y is 20 to 60. In some related embodiments, y is 20 to 50. In some related embodiments, y is 20 to 40. In some related embodiments, y is 20 to 30. In some related embodiments, y is 25 to 30. In some further related embodiments, w is 0 to 60. In some further related embodiments, w is 5 to 50. In some further related embodiments, w is 10 to 40. In some further related embodiments, w is 15 to 30. In some further related embodiments, w is 20 to 30. In some further related embodiments, w is 25 to 30. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other further related embodiments, w is 10 to 15. In other still related embodiments, v is 0 to 60. In other still related embodiments, v is 5 to 50. In other still related embodiments, v is 10 to 40. In other still related embodiments, v is 15 to 30. In other still related embodiments, v is 20 to 30. In other still related embodiments, v is 25 to 30. In other still related embodiments, v is 0 to 30. In other still related embodiments, v is 0 to 20. In other still related embodiments, v is 0 to 10. In other still related embodiments, v is more than 5. Moreover, in still further related embodiments, v is 0. In other still related embodiments, v is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, y is 25 to 90. In some related embodiments, y is 25 to 80. In some related embodiments, y is 25 to 70. In some related embodiments, y is 25 to 60. In some related embodiments, y is 25 to 50. In some related embodiments, y is 25 to 40. In some related embodiments, y is 25 to 30. In some further related embodiments, w is 0 to 60. In some further related embodiments, w is 5 to 50. In some further related embodiments, w is 10 to 40. In some further related embodiments, w is 15 to 30. In some further related embodiments, w is 20 to 30. In some further related embodiments, w is 25 to 30. In some further related embodiments, w is 0 to 30. In some further related embodiments, w is 0 to 20. In some further related embodiments, w is 0 to 10. In other further related embodiments, w is more than 10. Moreover, in still further related embodiments, w is 0. In other further related embodiments, w is 10 to 15. In other still related embodiments, v is 0 to 60. In other still related embodiments, v is 5 to 50. In other still related embodiments, v is 10 to 40. In other still related embodiments, v is 15 to 30. In other still related embodiments, v is 20 to 30. In other still related embodiments, v is 25 to 30. In other still related embodiments, v is 0 to 30. In other still related embodiments, v is 0 to 20. In other still related embodiments, v is 0 to 10. In other still related embodiments, v is more than 5. Moreover, in still further related embodiments, v is 0. In other still related embodiments, v is 10 to 15. $R^1$ and $R^2$ may be any of the embodiments described above (e.g. $R^1$ maybe linear unsubstituted $C_{12}$-$C_{20}$ alkyl, $R^2$ maybe linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl).

In some embodiments, the compound has the formula:

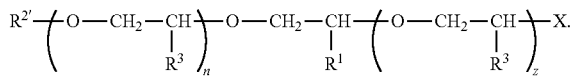

(IV)

In formula (IV) $R^1$, $R^3$, X is defined as above (e.g. in formula (I) and (II)). For example, $R^1$ is linear unsubstituted $C_{12}$-$C_{20}$ alkyl, $R^3$ is independently hydrogen, methyl or ethyl, and the symbol z is an integer from 5 to 50. $R^{2'}$ is linear unsubstituted $C_{10}$-$C_{60}$ alkyl, $R^3$ is independently hydrogen or unsubstituted $C_1$-$C_4$ alkyl, n is an integer from 0 to 50 and z is an integer from 5 to 25. In some embodiments, $R^3$ is independently hydrogen or methyl.

In some embodiments, z is 5 to 50. In some related embodiments, z is 5 to 45. In some related embodiments, z is 5 to 40. In some related embodiments, z is 5 to 35. In some related embodiments, z is 5 to 30. In some related embodiments, z is 5 to 25. In some related embodiments, z is 5 to 20. In some further related embodiments, n is 0 to 50. In some further related embodiments, n is 5 to 45. In some other further related embodiments, n is 7. In some further related embodiments, n is 10 to 40. In some other further related embodiments, n is 15 to 35. In some further related embodiments, n is 15 to 20. In some further related embodiments, n is 20 to 30. In other further related embodiments, n is 5, 7, or 15. In some further related embodiments n is 0. $R^1$ and $R^3$ may be any of the embodiments described above (e.g. $R^1$ may be linear unsubstituted $C_{12}$-$C_{20}$ alkyl and $R^3$ is independently hydrogen, methyl or ethyl).

In some embodiments, z is 10 to 50. In some related embodiments, z is 10 to 45. In some related embodiments, z is 10 to 40. In some related embodiments, z is 10 to 35. In some related embodiments, z is 10 to 30. In some related embodiments, z is 10 to 25. In some related embodiments, z is 10 to 20. In some further related embodiments, n is 0 to 50. In some further related embodiments, n is 5 to 45. In some other further related embodiments, n is 7. In some further related embodiments, n is 10 to 40. In some other further related embodiments, n is 15 to 35. In some further related embodiments, n is 15 to 20. In some further related embodiments, n is 20 to 30. In other further related embodiments, n is 5, 7, or 15. In some further related embodiments, n is 0. $R^1$ and $R^3$ may be any of the embodiments described above (e.g. $R^1$ may be linear unsubstituted $C_{12}$-$C_{20}$ alkyl and $R^3$ is independently hydrogen, methyl or ethyl).

In some embodiments, z is 15 to 50. In some related embodiments, z is 15 to 45. In some related embodiments, z is 15 to 40. In some related embodiments, z is 15 to 35. In some related embodiments, z is 15 to 30. In some related embodiments, z is 15 to 25. In some related embodiments, z is 15 to 20. In some further related embodiments, n is 0 to 50. In some further related embodiments, n is 5 to 45. In some other further related embodiments, n is 7. In some further related embodiments, n is 10 to 40. In some other further related embodiments, n is 15 to 35. In some further related embodiments, n is 15 to 20. In some further related embodiments, n is 20 to 30. In other further related embodiments, n is 5, 7, or 15. In some further related embodiments, n is 0. $R^1$ and $R^3$ may be any of the embodiments described above (e.g. $R^1$ may be linear unsubstituted $C_{12}$-$C_{20}$ alkyl and $R^3$ is independently hydrogen, methyl or ethyl).

In some embodiments, z is 20 to 50. In some related embodiments, z is 20 to 45. In some related embodiments, z is 20 to 40. In some related embodiments, z is 20 to 35. In some related embodiments, z is 20 to 30. In some related embodiments, z is 20 to 25. In some further related embodiments, n is 0 to 50. In some further related embodiments, n is 5 to 45. In some other further related embodiments, n is 7. In some further related embodiments, n is 10 to 40. In some other further related embodiments, n is 15 to 35. In further related embodiments, n is 15 to 20. In some further related embodiments, n is 20 to 30. In other further related embodiments, n is 5, 7, or 15. In some further related embodiments, n is 0. $R^1$ and $R^3$ may be any of the embodiments described above (e.g. $R^1$ may be linear unsubstituted $C_{12}$-$C_{20}$ alkyl and $R^3$ is independently hydrogen, methyl or ethyl).

In some embodiments, z is 25 to 50. In some related embodiments, z is 25 to 45. In some related embodiments, z is 25 to 40. In some related embodiments, z is 25 to 35. In some related embodiments, z is 25 to 30. In some further related embodiments, n is 0 to 50. In some further related embodiments, n is 5 to 45. In some other further related embodiments, n is 7. In some further related embodiments, n is 10 to 40. In some other further related embodiments, n is 15 to 35. In further related embodiments, n is 15 to 20. In some further related embodiments, n is 20 to 30. In other further related embodiments, n is 5, 7, or 15. In some further related embodiments, n is 0. $R^1$ and $R^3$ may be any of the embodiments described above (e.g. $R^1$ may be linear unsubstituted $C_{12}$-$C_{20}$ alkyl and $R^3$ is independently hydrogen, methyl or ethyl).

$R^{2'}$ may be linear or branched unsubstituted alkyl. In some embodiments, $R^{2'}$ is branched unsubstituted $C_8$-$C_{40}$ alkyl. In other embodiments, $R^{2'}$ is linear unsubstituted $C_8$-$C_{40}$ alkyl. In some embodiments, $R^{2'}$ is branched unsubstituted $C_{10}$-$C_{40}$ alkyl. In other embodiments, $R^{2'}$ is linear unsubstituted $C_{10}$-$C_{40}$ alkyl. In some embodiments, $R^{2'}$ is branched unsubstituted $C_{12}$-$C_{40}$ alkyl. In other embodiments, $R^{2'}$ is linear unsubstituted $C_{12}$-$C_{40}$ alkyl. In some embodiments, $R^{2'}$ is branched unsubstituted $C_{14}$-$C_{40}$ alkyl. In other embodiments, $R^{2'}$ is linear unsubstituted $C_{14}$-$C_{40}$ alkyl. In some embodiments, $R^{2'}$ is branched unsubstituted $C_{16}$-$C_{40}$ alkyl. In other embodiments, $R^{2'}$ is linear unsubstituted $C_{16}$-$C_{40}$ alkyl. In some embodiments, $R^{2'}$ is branched unsubstituted $C_{18}$-$C_{40}$ alkyl. In other embodiments, $R^{2'}$ is linear unsubstituted $C_{18}$-$C_{40}$ alkyl. In some embodiments, $R^{2'}$ is branched unsubstituted $C_{20}$-$C_{40}$ alkyl. In other embodiments, $R^{2'}$ is linear unsubstituted $C_{20}$-$C_{40}$ alkyl. In some embodiments, $R^{2'}$ is branched unsubstituted $C_{22}$-$C_{40}$ alkyl. In other embodiments, $R^{2'}$ is linear unsubstituted $C_{22}$-$C_{40}$ alkyl. In some embodiments, $R^{2'}$ is branched unsubstituted $C_{24}$-$C_{40}$ alkyl. In other embodiments, $R^{2'}$ is linear unsubstituted $C_{24}$-$C_{40}$ alkyl. In some embodiments, $R^{2'}$ is branched unsubstituted $C_{26}$-$C_{40}$ alkyl. In other embodiments, $R^{2'}$ is linear unsubstituted $C_{26}$-$C_{40}$ alkyl. In some embodiments, $R^{2'}$ is branched unsubstituted $C_{28}$-$C_{40}$ alkyl. In other embodiments, $R^{2'}$ is linear unsubstituted $C_{28}$-$C_{40}$ alkyl. In some embodiments, $R^{2'}$ is branched unsubstituted $C_{30}$-$C_{40}$ alkyl. In other embodiments, $R^{2'}$ is linear unsubstituted $C_{30}$-$C_{40}$ alkyl. In some embodiments, $R^{2'}$ is branched unsubstituted $C_{32}$-$C_{40}$ alkyl. In other embodiments, $R^{2'}$ is linear unsubstituted $C_{32}$-$C_{40}$ alkyl. In some embodiments, $R^{2'}$ is branched unsubstituted $C_{34}$-$C_{40}$ alkyl. In other embodiments, $R^{2'}$ is linear unsubstituted $C_{34}$-$C_{40}$ alkyl.

In some embodiments, $R^{2'}$ is branched unsubstituted $C_8$-$C_{30}$ alkyl. In other embodiments, $R^{2'}$ is linear unsubstituted $C_8$-$C_{30}$ alkyl. In some embodiments, $R^{2'}$ is branched unsubstituted $C_{10}$-$C_{30}$ alkyl. In other embodiments, $R^{2'}$ is linear unsubstituted $C_{10}$-$C_{30}$ alkyl. In some embodiments, $R^{2'}$ is branched unsubstituted $C_{12}$-$C_{30}$ alkyl. In other embodiments, $R^{2'}$ is linear unsubstituted $C_{12}$-$C_{30}$ alkyl. In some embodiments, $R^{2'}$ is branched unsubstituted $C_{14}$-$C_{30}$ alkyl. In other embodiments, $R^{2'}$ is linear unsubstituted $C_{14}$-$C_{30}$ alkyl. In some embodiments, $R^{2'}$ is branched unsubstituted $C_{16}$-$C_{30}$ alkyl. In other embodiments, $R^{2'}$ is linear unsubstituted $C_{16}$-$C_{30}$ alkyl. In some embodiments, $R^{2'}$ is branched unsubstituted $C_{18}$-$C_{30}$ alkyl. In other embodiments, $R^{2'}$ is linear unsubstituted $C_{18}$-$C_{30}$ alkyl. In some embodiments, $R^{2'}$ is branched unsubstituted $C_{20}$-$C_{30}$ alkyl. In other embodiments, $R^{2'}$ is linear unsubstituted $C_{20}$-$C_{30}$ alkyl. In some embodiments, $R^{2'}$ is branched unsubstituted $C_{22}$-$C_{30}$ alkyl. In other embodiments, $R^{2'}$ is linear unsubstituted $C_{22}$-$C_{30}$ alkyl. In some embodiments, $R^{2'}$ is branched unsubstituted $C_{24}$-$C_{30}$ alkyl. In other embodiments, $R^{2'}$ is linear unsubstituted $C_{24}$-$C_{30}$ alkyl. In some embodiments, $R^{2'}$ is branched unsubstituted $C_{26}$-$C_{30}$ alkyl. In other embodiments, $R^{2'}$ is linear unsubstituted $C_{26}$-$C_{30}$ alkyl. In some embodiments, $R^{2'}$ is branched unsubstituted $C_{28}$-$C_{30}$ alkyl. In other embodiments, $R^{2'}$ is linear unsubstituted $C_{28}$-$C_{30}$ alkyl.

In some embodiments, where $R^{2'}$ is a linear or branched unsubstituted alkyl (e.g. branched unsubstituted $C_{10}$-$C_{50}$ alkyl), the alkyl is a saturated alkyl (e.g. a linear or branched unsubstituted saturated alkyl or branched unsubstituted $C_{10}$-$C_{50}$ saturated alkyl). A "saturated alkyl," as used herein, refers to an alkyl consisting only of hydrogen and carbon atoms and are bonded exclusively by single bonds. Thus, in some embodiments, $R^{2'}$ may be linear or branched unsubstituted saturated alkyl. In some embodiments, $R^{2'}$ is branched unsubstituted $C_{10}$-$C_{50}$ saturated alkyl. In other embodiments, $R^{2'}$ is linear unsubstituted $C_{10}$-$C_{50}$ saturated alkyl. In some embodiments, $R^{2'}$ is branched unsubstituted $C_{16}$-$C_{50}$ saturated alkyl. In other embodiments, $R^{2'}$ is linear unsubstituted $C_{16}$-$C_{50}$ saturated alkyl. In some embodiments, $R^{2'}$ is branched unsubstituted $C_{12}$-$C_{16}$ saturated alkyl. In other embodiments, $R^{2'}$ is linear unsubstituted $C_{12}$-$C_{16}$ saturated alkyl. In other embodiments, $R^{2'}$ is linear unsubstituted $C_{12}$-$C_{16}$ saturated alkyl. In other embodiments, $R^{2'}$ is branched unsubstituted $C_{12}$-$C_{16}$ saturated alkyl.

In some embodiments, the compound has the formula:

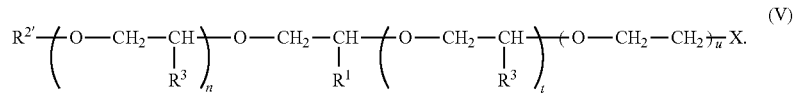

$$R^{2'}\!\!\left(\!\!O\!-\!CH_2\!-\!\underset{R^3}{\overset{|}{CH}}\!\!\right)_{\!\!n}\!\!O\!-\!CH_2\!-\!\underset{R^1}{\overset{|}{CH}}\!\!\left(\!\!O\!-\!CH_2\!-\!\underset{R^3}{\overset{|}{CH}}\!\!\right)_{\!\!t}\!\!\left(\!\!O\!-\!CH_2\!-\!CH_2\!\!\right)_{\!\!u}\!\!X. \quad (V)$$

In formula (V) $M^+$, $R^1$, $R^{2'}$ and $R^3$ are as defined above (e.g. in formula (I), (II), (III), and (IV)). For example, $R^1$ is linear unsubstituted $C_{12}$-$C_{20}$ alkyl, $R^{2'}$ is linear unsubstituted $C_{10}$-$C_{60}$ alkyl, $R^3$ is independently hydrogen or $C_1$-$C_4$ alkyl, and the symbol n is an integer from 0 to 50. In some embodiments, $R^3$ is independently methyl or ethyl, n is an integer from 0 to 50, t is an integer from 0 to 30 and u is an integer from 5 to 30.

In some embodiments, the symbol u is an integer from 5 to 50. In some related embodiments, u is 5 to 45. In some related embodiments, u is 5 to 40. In some related embodiments, u is 5 to 35. In some related embodiments, u is 5 to 30. In some related embodiments, u is 5 to 25. In some related embodiments, u is 5 to 20. In some further related embodiments, t is 0 to 30. In some further related embodiments, t is 5 to 25. In some further related embodiments, t is 10 to 20. In some further related embodiments, t is 15 to 20. In some further related embodiments, t is 0. In some further related embodiments, t is more than 5. In other still related embodiments, n is 0 to 50. In other still related embodiments, n is 5 to 45. In other still related embodiments, n is 10 to 40. In other still related embodiments, n is 15 to 35. In other still related embodiments, n is 20 to 30. In other still related embodiments, n is 25 to 30. In other still related embodiments, n is 0. In other still related embodiments, n is more than 5, 15, or 20. $R^1$, $R^{2'}$ and $R^3$ may be any of the embodiments described above (e.g. $R^1$ and $R^{2'}$ may be independently linear unsubstituted $C_{12}$-$C_{20}$ alkyl and $R^3$ is independently hydrogen, methyl or ethyl).

In some embodiments, the symbol u is an integer from 10 to 50. In some related embodiments, u is 10 to 45. In some related embodiments, u is 10 to 40. In some related embodiments, u is 10 to 35. In some related embodiments, u is 10 to 30. In some related embodiments, u is 10 to 25. In some related embodiments, u is 10 to 20. In some further related embodiments, t is 0 to 30. In some further related embodiments, t is 5 to 25. In some further related embodiments, t is 10 to 20. In some further related embodiments, t is 15 to 20. In some further related embodiments, t is 0. In some further related embodiments, t is more than 5. In other still related embodiments, n is 0 to 50. In other still related embodiments, n is 5 to 45. In other still related embodiments, n is 10 to 40. In other still related embodiments, n is 15 to 35. In other still related embodiments, n is 20 to 30. In other still related embodiments, n is 25 to 30. In other still related embodiments, n is 0. In other still related embodiments, n is more than 5, 15, or 20. $R^1$, $R^{2'}$ and $R^3$ may be any of the embodiments described above (e.g. $R^1$ and $R^{2'}$ may be independently linear unsubstituted $C_{12}$-$C_{20}$ alkyl and $R^3$ is independently hydrogen, methyl or ethyl).

In some embodiments, the symbol u is an integer from 15 to 50. In some related embodiments, u is 15 to 45. In some related embodiments, u is 15 to 40. In some related embodiments, u is 15 to 35. In some related embodiments, u is 15 to 30. In some related embodiments, u is 15 to 25. In some related embodiments, u is 15 to 20. In some further related embodiments, t is 0 to 30. In some further related embodiments, t is 5 to 25. In some further related embodiments, t is 10 to 20. In some further related embodiments, t is 15 to 20. In some further related embodiments, t is 0. In some further related embodiments, t is more than 5. In other still related embodiments, n is 0 to 50. In other still related embodiments, n is 5 to 45. In other still related embodiments, n is 10 to 40. In other still related embodiments, n is 15 to 35. In other still related embodiments, n is 20 to 30. In other still related embodiments, n is 25 to 30. In other still related embodiments, n is 0. In other still related embodiments, n is more than 5, 15, or 20. $R^1$, $R^{2'}$ and $R^3$ may be any of the embodiments described above (e.g. $R^1$ and $R^{2'}$ may be independently linear unsubstituted $C_{12}$-$C_{20}$ alkyl and $R^3$ is independently hydrogen, methyl or ethyl).

In some embodiments, the symbol u is an integer from 20 to 50. In some related embodiments, u is 20 to 45. In some related embodiments, u is 20 to 40. In some related embodiments, u is 20 to 35. In some related embodiments, u is 20 to 30. In some related embodiments, u is 20 to 25. In some further related embodiments, t is 0 to 30. In some further related embodiments, t is 5 to 25. In some further related embodiments, t is 10 to 20. In some further related embodiments, t is 15 to 20. In some further related embodiments, t is 0. In some further related embodiments, t is more than 5. In other still related embodiments, n is 0 to 50. In other still related embodiments, n is 5 to 45. In other still related embodiments, n is 10 to 40. In other still related embodiments, n is 15 to 35. In other still related embodiments, n is 20 to 30. In other still related embodiments, n is 25 to 30. In other still related embodiments, n is 0. In other still related embodiments, n is more than 5, 15, or 20. $R^1$, $R^{2'}$ and $R^3$ may be any of the embodiments described above (e.g. $R^1$ and $R^{2'}$ may be independently linear unsubstituted $C_{12}$-$C_{20}$ alkyl and $R^3$ is independently hydrogen, methyl or ethyl).

III. Methods

In another aspect, an aqueous composition is provided including a co-surfactant and a compound described herein (e.g. a compound of formula (I), (II), (III), (IV), or (V)). A co-surfactant, as used herein, is a compound within the aqueous composition that functions as a surface active agent when the aqueous composition is in contact with a crude oil (e.g. an unrefined petroleum). The co-surfactant, along with the compound of formula (I), (II), (III), (IV), or (V), may act to lower the interfacial tension and/or surface tension of the unrefined petroleum. In some embodiments, the co-surfactant and the compound of formula (I), (II), (III), (IV), or (V) are present in synergistic surface active amounts. A "synergistic surface active amount," as used herein, means that a compound of formula (I), (II), (III), (IV), or (V) and the co-surfactant are present in amounts in which the oil surface activity (interfacial tension lowering effect and/or surface tension lowering effect on crude oil when the aqueous composition is added to the crude oil) of the compound and co-surfactant combined is greater than the additive oil surface activity of the co-surfactant individually and the compound individually. In some cases, the oil surface activity of the compound and co-surfactant combination is 10%, 20%, 30%, 40%, 50%, 60%, 70%, 80%, 90% or 100% more than the additive oil surface activity of the co-surfactant individually and the compound individually. In some embodiments, the oil surface activity of the compound and co-surfactant combination is 2, 3, 4, 5, 6, 7, 8, 9 or 10 times more than the additive oil surface activity of the co-surfactant individually and the compound individually.

In another embodiment, the compound and co-surfactant are present in a surfactant stabilizing amount. A "surfactant stabilizing amount" means that the compound and the co-surfactant are present in an amount in which the co-surfactant degrades at a slower rate in the presence of the compound than in the absence of the compound, and/or the compound degrades at a slower rate in the presence of the co-surfactant than in the absence of the compound. The rate of degradation may be 10%, 20%, 30%, 40%, 50%, 60%, 70%, 80%, 90% or 100% slower. In some embodiments, the rate of degradation is 2, 3, 4, 5, 6, 7, 8, 9 or 10 times slower.

In another embodiment, the compound and co-surfactant are present in a synergistic solubilizing amount. A "synergistic solubilizing amount" means that the compound and the co-surfactant are present in an amount in which the compound is more soluble in the presence of the co-surfactant than in the absence of the surfactant, and/or the co-surfactant is more soluble in the presence of the compound than in the absence of the compound. The solubilization may be 10%, 20%, 30%, 40%, 50%, 60%, 70%, 80%, 90% or 100% higher. In some embodiment, the solubilization is 2, 3, 4, 5, 6, 7, 8, 9 or 10 times higher. In some embodiments, the compound is present in an amount sufficient to increase the solubility of the co-surfactant in the aqueous composition relative to the absence of the compound. In other words, in the presence of a sufficient amount of the compound, the solubility of the co-surfactant in the aqueous composition is higher than in the absence of the compound. In other embodiments, the co-surfactant is present in an amount sufficient to increase the solubility of the compound in the aqueous composition relative to the absence of the co-surfactant. Thus, in the presence of a sufficient amount of the co-surfactant the solubility of the compound in the aqueous solution is higher than in the absence of the co-surfactant.

In some embodiments, a single type of co-surfactant is in the aqueous composition. In other embodiments, a plurality of co-surfactant types is in the aqueous composition. In some embodiments, the co-surfactant is an anionic surfactant, a non-ionic surfactant, a zwitterionic surfactant or a cationic surfactant. In some embodiments, the co-surfactant is an anionic surfactant, a non-ionic surfactant or a cationic surfactant. In other embodiments, the co-surfactant is an zwitterionic co-surfactant. "Zwitterionic" or "zwitterion" as used herein refers to a neutral molecule with a positive (or cationic) and a negative (or anionic) electrical charge at different locations within the same molecule. Examples for zwitterionics are without limitation betains and sultains.

The co-surfactant as provided herein may be a combination of one or more anionic, non-ionic, cationic or zwitterionic co-surfactants. In some embodiments, the co-surfactant is an internal olefin sulfonate (IOS), an alfa olefin sulfonate (AOS), an alkyl aryl sulfonate (ARS), an alkane sulfonate, a petroleum sulfonate, an alkyl diphenyl oxide (di)sulfonate, an alcohol sulfate, an alkoxy sulfate, an alkoxy sulfonate, an alcohol phosphate, an alkoxy phosphate, a sulfosuccinate ester, an alcohol ethoxylate, an alkyl phenol ethoxylate, a quaternary ammonium salt, a betaine or sultaine. The co-surfactant as provided herein, may also be a soap.

Without limitation, the co-surfactant may be a combination of two or more of the following compounds: an internal olefin sulfonate (IOS), an alfa olefin sulfonate (AOS), an alkyl aryl sulfonate (ARS) (e.g. an alkyl benzene sulfonate (ABS)), an alkane sulfonate, a petroleum sulfonate, an alkyl diphenyl oxide (di)sulfonate, an alcohol sulfate, an alkoxy sulfate (e.g. an alkyl alkoxy sulfate) an alkoxy sulfonate, an alcohol phosphate, an alkoxy phosphate, a sulfosuccinate ester, an alcohol ethoxylate, an alkyl phenol ethoxylate, a quaternary ammonium salt, a betaine, a sultaine and a soap (or its carboxylic acid). A person having ordinary skill in the art will immediately recognize that many surfactants are commercially available as blends of related molecules (e.g. IOS and ABS surfactants). Thus, where a co-surfactant is present within a composition provided herein, a person of ordinary skill would understand that the co-surfactant may be a blend of a plurality of related surfactant molecules (as described herein and as generally known in the art). In some embodiments, the co-surfactant is a $C_{10}$-$C_{30}$ internal olefin sulfate (IOS) or a $C_8$-$C_{30}$ alkyl benzene sulfonate (ABS). In other embodiments, the co-surfactant is a combination of a $C_{10}$-$C_{30}$ internal olefin sulfate (IOS) and a $C_8$-$C_{30}$ alkyl benzene sulfonate (ABS). In some embodiments, the $C_{10}$-$C_{30}$ of IOS is a branched unsubstituted $C_{10}$-$C_{30}$ saturated alkyl. In some embodiment, the IOS is a $C_{15}$-$C_{18}$ internal olefin sulfate. In some embodiment, the IOS is a $C_{19}$-$C_{23}$ internal olefin sulfate. In some embodiment, the IOS is a $C_{20}$-$C_{24}$ internal olefin sulfate. In some embodiment, the IOS is a $C_{15}$-$C_{18}$ internal olefin sulfate. In other embodiments, the $C_8$-$C_{30}$ of ABS is a branched unsubstituted $C_8$-$C_{30}$ saturated alkyl.

In some embodiments, the co-surfactant is an unsubstituted alkyl alkoxy sulfate having an alkyl attached to one or more alkoxylene groups (typically —$CH_2$—CH(ethyl)-O—, —$CH_2$—CH(methyl)-O—, or —$CH_2$—$CH_2$—O—) which, in turn is attached to —$SO_3^-$ or acid or salt thereof including metal cations such as sodium. In some embodiment, the alkyl alkoxy sulfate has the formula $R^A$—(BO)$_e$—(PO)$_f$-(EO)$_g$—$SO_3^-$ or acid or salt (including metal cations such as sodium) thereof, wherein BO is —$CH_2$—CH(ethyl)-O—, PO is —$CH_2$—CH(methyl)-O—, and —$CH_2$—$CH_2$—O—. The symbols e, f and g are integers from 0 to 25 wherein at least one is not zero. In some embodiment, the alkyl alkoxy sulfate is $C_{15}$-13PO-Sulfate (i.e. an unsubstituted $C_{15}$ alkyl attached to 13 —$CH_2$—CH(methyl)-O— linkers, in turn attached to —$SO_3^-$ or acid or salt thereof including metal cations such as sodium. In some embodiments, the surfactant is an unsubstituted alkyl sulfate.

Useful surfactants are disclosed, for example, in U.S. Pat. Nos. 3,811,504, 3,811,505, 3,811,507, 3,890,239, 4,463,806, 6,022,843, 6,225,267, 7,629,299; WIPO Patent Application WO/2008/079855, WO/2012/027757 and WO/2011/094442; as well as U.S. Patent Application Nos. 2005/0199395, 2006/0185845, 2006/018486, 2009/0270281, 2011/0046024, 2011/0100402, 2011/0190175, 2007/0191633, 2010/004843, 2011/0201531, 2011/0190174, 2011/0071057, 2011/0059873, 2011/0059872, 2011/0048721, 2010/0319920, and 2010/0292110. Additional useful surfactants are surfactants known to be used in enhanced oil recovery methods, including those discussed in D. B. Levitt, A. C. Jackson, L. Britton and G. A. Pope, "Identification and Evaluation of High-Performance EOR Surfactants," SPE 100089, conference contribution for the SPE Symposium on Improved Oil Recovery Annual Meeting, Tulsa, Okla., Apr. 24-26, 2006.

A person having ordinary skill in the art will immediately recognize that many surfactants are commercially available as blends of related molecules (e.g. IOS and ABS surfactants). Thus, where a surfactant is present within a composition provided herein, a person of ordinary skill would understand that the surfactant may be a blend of a plurality of related surfactant molecules (as described herein and as generally known in the art).

In some embodiment, the total surfactant concentration (i.e. the total amount of all surfactant types within the aqueous compositions and emulsion compositions provided herein) in is from about 0.05% w/w to about 10% w/w. In other embodiments, the total surfactant concentration in the aqueous composition is from about 0.25% w/w to about 10% w/w. In other embodiments, the total surfactant concentration in the aqueous composition is about 0.5% w/w. In other embodiments, the total surfactant concentration in the aqueous composition is about 1.0% w/w. In other embodiments, the total surfactant concentration in the aqueous composition is about 1.25% w/w. In other embodiments, the total surfactant concentration in the aqueous composition is about 1.5% w/w. In other embodiments, the total surfactant concentration in the aqueous composition is about 1.75% w/w. In other embodiments, the total surfactant concentration in the aqueous composition is about 2.0% w/w. In other embodiments, the total surfactant concentration in the aqueous composition is about 2.5% w/w. In other embodiments, the total surfactant concentration in the aqueous composition is about 3.0% w/w. In other embodiments, the total surfactant concentration in the aqueous composition is about 3.5% w/w. In other embodiments, the total surfactant concentration in the aqueous composition is about 4.0% w/w. In other embodiments, the total surfactant concentration in the aqueous composition is about 4.5% w/w. In other embodiments, the total surfactant concentration in the aqueous composition is about 5.0% w/w. In other embodiments, the total surfactant concentration in the aqueous composition is about 5.5% w/w. In other embodiments, the total surfactant concentration in the aqueous composition is about 6.0% w/w. In other embodiments, the total surfactant concentration in the aqueous composition is about 6.5% w/w. In other embodiments, the total surfactant concentration in the aqueous composition is about 7.0% w/w. In other embodiments, the total surfactant concentration in the aqueous composition is about 7.5% w/w. In other embodiments, the total surfactant concentration in the aqueous composition is about 8.0% w/w. In other embodiments, the total surfactant concentration in the aqueous composition is about 9.0% w/w. In other embodiments, the total surfactant concentration in the aqueous composition is about 10% w/w.

In some embodiment, the total surfactant concentration (i.e. the compound of formula (I), (II), (III), (IV), or (V) and one or more co-surfactants) in the aqueous composition is from about 0.05% w/w to about 10% w/w. In other embodiments, the total surfactant concentration in the aqueous composition is from about 0.25% to about 10%. In other embodiments, the total surfactant concentration in the aqueous composition is about 0.5%. In other embodiments, the total surfactant concentration in the aqueous composition is about 1.0%. In other embodiments, the total surfactant concentration in the aqueous composition is from about 1.25%. In other embodiments, the total surfactant concentration in the aqueous composition is from about 1.5%. In other embodiments, the total surfactant concentration in the aqueous composition is from about 1.75%. In other embodiments, the total surfactant concentration in the aqueous composition is from about 2.0%. In other embodiments, the total surfactant concentration in the aqueous composition is from about 2.5%. In other embodiments, the total surfactant concentration in the aqueous composition is from about 3.0%. In other embodiments, the total surfactant concentration in the aqueous composition is from about 3.5%. In other embodiments, the total surfactant concentration in the aqueous composition is from about 4.0%. In other embodiments, the total surfactant concentration in the aqueous composition is from about 4.5%. In other embodiments, the total surfactant concentration in the aqueous composition is from about 5.0%. In other embodiments, the total surfactant concentration in the aqueous composition is from about 5.5%. In other embodiments, the total surfactant concentration in the aqueous composition is from about 6.0%. In other embodiments, the total surfactant concentration in the aqueous composition is from about 6.5%. In other embodiments, the total surfactant concentration in the aqueous composition is from about 7.0%. In other embodiments, the total surfactant concentration in the aqueous composition is from about 7.5%. In other embodiments, the total surfactant concentration in the aqueous composition is from about 8.0%. In other embodiments, the total surfactant concentration in the aqueous composition is from about 9.0%. In other embodiments, the total surfactant concentration in the aqueous composition is from about 10%.

In some embodiments, the concentration of the compound of formula (I), (II), (III), (IV), or (V) is about 0.05% (all percentages of the compounds of formula (I), (II), (III), (IV), or (V), co-solvents and co-surfactants within the aqueous compositions and emulsion compositions herein are w/w percentages). In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.1%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.15%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.20%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (II), (IV), or (V) is about 0.25%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.30%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%.

In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.35%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.40%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.45%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.50%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.55%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.60%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.65%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.70%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.75%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.80%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.85%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.90%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 0.95%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 1.0%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 1.25%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 1.50%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%.

In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 1.75%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 2%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 3%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 4%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of formula (I), (II), (III), (IV), or (V) is about 5%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the aqueous composition further includes an alkali agent. An alkali agent as provided herein is a basic, ionic salt of an alkali metal (e.g. lithium, sodium, potassium) or alkaline earth metal element (e.g. magnesium, calcium, barium, radium). In some embodiments, the alkali agent is NaOH, KOH, LiOH, $Na_2CO_3$, $NaHCO_3$, Na-metaborate, Na silicate, Na orthosilicate, or $NH_4OH$. The aqueous composition may include seawater, or fresh water from an aquifer, river or lake. In some embodiments, the aqueous composition includes hard brine water or soft brine water. In some further embodiments, the water is soft brine water. In some further embodiments, the water is hard brine water. Where the aqueous composition includes soft brine water, the aqueous composition may include an alkaline agent. In soft brine water the alkaline agent provides for enhanced soap generation from the active oils, lower surfactant adsorption to the solid material (e.g. rock) in the reservoir and increased solubility of viscosity enhancing water soluble polymers. The alkali agent is present in the aqueous composition at a concentration from about 0.1% w/w to about 10% w/w. The combined amount of alkali agent and compound provided herein (e.g. compound of formula (I), (II), (III), (IV), or (V)) present in the aqueous composition provided herein is approximately equal to or less than about 10% w/w. In some embodiments, the total concentration of alkali agent (i.e. the total amount of alkali agent within the aqueous compositions and emulsion compositions provided herein) in is from about 0.05% w/w to about 5% w/w. In other embodiments, the total alkali agent concentration in the aqueous composition is from about 0.25% w/w to about 5% w/w. In other embodiments, the total alkali agent concentration in the aqueous composition is about 0.5% w/w. In other embodiments, the total alkali agent concentration in the aqueous composition is about 0.75% w/w. In other embodiments, the total alkali agent concentration in the aqueous composition is about 1% w/w. In other embodiments, the total alkali agent concentration in the aqueous composition is about 1.25% w/w. In other embodiments, the total alkali agent concentration in the aqueous composition is about 1.50% w/w. In other embodiments, the total alkali agent concentration in the aqueous composition is about 1.75% w/w. In other embodiments, the total alkali agent concentration in the aqueous composition is about 2% w/w. In other embodiments, the total alkali agent concentration in the aqueous composition is about 2.25% w/w. In other embodiments, the total alkali agent concentration in the aqueous composition is about 2.5% w/w. In other embodiments, the total alkali agent concentration in the aqueous composition is about 2.75% w/w. In other embodiments, the total alkali agent concentration in the aqueous composition is about 3% w/w. In other embodiments, the total alkali agent concentration in the aqueous composition is about 3.25% w/w. In other embodiments, the total alkali agent concentration in the aqueous composition is about 3.5% w/w. In other embodiments, the total alkali agent concentration in the aqueous composition is about 3.75% w/w. In other embodiments, the total alkali agent concentration in the aqueous composition is about 4% w/w. In other embodiments, the total alkali agent concentration in the aqueous composition is about 4.25% w/w. In other embodiments, the total alkali agent concentration in the aqueous composition is about 4.5% w/w. In other embodiments, the total alkali agent concentration in the aqueous composition is about 4.75% w/w. In other embodiments, the total alkali agent concentration in the aqueous composition is about 5.0% w/w.

As described above the aqueous composition may include the compound of formula (II). In some embodiments, the compound is C16/C16 Epoxide-15PO-10EO-sulfate (i.e. a compound as described herein for example in formula (II)), wherein $R^1$ is linear unsubstituted $C_{14}$ alkyl, $R^2$ is linear unsubstituted $C_{16}$ alkyl, w is 15, y is 10, X is —$SO_3^-Na^+$ and the co-surfactant is $C_{11}$ ABS. In some further embodiments, the alkali agent is $Na_2CO_3$. In some embodiments, the C16/C16 Epoxide-15PO-10EO-sulfate is present from about 0.01% to about 5% w/w. In some further embodiments, the C16/C16 Epoxide-15PO-10EO-sulfate is present at about 0.5% w/w. In other further embodiments, the C16/C16 Epoxide-15PO-10EO-sulfate is present at 0.25% w/w.

In some embodiments, the compound is isofol C32/C18 epoxide-15PO-10EO-sulfate (i.e. a compound as described herein for example in formula (II)), wherein $R^1$ is linear unsubstituted $C_{16}$ alkyl, $R^2$ is branched unsubstituted $C_{32}$ alkyl formed by a Guerbet reaction, w is 15, y is 10, X is —$SO_3^-Na^+$ and the co-surfactant is $C_{11}$ ABS. In some further embodiments, the alkali agent is $Na_2CO_3$. In some embodiments, isofol C32/C18 epoxide-15PO-10EO-sulfate is present from about 0.01% to about 5% w/w. In some further embodiments, the isofol C32/C18 epoxide-15PO-10EO-sulfate is present at about 0.5% w/w. In other further embodiments, the isofol C32/C18 epoxide-15PO-10EO-sulfate is present at 0.25% w/w.

In some embodiments, the compound is TSP-C18 Epoxide-15PO-20EO-sulfate (i.e. a compound as described herein for example in formula (II)), wherein $R^1$ is linear unsubstituted $C_{16}$ alkyl, $R^2$ is TSP (i.e. styrylphenol), w is 15, y is 20, X is —$SO_3^-Na^+$ and the co-surfactant is $C_{11}$ ABS. In some further embodiments, the alkali agent is $Na_2CO_3$. In some embodiments, the TSP-C18 Epoxide-15PO-20EO-sulfate is present from about 0.01% to about 5% w/w. In some further embodiments, the TSP-C18 Epoxide-15PO-20EO-sulfate is present at about 0.5% w/w. In other further embodiments, the TSP-C18 Epoxide-15PO-20EO-sulfate is present at 0.25% w/w.

In some embodiments, the compound is C16/C16 epoxide-15PO-20EO glyceryl sulfonate (i.e. a compound as described herein for example in formula (II)), wherein $R^1$ is linear unsubstituted $C_{16}$ alkyl, $R^2$ is linear unsubstituted $C_{16}$ alkyl, w is 15, y is 20, X is

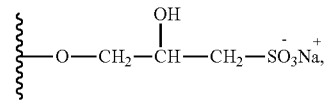

and the co-surfactant is $C_{11}$ ABS. In some further embodiments, the alkali agent is $Na_2CO_3$. In some embodiments, the C16/C16 epoxide-15PO-10EO-carboxylate is present from about 0.01% to about 5% w/w. In some further embodiments, the C16/C16 epoxide-15PO-20EO glyceryl sulfonate is present at about 0.5% w/w. In other further embodiments, the C16/C16 epoxide-15PO-20EO glyceryl sulfonate is present at 0.25% w/w.

In some embodiments, the compound is C16/C16 epoxide-15PO-10EO-carboxylate (i.e. a compound as described herein for example in formula (II)), wherein $R^1$ is linear unsubstituted $C_{16}$ alkyl, $R^2$ is linear unsubstituted $C_{16}$ alkyl, w is 15, y is 10, X is —O—C(O)O$^-$Na$^+$ and the co-surfactant is $C_{20}$-$C_{24}$ IOS. In some further embodiments, the alkali agent is $Na_2CO_3$. A person of skill in the art would immediately recognize that the $C_{20}$-$C_{24}$ IOS encompasses a blend of IOS surfactants as described herein. Therefore, $C_{20}$-$C_{24}$ IOS and similar IOS blends described herein may be alternatively referred to as a plurality of co-surfactants. In some embodiments, the C16/C16 epoxide-15PO-10EO-carboxylate is present from about 0.01% to about 5% w/w. In some further embodiments, the C16/C16 epoxide-15PO-10EO-carboxylate is present at about 0.5% w/w. In other further embodiments, the C16/C16 epoxide-15PO-10EO-carboxylate is present at 0.25% w/w.

In some embodiments, the aqueous composition may include the compound of formula (V). In some embodiments, the compound is C16-7PO-C16 Epoxide-8PO-10EO-sulfate (i.e. a compound as described herein for example in formula (V)), wherein $R^1$ is linear unsubstituted $C_{14}$ alkyl, $R^{2'}$ is linear unsubstituted $C_{16}$ alkyl, $R^3$ is methyl, n is 7, t is 8, u is 10, X is —$SO_3^-Na^+$ and the co-surfactant is $C_{11}$ ABS. In some further embodiments, the alkali agent is $Na_2CO_3$). In some embodiments, the compound is C16-15PO-C16 Epoxide-10EO-sulfate (i.e. a compound as described herein for example in formula (V)), wherein $R^1$ is linear unsubstituted $C_{14}$ alkyl, $R^{2'}$ is linear unsubstituted $C_{16}$ alkyl, $R^3$ is methyl, n is 15, t is 0, u is 10, X is —$SO_3^-Na^+$ and the co-surfactant is $C_{11}$ ABS. In some further embodiments, the alkali agent is $Na_2CO_3$.

In some embodiments, the aqueous composition may include the compound of formula (III). In some embodiments, the compound is C16/C16 Epoxide-15BO-15PO-10EO-sulfate (i.e. a compound as described herein for example in formula (III)), wherein $R^1$ is linear unsubstituted $C_{14}$ alkyl, $R^{2'}$ is linear unsubstituted $C_{16}$ alkyl, $R^3$ is ethyl, v is 15, w is 15, y is 10, X is —$SO_3^-Na^+$ and the co-surfactant is $C_{11}$ ABS. In some further embodiments, the alkali agent is $Na_2CO_3$.

In some embodiments, the aqueous composition includes a viscosity enhancing water-soluble polymer. In some embodiments, the water-soluble polymer may be a biopolymer such as xanthan gum or scleroglucan, a synthetic polymer such as polyacryamide, hydrolyzed polyarcrylamide or co-polymers of acrylamide and acrylic acid, 2-acrylamido 2-methyl propane sulfonate or N-vinyl pyrrolidone, a synthetic polymer such as polyethylene oxide, or any other high molecular weight polymer soluble in water or brine. In some embodiments, the polymer is polyacrylamide (PAM), partially hydrolyzed polyacrylamides (HPAM), and copolymers of 2-acrylamido-2-methylpropane sulfonic acid or sodium salt or mixtures thereof, and polyacrylamide (PAM) commonly referred to as AMPS copolymer and mixtures of the copolymers thereof. Molecular weights of the polymers may range from about 10,000 daltons to about 20,000,000 daltons. In some embodiments, the viscosity enhancing water-soluble polymer is used in the range of about 500 to about 5000 ppm concentration, such as from about 1000 to 2000 ppm (e.g. in order to match or exceed the reservoir oil viscosity under the reservoir conditions of temperature and pressure).

In other embodiments, the aqueous composition includes a co-solvent. In some embodiments, the co-solvent is an alcohol, alcohol ethoxylate, glycol ether, glycols, or glycerol.

In some embodiments, the aqueous composition includes a gas. For instance, the gas may be combined with the aqueous composition to reduce its mobility by decreasing the liquid flow in the pores of the solid material (e.g. rock). In some embodiments, the gas may be supercritical carbon dioxide, nitrogen, natural gas or mixtures of these and other gases.

In some embodiments, the aqueous composition has a pH of less than about 13.0. In other embodiments, the aqueous composition has a pH of less than about 12. In other embodiments, the aqueous composition has a pH of less than about 11. In other embodiments, the aqueous composition has a pH of less than about 10. In other embodiments, the aqueous composition has a pH of less than about 9.0. In other embodiments, the aqueous composition has a pH of less than about 8.0. In other embodiments, the aqueous composition has a pH of less than about 7.0.

In some embodiments, the aqueous composition has a salinity of at least 10,000 ppm. In other embodiments, the aqueous composition has a salinity of at least 50,000 ppm. In other embodiments, the aqueous composition has a salinity of at least 100,000 ppm. The total range of salinity (total dissolved solids in the brine) is 100 ppm to saturated brine (about 260,000 ppm). The aqueous composition may include seawater, brine or fresh water from an aquifer, river or lake. The aqueous combination may further include salt to increase the salinity. In some embodiments, the salt is NaCl, KCl, $CaCl_2$, $MgCl_2$, $CaSO_4$ or $Na_2CO_3$.

In some embodiments, the temperature of the aqueous composition is at least 40° C. In other embodiments, the temperature of the aqueous composition is at least 100° C. In some embodiments, the aqueous composition has a viscosity of between 20 mPa·s and 100 mPa·s. The viscosity of the aqueous solution may be increased from 0.3 mPa·s to 1, 2, 10, 20, 100 or even 1000 mPa·s by including a water-soluble polymer. As mentioned above, the apparent viscosity of the aqueous composition may be increased with a gas (e.g. a foam forming gas) as an alternative to the water-soluble polymer.

In another aspect, an emulsion composition is provided including an unrefined petroleum phase and an aqueous. The aqueous phase includes the compound described herein (e.g. a compound of formula (I), (II), (III), (IV), or (V)). In some embodiments, the aqueous phase includes the components set forth in the aqueous composition provided above. For example, in some embodiments, the aqueous phase further includes a co-surfactant (e.g. wherein the compound and the co-surfactant are present in synergistic surface active amount, a surfactant stabilizing amount, and/or a synergistic solubilizing amount). In some embodiments, the aqueous phase includes a co-surfactant and a co-solvent. The aqueous phase may include a combination of one or more co-surfactants and one or more co-solvents. In other embodiments, the aqueous phase includes a co-surfactant and an alkali agent.

In some embodiments, the emulsion composition is a microemulsion. A "microemulsion" as referred to herein is a thermodynamically stable mixture of oil, water and surfactants that may also include additional components such as co-solvents, electrolytes, alkali and polymers. In contrast, a "macroemulsion" as referred to herein is a thermodynamically unstable mixture of oil and water that may also include additional components.

In other embodiments, the oil and water solubilization ratios are insensitive to the combined concentration of divalent metal cations (e.g. $Ca^{+2}$ and $Mg^{+2}$) within the aqueous phase. In other embodiments, the oil and water solubilization ratios are insensitive to the salinity of the water or to all of the specific electrolytes contained in the water. The term "insensitive" used in the context of this paragraph means that the solubilization ratio tends not to change (e.g. tends to remain constant) as the concentration of divalent metal cations and/or salinity of water changes. In some embodiments, the change in the solubilization ratios are less than 5%, 10%, 20%, 30%, 40%, or 50% over a divalent metal cation concentration range of 10 ppm, 100 ppm, 1000 ppm or 10,000 ppm. In another embodiment, the change in the solubilization ratios are less than 5%, 10%, 20%, 30%, 40%, or 50% over a salinity concentration range of 10 ppm, 100 ppm, 1000 ppm or 10,000 ppm.

In another aspect, a method of displacing a hydrocarbon material in contact with a solid material is provided. The method includes contacting a hydrocarbon material with the compound described herein (e.g. a compound of formula (I), (II), (III), (IV), or (V)), wherein the hydrocarbon material is in contact with a solid material. The hydrocarbon material is allowed to separate from the solid material thereby displacing the hydrocarbon material in contact with the solid material. In some embodiments, the solid material is contacted with the compound. A "hydrocarbon material," as provided herein, is a hydrophobic material containing alkyl chains. The compound may be present in an aqueous composition or an emulsion composition as described above.

In other embodiments, the hydrocarbon material is unrefined petroleum (e.g. in a petroleum reservoir). The solid material may be a natural solid material (i.e. a solid found in nature such as rock). The natural solid material may be found in a petroleum reservoir. In some embodiments, the method is an enhanced oil recovery method. Enhanced oil recovery methods are well known in the art. A general treatise on enhanced oil recovery methods is *Basic Concepts in Enhanced Oil Recovery Processes* edited by M. Baviere (published for SCI by Elsevier Applied Science, London and New York, 1991). For example, in an enhanced oil recovery method, the displacing of the unrefined petroleum in contact with the solid material is accomplished by contacting the unrefined with a compound provided herein (e.g. a compound of formula (I), (II), (III), (IV), or (V)), wherein the unrefined petroleum is in contact with the solid material. The unrefined petroleum may be in an oil reservoir. The compound provided herein (e.g. a compound of formula (I), (II), (III), (IV), or (V)) is pumped into the reservoir in accordance with known enhanced oil recovery parameters. The compound may be pumped into the reservoir as part of the aqueous compositions provided herein and, upon contacting the unrefined petroleum, form an emulsion composition provided herein.

In some embodiments, the natural solid material is rock or regolith. The natural solid material may be a geological formation such as clastics or carbonates. The natural solid material may be either consolidated or unconsolidated material or mixtures thereof. The hydrocarbon material may be trapped or confined by "bedrock" above or below the natural solid material. The hydrocarbon material may be found in fractured bedrock or porous natural solid material. In other embodiments, the regolith is soil. In some embodiments, the compound forms part of an aqueous composition comprising a co-surfactant and the hydrocarbon material is an unrefined petroleum material. In some embodiments, the co-surfactant is an internal olefin sulfonate (IOS), an alfa olefin sulfonate (AOS), an alkyl aryl sulfonate (ARS), an alkane sulfonate, a petroleum sulfonate, an alkyl diphenyl ether (di)sulfonate, an alcohol sulfate, an alkoxy sulfate, an alcohol phosphate, an alkoxy phosphate, a sulfosuccinate ester, an alcohol ethoxylate, an alkyl phenol ethoxylate or a quaternary ammonium salt. In other embodiments, the co-surfactant is a $C_{10}$-$C_{30}$ internal olefin sulfate or a $C_8$-$C_{30}$ alkyl benzene sulfonate. In some embodiments, the aqueous composition further includes a viscosity enhancing polymer.

In some embodiments, an emulsion forms after the contacting. The emulsion thus formed may be the emulsion composition as described above. In some embodiments, the method includes allowing an unrefined petroleum acid within the unrefined petroleum material to enter into the emulsion (e.g. emulsion composition), thereby converting the unrefined petroleum acid into a surfactant. In other words, where the unrefined petroleum acid converts into a surfactant it is mobilized and therefore separates from the solid material.

In another aspect, a method of converting (e.g. mobilizing) an unrefined petroleum acid into a surfactant is provided. The method includes contacting a petroleum material with an aqueous composition thereby forming an emulsion in contact with the petroleum material, wherein the aqueous composition includes the compound described herein (e.g. a compound of formula (I), (II), (III), (IV), or (V)) and a co-surfactant. Thus, in some embodiments, the aqueous composition is the aqueous composition described above. And in some embodiments, the emulsion is the emulsion composition described above. An unrefined petroleum acid within said unrefined petroleum material is allowed to enter into the emulsion, thereby converting (e.g. mobilizing) the unrefined petroleum acid into a surfactant. In some embodiments, the reactive petroleum material is in a petroleum reservoir. In some embodiments, as described above and as is generally known in the art, the unrefined petroleum acid is a naphthenic acid. In some embodiments, as described above and as is generally known in the art, the unrefined petroleum acid is a mixture of naphthenic acid.

In another aspect, a method of making a compound described herein (e.g. a compound of formula (I), (II), (III), (IV), or (V)) is provided. The method includes contacting an epoxide compound with an alcohol thereby forming an epoxide-alcohol mixture. The temperature of the epoxide-alcohol mixture is increased thereby forming an epoxide-alcohol adduct. The epoxide-alcohol adduct is contacted with a $C_1$-$C_4$ alkoxide thereby forming an alkoxylated hydrophobe and the alkoxylated hydrophobe is contacted with one or more anionic functional groups thereby forming the compound. In the method provided herein the epoxide compound has the formula

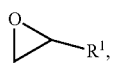  (VIIa)

wherein $R^1$ is linear unsubstituted $C_{12}$-$C_{20}$ alkyl. The alcohol has the formula $R^2$—OH (VIIb), wherein $R^2$ is as described herein (e.g. linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl). The epoxide-alcohol adduct is a compound having the formula

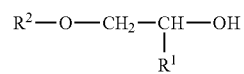  (VIIc)

wherein $R^1$ and $R^2$ are as described above (e.g. $R^1$ is linear unsubstituted $C_{12}$-$C_{20}$ alkyl; $R^2$ is linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl). The $C_1$-$C_4$ alkoxide has the formula

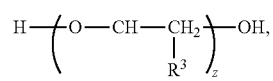  (VIId)

wherein $R^3$ and z are as described above. For example, $R^3$ is unsubstituted $C_1$-$C_4$ alkyl and z is an integer from 1 to 100. The alkoxylated hydrophobe provided herein has the formula

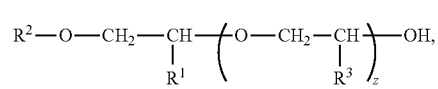  (VIIIe)

wherein $R^1$, $R^2$, $R^3$ and z are as described above (e.g. $R^1$ is linear unsubstituted $C_{12}$-$C_{20}$ alkyl; $R^2$ is linear unsubstituted $C_{12}$-$C_{25}$ alkyl, branched unsubstituted $C_{30}$-$C_{50}$ alkyl, $R^{4a}$-substituted $C_{20}$-$C_{100}$ heteroalkyl or $R^{4a}$-substituted phenyl; $R^3$ is unsubstituted $C_1$-$C_4$ alkyl).

In some embodiments, a method of making a compound of formula (II) (e.g. compound of Example 2, 6, 7, or 9) is provided. The method includes contacting an epoxide compound of formula (VIIa), wherein $R^1$ is unsubstituted $C_{14}$ alkyl, with an alcohol of formula (VIIb), wherein $R^2$ is unsubstituted $C_{16}$ alkyl, branched unsubstituted $C_{30}$-$C_{50}$ alkyl formed by a Guerbet reaction (compound of Example 6), or R4a-substituted phenyl (e.g TSP of Example 7), thereby forming an epoxide-alcohol adduct. The epoxide-alcohol adduct is contacted with a $C_1$-$C_4$ alkoxide of formula (VIId), wherein $R^3$ is independently methyl or hydrogen and z is an integer from 10 to 25, thereby forming an alkoxylated hydrophobe, wherein $R^1$, $R^2$, $R^3$ and z are as described above. The alkoxylated hydrophobe is reacted with an anionic functional group, wherein X is —O—$SO_3Na^+$ (e.g. for compound of Example 2, 6, or 7) or —O—$CH_2$—C(O)$O^-Na^+$ (e.g. for compound of Example 9), thereby forming said compound of formula (II).

In some embodiments, a method of making a compound of formula (V) (e.g. compound of Example 3 and 4) is provided. The method includes contacting an alcohol of formula $R^{2'}$—OH, wherein $R^{2'}$ is described herein (e.g. unsubstituted $C_{16}$ alkyl), with a $C_1$-$C_4$ alkoxide of formula (VIId), wherein $R^3$ is methyl and z is 7, thereby forming an alkyl alkoxylate having the formula

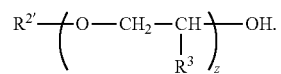  (VIIf)

The alkyl alkoxylate is contacted with an epoxide compound of formula (VIIa), wherein $R^1$ is unsubstituted $C_{14}$ alkyl, thereby forming the epoxide-alcohol adduct. The epoxide-alcohol adduct is contacted with a $C_1$-$C_4$ alkoxide of formula (VIId), wherein $R^3$ is independently hydrogen or methyl and z is an integer from 5 to 30, thereby forming the alkoxylated hydrophobe of formula (VIIe), wherein $R^1$, $R^{2'}$, $R^3$ and z are as described above. The alkoxylated hydrophobe is reacted with an anionic functional group where X is —O—$SO_3^-$ $Na^+$, thereby forming said compound of formula (V).

In some embodiments, a method of making a compound of formula (III) (e.g. compound of Example 5) is provided. The method includes contacting an epoxide compound of formula (VIIa), wherein $R^1$ is unsubstituted $C_{14}$ alkyl, with an alcohol of formula (VIIb), wherein $R^2$ is unsubstituted $C_{16}$ alkyl, thereby forming an epoxide-alcohol adduct of formula (VIIc). The epoxide-alcohol adduct is contacted with a $C_1$-$C_4$ alkoxide of formula (VIId), wherein $R^3$ is independently methyl or hydrogen and z is an integer from 10 to 60, thereby forming an alkoxylated hydrophobe of formula (VIIf), wherein $R^1$, $R^2$, $R^3$ and z are as described above. The alkoxylated hydrophobe is reacted with an anionic functional group, wherein X is —O—$SO_3^-Na^+$, thereby forming said compound of formula (III).

In some embodiments, a method of making a compound of formula (II) (e.g. compound of Example 8) is provided. The method includes contacting an epoxide compound, wherein $R^1$ is unsubstituted $C_{14}$ alkyl, with an alcohol of formula (VIIb), wherein $R^2$ is unsubstituted $C_{16}$ alkyl, thereby forming an epoxide-alcohol adduct of formula (VIIc). The epoxide-alcohol adduct is contacted with a $C_1$-$C_4$ alkoxide of formula (VIId), wherein $R^3$ is independently methyl or hydrogen and z is an integer from 10 to 40, thereby forming an alkoxylated hydrophobe is contacted with an epoxide compound of formula

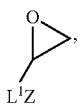
(VIIg)

wherein $L^1$ is substituted or unsubstituted alkylene (e.g. unsubstituted methylene) and Z is halogen (e.g. Cl), thereby forming an alkoxylated hydrophobe of formula (VIIe), wherein $R^1$, $R^2$, $R^3$ and z are as described above. The alkoxylated hydrophobe is reacted with an anionic functional group, wherein X is

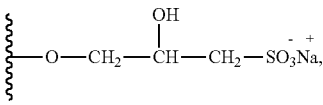

thereby forming said compound of formula (II).

IV. Examples

Example 1

Synthesis of Isofol (Guerbet) C32-15PO-10-EO-Sulfate for Comparative Purposes

A linear alcohol (1) reacts in the presence of a catalyst and heat (a) to form a Guerbet alcohol (2). In the presence of a base, 15 polypropylene oxide, 10 ethylene oxide and heat (b) a near mid-point branched large hydrophobe is formed. (c) Reaction of the large hydrophobe with sulfamic acid in the presence of heat and neutralization forms the corresponding large hydrophobe sulfate (4).

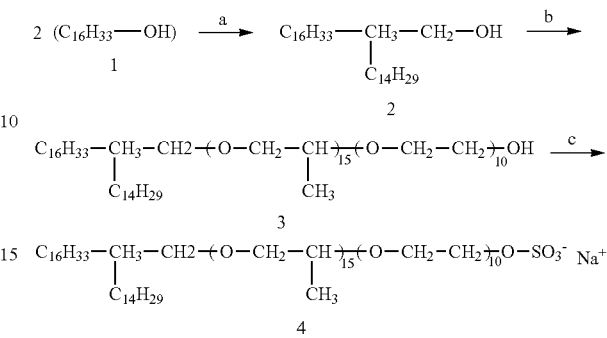

Example 2

Synthesis of C16/C16 Epoxide-15PO-10EO-Sulfate

Compound (1), wherein $R^2$ is unsubstituted $C_{16}$ alkyl, is contacted with an epoxide compound, wherein $R^1$ is unsubstituted $C_{14}$ alkyl, a base and heat (a) to form compound (2). 15 propylene oxide and 10 ethylene oxide are reacted with compound (2) in the presence of heat (b) to form compound (3). (c) Reaction of compound (3) with sulfamic acid in the presence of heat and neutralization results in the synthesis of compound (4) (i.e. C16/C16 Epoxide-15PO-10EO-Sulfate).

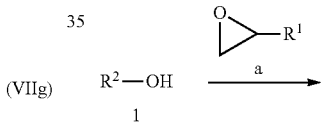

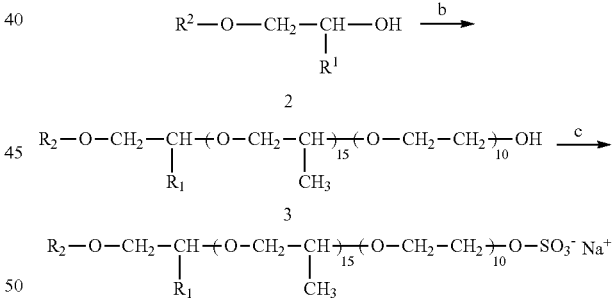

Example 3

Synthesis of C16-7PO-C16 Epoxide-8PO-10EO-Sulfate

Compound (1), wherein $R^2$ is unsubstituted $C_{16}$ alkyl, is contacted with a base, heat, and 7 propylene oxide (a) to form compound (2). Compound (2) is reacted with (b) an epoxide compound, where $R^1$ is unsubstituted $C_{14}$ alkyl, and heat to form compound (3). 8 propylene oxide and 10 ethylene oxide are reacted with compound (3) in the presence of heat (c) to form compound (4). (d) Reaction of compound (4) with sulfamic acid in the presence of heat and neutralization results in the synthesis of compound (5) (i.e. C16-7PO-C16 Epoxide-8PO-10EO-Sulfate).

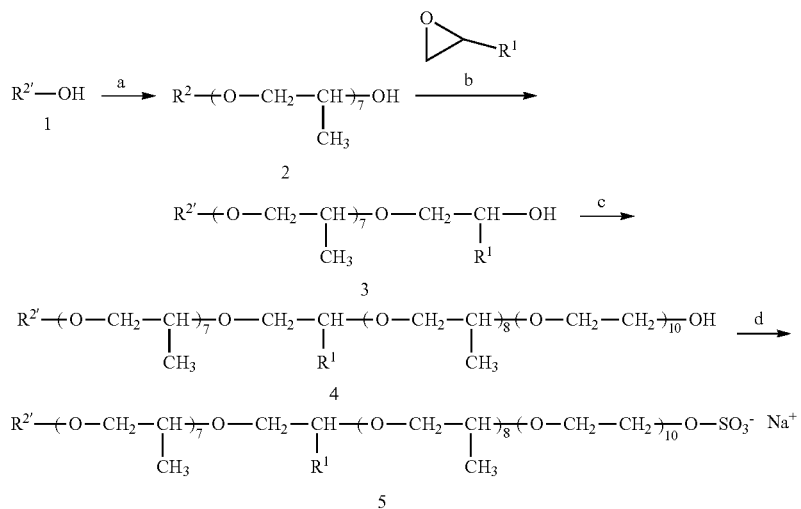

Example 4

Synthesis of C16-15PO-C16 Epoxide-10EO-Sulfate

Compound (1), wherein $R^{2'}$ is unsubstituted $C_{16}$ alkyl, is contacted with a base, heat, and 15 propylene oxide (a) to form compound (2). Compound (2) is contacted with (b) an epoxide compound, wherein $R^1$ is unsubstituted $C_{14}$ alkyl, and heat to form compound (3). 10 ethylene oxide is contacted with compound (3) in the presence of heat (c) to form compound (4). (d) Reaction of compound (4) with sulfamic acid in the presence of heat and neutralization results in the synthesis of compound (5) (i.e. C16-15PO-C16 Epoxide-10EO-Sulfate).

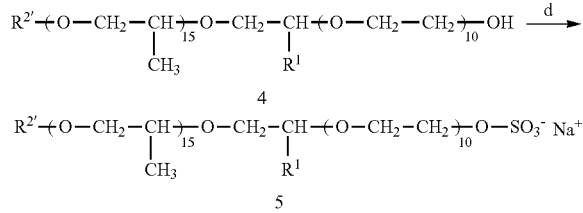

Example 5

Synthesis of C16/C16 Epoxide-15BO-15PO-10EO-Sulfate

Compound (1), wherein $R^2$ is unsubstituted $C_{16}$ alkyl, is contacted with a base, heat, and an epoxide compound, wherein $R^1$ is $C_{14}$ alkyl, (a) to form compound (2). 15 butylene oxide, 15 propylene oxide and 10 ethylene oxide are contacted with compound (2) in the presence of heat (b) to form compound (3). Reaction of compound (3) with (c) sulfamic acid in the presence of heat and neutralization results in the synthesis of compound (4) (i.e. C16/C16 Epoxide-15BO-15PO-10EO-Sulfate).

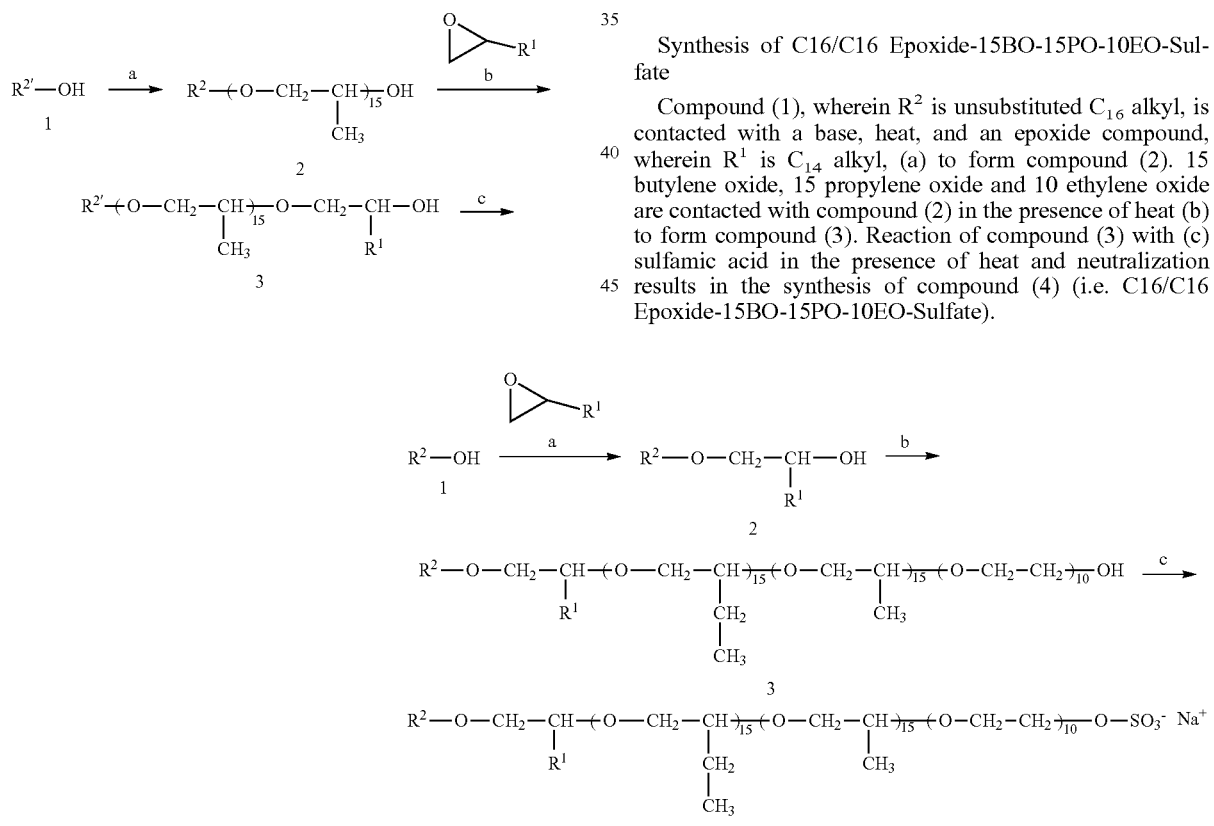

Example 6

Synthesis of Isofol C32-C18 Epoxide-15PO-10EO-Sulfate

Compound (1), wherein $R^2$ is branched unsubstituted $C_{32}$ alkyl (e.g. as formed by a Guerbet reaction), is contacted (a) with a base, heat, and an epoxide compound, wherein $R^1$ is $C_{16}$ alkyl, to form compound (2). 15 propylene oxide and 10 ethylene oxide are contacted with compound (2) in the presence of heat (b) to form compound (3). Reaction of compound (3) with (c) sulfamic acid, in the presence of heat and neutralization results in the synthesis of compound (4) (i.e. Isofol C32-C18 Epoxide-15PO-10EO-Sulfate).

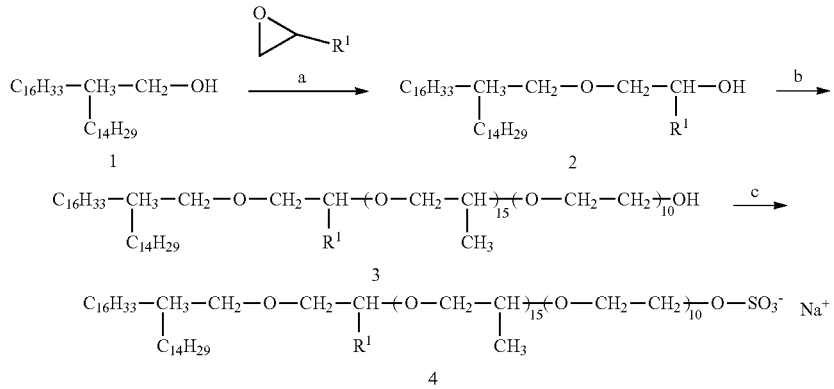

Example 7

Synthesis of TSP-C18 Epoxide-15PO-20EO-Sulfate

One molecule phenol (1) and three molecules of styrene (2) are combined under conditions (a) allowing for the formation tristyrylphenol (TSP) (3). TSP (i.e. compound (3)) is reacted with (b) a base, heat, and an epoxide compound, wherein $R^1$ is $C_{16}$ alkyl, to form compound (4). 15 propylene oxide and 20 ethylene oxide are contacted with compound (4) in the presence of heat (c) to form compound (5). Reaction of compound (5) with (d) sulfamic acid, in the presence of heat and neutralization results in the synthesis of compound (6) (4) (i.e. TSP-C18 Epoxide-15PO-20EO-Sulfate).

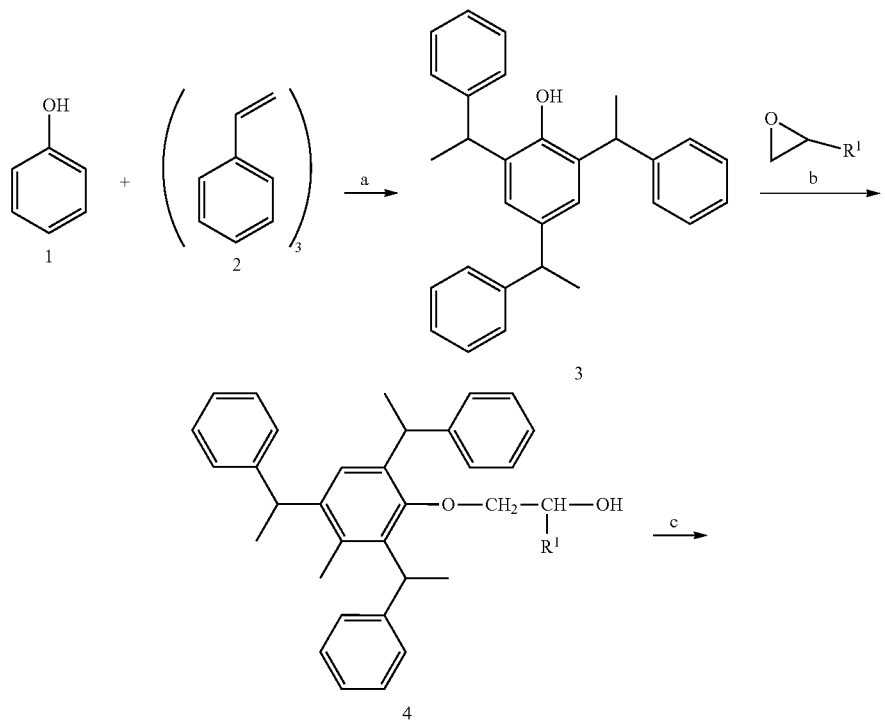

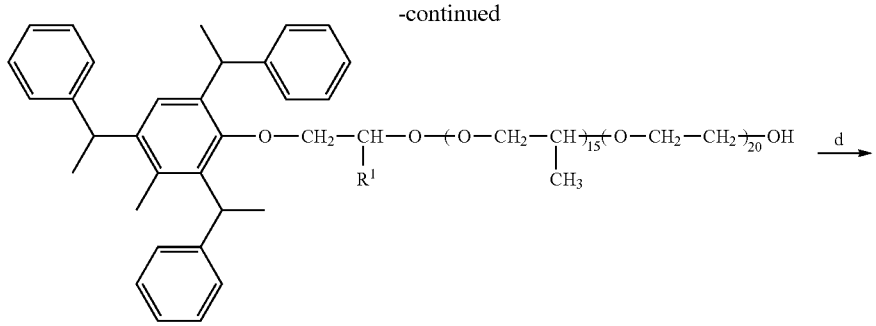

5

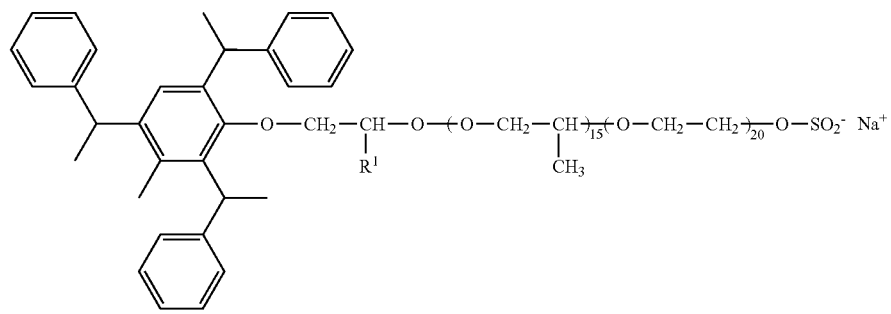

6

Example 8

Synthesis of C16/C16 Epoxide -15PO-20EO Glyceryl Sulfonate

Compound (1), wherein $R^2$ is unsubstituted $C_{16}$ alkyl is contacted with an epoxide compound, wherein $R^1$ is unsubstituted $C_{14}$ alkyl, a base and heat (a) to form compound (2). 15 propylene oxide and 20 ethylene oxide are contacted with compound (2) in the presence of heat (b) to form compound (3). Compound 3 is contacted with 2-(chloromethyl)oxirane and $BF_3$ (c) forming compound (4). (d) Reaction of compound (4) with sulfamic acid in the presence of heat and neutralization results in the synthesis of compound (5) (i.e. C16/C16 Epoxide -15PO-20EO Glyceryl Sulfonate).

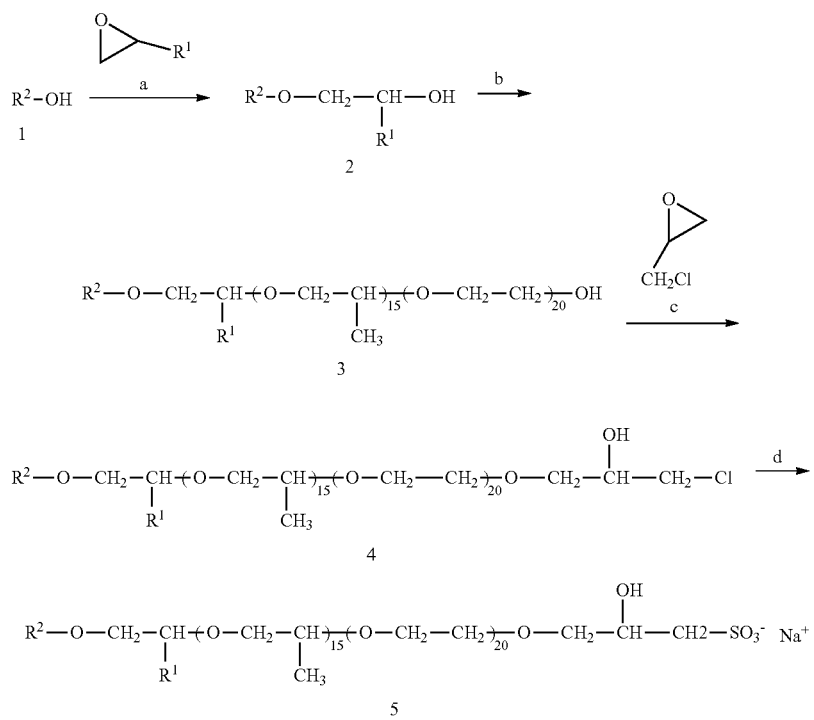

Example 9

Synthesis of C16/C16 Epoxide-15PO-10EO-Carboxylate

Compound (1), wherein $R^2$ is unsubstituted $C_{16}$ alkyl, is contacted with an epoxide compound, wherein $R^1$ is unsubstituted $C_{14}$ alkyl, a base and heat (a) to form compound (2). 15 propylene oxide and 10 ethylene oxide are contacted with compound (2) in the presence of heat (b) to form compound (3). (c) Reaction of compound (3) with sulfamic acid in the presence of heat and neutralization results in the synthesis of compound (4) (i.e. C16/C16 epoxide-15PO-10EO-carboxylate).

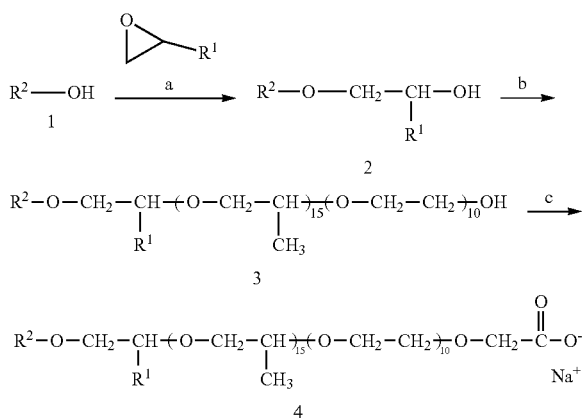

Phase Behavior Procedures

Phase Behavior Screening: Phase behavior studies have been used to characterize chemicals for EOR. There are many benefits in using phase behavior as a screening method. Phase Behavior studies are used to determine, measure or observe characteristics related to chemical performance such as the following examples but are not limited to these examples: (1) the effect of electrolytes; (2) oil solubilization and IFT reduction, (3) microemulsion densities; (4) microemulsion viscosities; (5) coalescence times; (6) optimal surfactant-co-solvent formulations; and/or (7) optimal properties for recovering oil from cores and reservoirs.

Thermodynamically stable phases can form with oil, water and surfactant mixtures. Surfactants form micellar structures at concentrations at or above the critical micelle concentration (CMC). The emulsion coalesces into a separate phase at the oil-water interface and is referred to as a microemulsion. A microemulsion is a surfactant-rich distinct phase consisting of surfactant, oil and water and possibly co-solvents and other components. This phase is thermodynamically stable in the sense that it will return to the same phase volume at a given temperature. Some workers in the past have added additional requirements, but for the purposes of this engineering study, the only requirement will be that the microemulsion is a thermodynamically stable phase.

The phase transition is examined by keeping all variables fixed except for the scanning variable. The scan variable is changed over a series of pipettes and may include, but is not limited to, salinity, temperature, chemical (surfactant, alcohol, electrolyte), oil, which is sometimes characterized by its equivalent alkane carbon number (EACN), and surfactant structure, which is sometimes characterized by its hydrophilic-lipophilic balance (HLB). The phase transition was first characterized by Winsor (1954) into three regions: Type I—excess oleic phase, Type III—aqueous, microemulsion and oleic phases, and the Type II—excess aqueous phase. The phase transition boundaries and some common terminology are described as follows: Type I to III—lower critical salinity, Type III to II—upper critical salinity, oil solubilization ratio (Vo/Vs), water solubilization ratio (Vw/Vs), the solubilization value where the oil and water solubilization ratios are equal is called the Optimum Solubilization Ratio (a*), and the electrolyte concentration where the optimum solubilization ratio occurs is referred to as the Optimal Salinity (S*).

Determining Interfacial Tension

Efficient use of time and lab resources can lead to valuable results when conducting phase behavior scans. A correlation between oil and water solubilization ratios and interfacial tension was suggested by Healy and Reed (1976) and a theoretical relationship was later derived by Chun Huh (1979). Lowest oil-water IFT occurs at optimum solubilization as shown by the Chun Huh theory. This is equated to an interfacial tension through the Chun Huh equation, where IFT varies with the inverse square of the solubilization ratio:

$$\gamma = \frac{C}{\sigma^2}. \qquad (1)$$

For most crude oils and microemulsions, C=0.3 is a good approximation. Therefore, a quick and convenient way to estimate IFT is to measure phase behavior and use the Chun-Huh equation to calculate IFT. The IFT between microemulsions and water and/or oil can be very difficult and time consuming to measure and is subject to larger errors, so using the phase behavior approach to screen hundreds of combinations of surfactants, co-surfactants, co-solvents, electrolytes, oil, and so forth is not only simpler and faster, but avoids the measurement problems and errors associated with measuring IFT especially of combinations that show complex behavior (gels and so forth) and will be screened out anyway. Once a good formulation has been identified, then it is still a good idea to measure IFT.

Equipment

Phase behavior experiments are created with the following materials and equipment.

Mass Balance: Mass balances are used to measure chemicals for mixtures and determine initial saturation values of cores.

Water Deionizer: Deionized (DI) water is prepared for use with all the experimental solutions using a Nanopure™ filter system. This filter uses a recirculation pump and monitors the water resistivity to indicate when the ions have been removed. Water is passed through a 0.45 micron filter to eliminate undesired particles and microorganisms prior to use.

Borosilicate Pipettes: Standard 5 mL borosilicate pipettes with 0.1 mL markings are used to create phase behavior scans as well as run dilution experiments with aqueous solutions. Ends are sealed using a propane and oxygen flame.

Pipette Repeater: An Eppendorf Repeater Plus® instrument is used for most of the pipetting. This is a handheld dispenser calibrated to deliver between 25 microliter and 1 ml increments. Disposable tips are used to avoid contamination between stocks and allow for ease of operation and consistency.

Propane-oxygen Torch: A mixture of propane and oxygen gas is directed through a Bernz-O-Matic flame nozzle to create a hot flame about ½ inch long. This torch is used to flame-seal the glass pipettes used in phase behavior experiments.

Convection Ovens: Several convection ovens are used to incubate the phase behaviors and core flood experiments at the reservoir temperatures. The phase behavior pipettes are primarily kept in Blue M and Memmert ovens that are monitored with mercury thermometers and oven temperature gauges to ensure temperature fluctuations are kept at a minimal between recordings. A large custom built flow oven was used to house most of the core flood experiments and enabled fluid injection and collection to be done at reservoir temperature.

pH Meter: An ORION research model 701/digital ion analyzer with a pH electrode is used to measure the pH of most aqueous samples to obtain more accurate readings. This is calibrated with 4.0, 7.0 and 10.0 pH solutions. For rough measurements of pH, indicator papers are used with several drops of the sampled fluid.

Phase Behavior Calculations

The oil and water solubilization ratios are calculated from interface measurements taken from phase behavior pipettes. These interfaces are recorded over time as the mixtures approached equilibrium and the volume of any macroemulsions that initially formed decreased or disappeared.

Phase Behavior Methodology

The methods for creating, measuring and recording observations are described in this section. Scans are made using a variety of electrolyte mixtures described below. Oil is added to most aqueous surfactant solutions to see if a microemulsion formed, how long it took to form and equilibrate if it formed, what type of microemulsion formed and some of its properties such as viscosity. However, the behavior of aqueous mixtures without oil added is also important and is also done in some cases to determine if the aqueous solution is clear and stable over time, becomes cloudy or separated into more than one phase.

Preparation of samples. Phase behavior samples are made by first preparing surfactant stock solutions and combining them with brine stock solutions in order to observe the behavior of the mixtures over a range of salinities. All the experiments are created at or above 0.1 wt % active surfactant concentration, which is above the typical CMC of the surfactant.

Solution Preparation. Surfactant stocks are based on active weight-percent surfactant (and co-surfactant when incorporated). The masses of surfactant, co-surfactant, co-solvent and de-ionized water (DI) are measured out on a balance and mixed in glass jars using magnetic stir bars. The order of addition is recorded on a mixing sheet along with actual masses added and the pH of the final solution. Brine solutions are created at the necessary weight percent concentrations for making the scans.

Surfactant Stock. The chemicals being tested are first mixed in a concentrated stock solution that usually consisted of a primary surfactant, co-solvent and/or co-surfactant along with de-ionized water. The quantity of chemical added is calculated based on activity and measured by weight percent of total solution. Initial experiments are at about 1-3% active surfactant so that the volume of the middle microemulsion phase would be large enough for accurate measurements assuming a solubilization ratio of at least 10 at optimum salinity.

Polymer Stock. Often these stocks were quite viscous and made pipetting difficult so they are diluted with de-ionized water accordingly to improve ease of handling. Mixtures with polymer are made only for those surfactant formulations that showed good behavior and merited additional study for possible testing in core floods. Consequently, scans including polymer are limited since they are done only as a final evaluation of compatibility with the surfactant.

Pipetting Procedure. Phase behavior components are added volumetrically into 5 ml pipettes using an Eppendorf Repeater Plus or similar pipetting instrument. Surfactant and brine stocks are mixed with DI water into labeled pipettes and brought to temperature before agitation. Almost all of the phase behavior experiments are initially created with a water oil ratio (WOR) of 1:1, which involves mixing 2 ml of the aqueous phase with 2 ml of the evaluated crude oil or hydrocarbon, and different WOR experiments are mixed accordingly. The typical phase behavior scan consisted of 10-20 pipettes, each pipette being recognized as a data point in the series.

Order of Addition. Consideration must be given to the addition of the components since the concentrations are often several folds greater than the final concentration. Therefore, an order is established to prevent any adverse effects resulting from surfactant or polymer coming into direct contact with the concentrated electrolytes. The desired sample compositions are made by combining the stocks in the following order: (1) Electrolyte stock(s); (2) De-ionized water; (3) Surfactant stock; (4) Polymer stock; and (5) Crude oil or hydrocarbon. Any air bubbles trapped in the bottom of the pipettes are tapped out (prior to the addition of surfactant to avoid bubbles from forming).

Initial Observations. Once the components are added to the pipettes, sufficient time is allotted to allow all the fluid to drain down the sides. Then aqueous fluid levels are recorded before the addition of oil. These measurements are marked on record sheets. Levels and interfaces are recorded on these documents with comments over several days and additional sheets are printed as necessary.

Sealing and Mixing. The pipettes are blanketed with argon gas to prevent the ignition of any volatile gas present by the flame sealing procedure. The tubes are then sealed with the propane-oxygen torch to prevent loss of additional volatiles when placed in the oven. Pipettes are arranged on the racks to coincide with the change in the scan variable. Once the phase behavior scan is given sufficient time to reach reservoir temperature (15-30 minutes), the pipettes are inverted several times to provide adequate mixing. Tubes are observed for low tension upon mixing by looking at droplet size and how uniform the mixture appeared. Then the solutions are allowed to equilibrate over time and interface levels are recorded to determine equilibration time and surfactant performance.

Measurements and Observations. Phase behavior experiments are allowed to equilibrate in an oven that is set to the reservoir temperature for the crude oil being tested. The fluid levels in the pipettes are recorded periodically and the trend in the phase behavior observed over time. Equilibrium behavior is assumed when fluid levels ceased to change within the margin of error for reading the samples.

Fluid Interfaces. The fluid interfaces are the most crucial element of phase behavior experiments. From them, the phase volumes are determined and the solubilization ratios are calculated. The top and bottom interfaces are recorded as the scan transitioned from an oil-in-water microemulsion to a water-in-oil microemulsion. Initial readings are taken one day after initial agitation and sometimes within hours of agitation if coalescence appeared to happen rapidly. Measurements are taken thereafter at increasing time intervals (for example, one day, four days, one week, two weeks, one month and so on) until equilibrium is reached or the experiment is deemed unessential or uninteresting for continued observation.

V. References

U.S. Pat. No. 7,629,299: Process for Recovering Residual Oil Employing Alcohol Ether Sulfonates.

U.S. Patent Publication No. 20070191633: Mixed Anionic Surfactant Composition for Oil Recovery.

U.S. Patent Application No. 20100081716: Process for Production of Ether Carboxylates.

U.S. Pat. No. 6,225,267: Sodium Sulfonate Blends as Emulsifiers for Petroleum Oils.

U.S. Patent Application No. 20100048432: Enhanced Oil Recovery using Sulfonate Mixtures.

Anton R E et al. (2008): Practical Surfactant Mixing Rules Based on the Attainment of Microemulsion-Oil-Water Three-Phase Behavior Systems. Adv. Polym. Sci. 218:83-113

VI. Tables

TABLE 1

Phase behavior data recording sheet for the study described in FIG. 1.

| | | | | | |
|---|---|---|---|---|---|
| Experiment | HAC-20 0.5% Isofol-C32-15PO-10EO-SO4, 0.5% C11-ABS, 1% Na2CO3, Brine Scan with Oil # 1 (50% Oil) | | | | |
| Hydrocarbon | Oil # 1 | Hydrocarbon Density | g/cc | Typical hydrocarbon Densities: | |
| Surfactant | Isofol C32-15PO-10EO-SO4 | Total Surfactant Conc. | 1 wt % | Octane | |
| Co-Surfactant(1) | C11-ABS | Total Alcohol Conc. | 0 wt % | Decane | |
| Co-Solvent | | Polymer Conc. | 0 wt % | Mixed: Feb. 18, 2011 | |
| Surfactant Conc. | 0.5 | Na2CO3 Conc. | 0 wt % | | |
| Co-surf(1) Conc. | 0.5 wt % | WOR | 1 | | |
| t-pent Conc. | wt % | Temperature | 100 Celcius | | |
| alkali | varied wt % | Tube Size | 5 mL | | |
| NaCl:CaCl Ratio | | | | | |

| Salinity (% of Brine) | TDS in ppm (from Brine + Na2CO3) | Aqueous Level | Hydrocarbon Level | Top of emulsion | Top Interface | Bottom Interface | Bottom of emulsion | Type | Volume of Oil Solublized (cc) |
|---|---|---|---|---|---|---|---|---|---|
| | Mar. 23, 2011 | | | | | 33 days | | | |
| 0.00% | 10000 | 2.92 | 0.9 | | 2.80 | | | I | 0.12 |
| 10.00% | 16000 | 2.92 | 0.9 | | 2.80 | | | I | 0.12 |
| 20.00% | 22000 | 2.93 | 0.9 | | 2.80 | | | I | 0.13 |
| 30.00% | 28000 | 3.00 | 0.9 | | 2.80 | | | I | 0.20 |
| 40.00% | 34000 | 2.92 | 0.9 | | 2.30 | 4.80 | | III | 0.62 |
| 50.00% | 40000 | 2.95 | 0.9 | | 1.00 | 3.12 | | III | 1.95 |
| 60.00% | 46000 | 2.91 | 0.9 | | | 3.00 | | II | 2.91 |
| 70.00% | 52000 | 2.91 | 0.9 | | | 2.95 | | II | 2.91 |
| 80.00% | 58000 | 2.92 | 0.9 | | | 2.92 | | II | 2.92 |
| 90.00% | 64000 | 2.92 | 0.9 | | | 2.92 | | II | 2.92 |
| | Mar. 3, 2011 | | | | | 13 days | | | |
| 0.00% | 10000 | 2.92 | 0.9 | | 2.82 | | | I | 0.10 |
| 10.00% | 16000 | 2.92 | 0.9 | | 2.82 | | | I | 0.10 |
| 20.00% | 22000 | 2.93 | 0.9 | | 2.80 | | | I | 0.13 |
| 30.00% | 28000 | 3.00 | 0.9 | | 2.80 | | | I | 0.20 |
| 40.00% | 34000 | 2.92 | 0.9 | | 2.30 | 4.80 | | III | 0.62 |
| 50.00% | 40000 | 2.95 | 0.9 | | 0.90 | 3.15 | | III | 2.05 |
| 60.00% | 46000 | 2.91 | 0.9 | | | 3.00 | | II | 2.91 |
| 70.00% | 52000 | 2.91 | 0.9 | | | 2.95 | | II | 2.91 |
| 80.00% | 58000 | 2.92 | 0.9 | | | 2.92 | | II | 2.92 |
| 90.00% | 64000 | 2.92 | 0.9 | | | 2.92 | | II | 2.92 |

| Salinity (% of Brine) | Volume of Water Solublized (cc) | Oil Sol. Ratio (cc/cc) | Water Sol. Ratio (cc/cc) | HC Sol. (mg/L) | Volume Fraction of Oil (Vo) | Volumn Fraction of Microemulsion (Vme) | Volumn Fraction of Water (Vw) | Vw + Vme |
|---|---|---|---|---|---|---|---|---|
| | | | 33 days | | | | | |
| 0.00% | | 5.8 | | 0 | 0.463 | 0.537 | 0.000 | 0.537 |
| 10.00% | | 5.8 | | 0 | 0.463 | 0.537 | 0.000 | 0.537 |
| 20.00% | | 6.3 | | 0 | 0.463 | 0.537 | 0.000 | 0.537 |
| 30.00% | | 10.0 | | 0 | 0.463 | 0.537 | 0.000 | 0.537 |
| 40.00% | 1.88 | 29.8 | 90.4 | 0 | 0.341 | 0.610 | 0.049 | 0.659 |
| 50.00% | 0.17 | 95.1 | 8.3 | 0 | 0.024 | 0.517 | 0.459 | 0.976 |
| 60.00% | 0.09 | | 4.3 | NA | 0 | 0.512 | 0.488 | 1.000 |
| 70.00% | 0.04 | | 1.9 | NA | 0 | 0.500 | 0.500 | 1.000 |
| 80.00% | 0.00 | | 0.0 | NA | 0 | 0.493 | 0.507 | 1.000 |
| 90.00% | 0.00 | | 0.0 | NA | 0 | 0.493 | 0.507 | 1.000 |
| | | | 13 days | | | | | |
| 0.00% | | 4.8 | | 0 | 0.468 | 0.532 | 0.000 | 0.532 |
| 10.00% | | 4.8 | | 0 | 0.468 | 0.532 | 0.000 | 0.532 |
| 20.00% | | 6.3 | | 0 | 0.463 | 0.537 | 0.000 | 0.537 |
| 30.00% | | 10.0 | | 0 | 0.463 | 0.537 | 0.000 | 0.537 |
| 40.00% | 1.88 | 29.8 | 90.4 | 0 | 0.341 | 0.610 | 0.049 | 0.659 |
| 50.00% | 0.20 | 100.0 | 9.8 | 0 | 0.000 | 0.549 | 0.451 | 1.000 |

TABLE 1-continued

Phase behavior data recording sheet for the study described in FIG. 1.

| | | | | | | | |
|---|---|---|---|---|---|---|---|
| 60.00% | 0.09 | 4.3 | NA | 0 | 0.512 | 0.488 | 1.000 |
| 70.00% | 0.04 | 1.9 | NA | 0 | 0.500 | 0.500 | 1.000 |
| 80.00% | 0.00 | 0.0 | NA | 0 | 0.493 | 0.507 | 1.000 |
| 90.00% | 0.00 | 0.0 | NA | 0 | 0.493 | 0.507 | 1.000 |

TABLE 2

Figure 2:
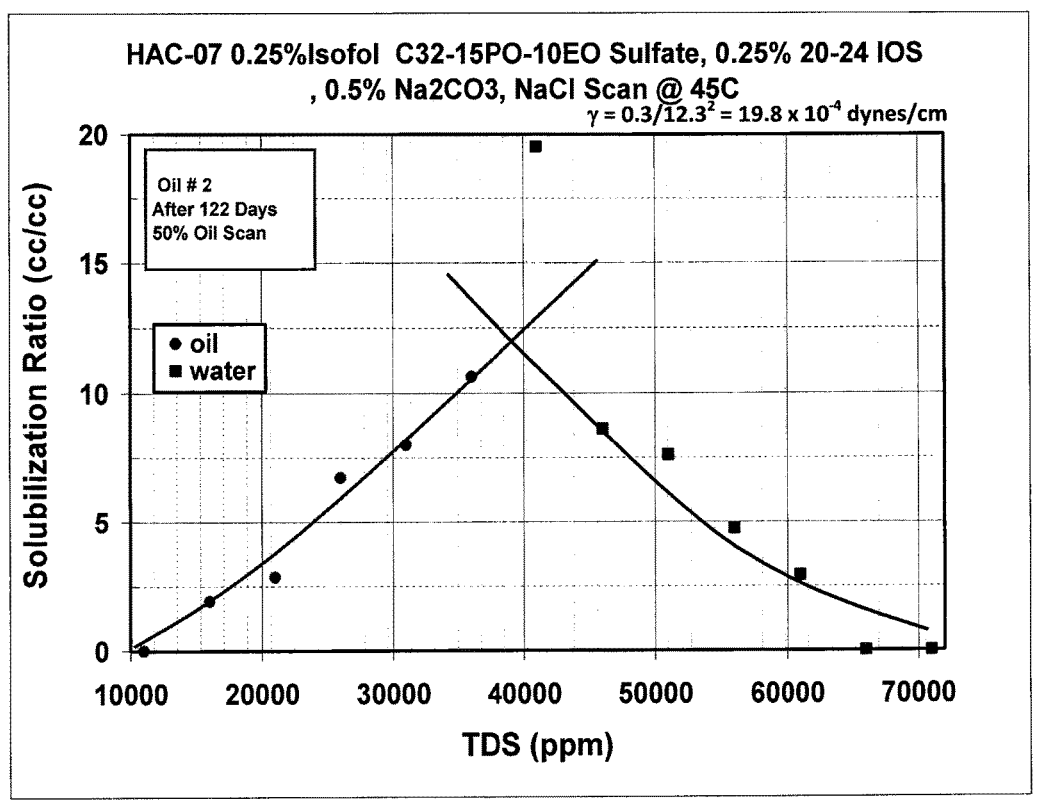
FIG. 2. Phase behavior plot for a study with HAC-07 0.25% Isofol (Guerbet) C32-15PO-10EO SO4, 0.25% 20-24 IOS (Internal olefin sulfonate), 0.5% $Na_2CO_3$, NaCl Scan at 45° C. (a control study).

Phase behavior data recording sheet for the study described in FIG. 2.

| | | | | | |
|---|---|---|---|---|---|
| Experiment | HAC-07 0.25% Isofol C32-15PO-10EO SO4, 0.25% petrostep S3B, 0.5% Na2CO3 in HLCRB with 30% decaline-50% oil | | | | |
| Hydrocarbon | Oil # 2 | Hydrocarbon Density | | g/cc | Typical hydrocarbon Densities: |
| Surfactant | Isofol C32-15PO-10EO SO4 | Total Surfactant Conc. | 0.5 | wt % | Octane |
| Co-Surfactant(1) | C20-24 IOS | Total Co-solvent Conc. | 0 | wt % | Decane |
| Co-Solvent | | | | | Mixed: Sep. 13, 2010 |
| Surfactant Conc. | 0.25 | wt % | Polymer Conc. | 0 | wt % |
| Co-surf(1) Conc. | 0.25 | wt % | Na2CO3 Conc. | 0 | wt % |
| t-pent Conc. | | wt % | WOR | 1 | |
| Butanol 2.15 | | wt % | Temperature | 45 | Celcius |
| EO | | | Tube Size | 5 | mL |
| NaCl:CaCl Ratio | | | | | |

| Salinity (wt % NaC;) | TDS (ppm) | Aqueous Level | Hydrocarbon Level | Top of emulsion | Top Interface | Bottom Interface | Bottom of emulsion | Type | Volume of Oil Solublized (cc) |
|---|---|---|---|---|---|---|---|---|---|
| | | Jan. 13, 2011 | | | | 122 days | | | |
| 0.50% | 11000 | 2.90 | | | 2.90 | | | I | 0.00 |
| 1.00% | 16000 | 2.92 | | | 2.90 | | | I | 0.02 |
| 1.50% | 21000 | 2.90 | | | 2.87 | | | I | 0.03 |
| 2.00% | 26000 | 2.92 | | | 2.85 | | | I | 0.07 |
| 2.50% | 31000 | 3.00 | | | 2.92 | | | I | 0.08 |
| 3.00% | 36000 | 2.93 | | | 2.82 | | | I | 0.11 |
| 3.50% | 41000 | 2.95 | | | | 3.15 | | II | 2.95 |
| 4.00% | 46000 | 2.91 | | | | 3.00 | | II | 2.91 |
| 4.50% | 51000 | 2.90 | | | | 2.98 | | II | 2.90 |
| 5.00% | 56000 | 2.90 | | | | 2.95 | | II | 2.90 |
| 5.50% | 61000 | 2.95 | | | | 2.98 | | II | 2.95 |
| 6.00% | 66000 | 3.00 | | | | 3.00 | | II | 3.00 |
| 6.50% | 71000 | 2.90 | | | | 2.90 | | II | 2.90 |
| | | Nov. 16, 2010 | | | | 64 days | | | |
| 0.50% | 11000 | 2.90 | | | 2.90 | | | I | 0.00 |
| 1.00% | 16000 | 2.92 | | | 2.90 | | | I | 0.02 |
| 1.50% | 21000 | 2.90 | | | 2.85 | | | I | 0.05 |
| 2.00% | 26000 | 2.92 | | | 2.85 | | | I | 0.07 |
| 2.50% | 31000 | 3.00 | | | 2.90 | | | I | 0.10 |
| 3.00% | 36000 | 2.93 | | | 2.80 | | | I | 0.13 |
| 3.50% | 41000 | 2.95 | | | | 3.20 | | II | 2.95 |
| 4.00% | 46000 | 2.91 | | | | 3.02 | | II | 2.91 |
| 4.50% | 51000 | 2.90 | | | | 3.00 | | II | 2.90 |
| 5.00% | 56000 | 2.90 | | | | 3.00 | | II | 2.90 |
| 5.50% | 61000 | 2.95 | | | | 2.98 | | II | 2.95 |
| 6.00% | 66000 | 3.00 | | | | 3.00 | | II | 3.00 |
| 6.50% | 71000 | 2.90 | | | | 2.90 | | II | 2.90 |

| Salinity (wt % NaC;) | Volume of Water Solublized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ |
|---|---|---|---|---|---|---|---|---|
| | | | | 122 days | | | | |
| 0.50% | | 0.0 | | 0 | 0.580 | 0.420 | 0.000 | 0.420 |
| 1.00% | | 1.9 | | 0 | 0.580 | 0.420 | 0.000 | 0.420 |
| 1.50% | | 2.9 | | 0 | 0.574 | 0.426 | 0.000 | 0.426 |
| 2.00% | | 6.7 | | 0 | 0.570 | 0.430 | 0.000 | 0.430 |
| 2.50% | | 8.0 | | 0 | 0.584 | 0.416 | 0.000 | 0.416 |
| 3.00% | | 10.6 | | 0 | 0.564 | 0.436 | 0.000 | 0.436 |
| 3.50% | 0.20 | | 19.5 | NA | 0 | 0.630 | 0.370 | 1.000 |
| 4.00% | 0.09 | | 8.6 | NA | 0 | 0.600 | 0.400 | 1.000 |
| 4.50% | 0.08 | | 7.6 | NA | 0 | 0.596 | 0.404 | 1.000 |
| 5.00% | 0.05 | | 4.8 | NA | 0 | 0.590 | 0.410 | 1.000 |
| 5.50% | 0.03 | | 2.9 | NA | 0 | 0.596 | 0.404 | 1.000 |

TABLE 2-continued

Phase behavior data recording sheet for the study described in FIG. 2.

| | | | | | | | | |
|---|---|---|---|---|---|---|---|---|
| 6.00% | 0.00 | | 0.0 | NA | 0 | 0.600 | 0.400 | 1.000 |
| 6.50% | 0.00 | | 0.0 | NA | 0 | 0.580 | 0.420 | 1.000 |
| | | | | 64 days | | | | |
| 0.50% | | 0.0 | | 0 | 0.580 | 0.420 | 0.000 | 0.420 |
| 1.00% | | 1.9 | | 0 | 0.580 | 0.420 | 0.000 | 0.420 |
| 1.50% | | 4.8 | | 0 | 0.570 | 0.430 | 0.000 | 0.430 |
| 2.00% | | 6.7 | | 0 | 0.570 | 0.430 | 0.000 | 0.430 |
| 2.50% | | 10.0 | | 0 | 0.580 | 0.420 | 0.000 | 0.420 |
| 3.00% | | 12.6 | | 0 | 0.560 | 0.440 | 0.000 | 0.440 |
| 3.50% | 0.25 | | 24.4 | NA | 0 | 0.640 | 0.360 | 1.000 |
| 4.00% | 0.11 | | 10.5 | NA | 0 | 0.604 | 0.396 | 1.000 |
| 4.50% | 0.10 | | 9.5 | NA | 0 | 0.600 | 0.400 | 1.000 |
| 5.00% | 0.10 | | 9.5 | NA | 0 | 0.600 | 0.400 | 1.000 |
| 5.50% | 0.03 | | 2.9 | NA | 0 | 0.596 | 0.404 | 1.000 |
| 6.00% | 0.00 | | 0.0 | NA | 0 | 0.600 | 0.400 | 1.000 |
| 6.50% | 0.00 | | 0.0 | NA | 0 | 0.580 | 0.420 | 1.000 |

TABLE 3

Figure 3:
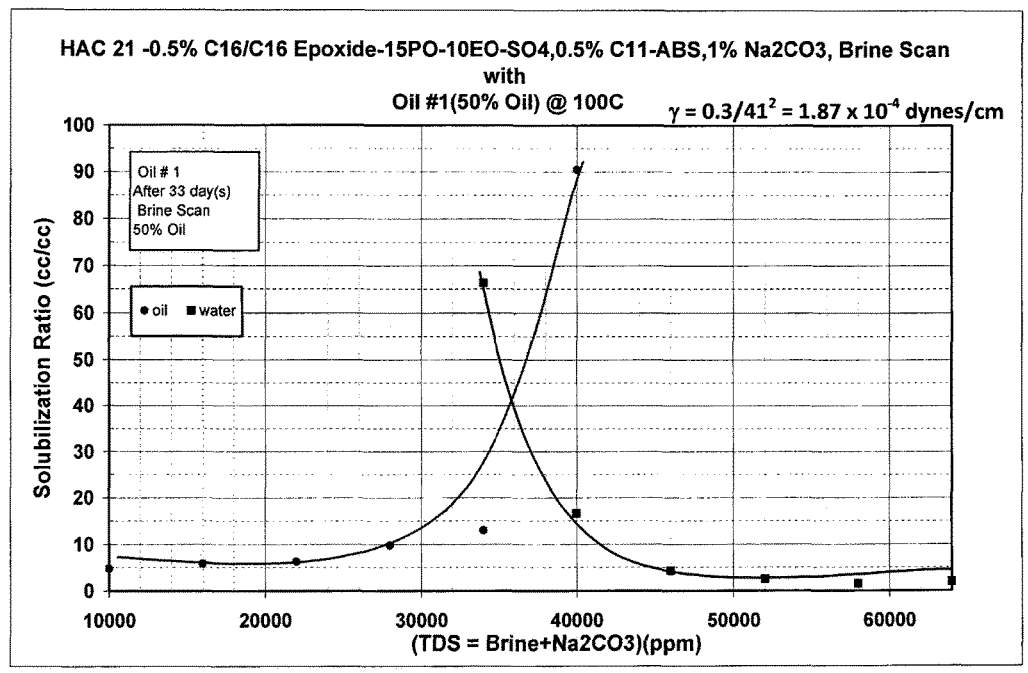
FIG. 3. Phase behavior plot for a study with HAC-21 0.5% C16 alcohol/C16 Epoxide-15PO-10EO-SO4, 0.5% C11-ABS, 1% Na2CO3, Brine Scan with Oil #1(50% Oil) at 100° C.

Phase behavior data recording sheet for the study described in FIG. 3.

| | | | | | |
|---|---|---|---|---|---|
| Experiment | HAC 21-0.5% C16/C16 Epoxide-15PO-10EO-SO4, 0.5% C11-ABS, 1% Na2CO3, Brine Scan with Oil # 1 (50% Oil) @ 100 C. | | | | |
| Hydrocarbon | Oil # 1 | Hydrocarbon Density | | g/cc | Typical hydrocarbon Densities: |
| Surfactant | C16/C16 Epoxide-15PO-10EO-SO4 | Total Surfactant Conc. | 1 | wt % | Octane |
| Co-Surfactant(1) | C11-ABS | Total Alcohol Conc. | 0 | wt % | Decane |
| Co-Solvent | | Polymer Conc. | 0 | wt % | Mixed: Feb. 18, 2011 |
| Surfactant Conc. | 0.5 | Na2CO3 Conc. | 0 | wt % | |
| Co-surf(1) Conc. | 0.5 | wt % | WOR | 1 | |
| t-pent Conc. | | wt % | Temperature | 100 | Celcius |
| alkali | varied | wt % | Tube Size | 5 | mL |
| NaCl:CaCl Ratio | | | | | |

| Salinity (% of Brine) | TDS in ppm (from Brine + Na2CO3) | Aqueous Level | Hydrocarbon Level | Top of emulsion | Top Interface | Bottom Interface | Bottom of emulsion | Type |
|---|---|---|---|---|---|---|---|---|
| | | Mar. 23, 2011 | | | 33 days | | | |
| 0.00% | 10000 | 2.90 | 0.9 | | 2.80 | | | I |
| 10.00% | 16000 | 2.92 | 0.9 | | 2.80 | | | I |
| 20.00% | 22000 | 2.91 | 0.9 | | 2.78 | | | I |
| 30.00% | 28000 | 2.95 | 0.9 | | 2.75 | | | I |
| 40.00% | 34000 | 2.92 | 0.9 | | 2.65 | 4.30 | | III |
| 50.00% | 40000 | 2.90 | 0.9 | | 1.00 | 3.25 | | III |
| 60.00% | 46000 | 2.91 | 0.9 | | | 3.00 | | II |
| 70.00% | 52000 | 2.95 | 0.9 | | | 3.00 | | II |
| 80.00% | 58000 | 2.92 | 0.9 | | | 2.95 | | II |
| 90.00% | 64000 | 2.91 | 0.9 | | | 2.95 | | II |
| | | Mar. 3, 2011 | | | 13 days | | | |
| 0.00% | 10000 | 2.90 | 0.9 | | 2.80 | | | I |
| 10.00% | 16000 | 2.92 | 0.9 | | 2.80 | | | I |
| 20.00% | 22000 | 2.91 | 0.9 | | 2.78 | | | I |
| 30.00% | 28000 | 2.95 | 0.9 | | 2.62 | | | I |
| 40.00% | 34000 | 2.92 | 0.9 | | 1.90 | 4.25 | | III |
| 50.00% | 40000 | 2.90 | 0.9 | | 1.00 | 3.15 | | III |
| 60.00% | 46000 | 2.91 | 0.9 | | | 3.00 | | II |
| 70.00% | 52000 | 2.95 | 0.9 | | | 3.00 | | II |
| 80.00% | 58000 | 2.92 | 0.9 | | | 2.95 | | II |
| 90.00% | 64000 | 2.91 | 0.9 | | | 2.95 | | II |

| Salinity (% of Brine) | Volume of Oil Solublized (cc) | Volume of Water Solublized (cc) | Oil Sol. Ratio (cc/cc) | Water Sol. Ratio (cc/cc) | HC Sol. (mg/L) | Volume Fraction of Oil (Vo) | Volumn Fraction of Microemulsion (Vme) | Volumn Fraction of Water (Vw) | Vw + Vme |
|---|---|---|---|---|---|---|---|---|---|
| | | | | 33 days | | | | | |
| 0.00% | 0.10 | | 4.8 | | 0 | 0.463 | 0.537 | 0.000 | 0.537 |
| 10.00% | 0.12 | | 5.8 | | 0 | 0.463 | 0.537 | 0.000 | 0.537 |
| 20.00% | 0.13 | | 6.2 | | 0 | 0.459 | 0.541 | 0.000 | 0.541 |
| 30.00% | 0.20 | | 9.8 | | 0 | 0.451 | 0.549 | 0.000 | 0.549 |
| 40.00% | 0.27 | 1.38 | 13.0 | 66.3 | 0 | 0.427 | 0.402 | 0.171 | 0.573 |
| 50.00% | 1.90 | 0.35 | 90.5 | 16.7 | 0 | 0.024 | 0.549 | 0.427 | 0.976 |
| 60.00% | 2.91 | 0.09 | | 4.3 | NA | 0 | 0.512 | 0.488 | 1.000 |
| 70.00% | 2.95 | 0.05 | | 2.4 | NA | 0 | 0.512 | 0.488 | 1.000 |

TABLE 3-continued

Phase behavior data recording sheet for the study described in FIG. 3.

| | | | | | | | | | |
|---|---|---|---|---|---|---|---|---|---|
| 80.00% | 2.92 | 0.03 | | 1.4 | NA | 0 | 0.500 | 0.500 | 1.000 |
| 90.00% | 2.91 | 0.04 | | 1.9 | NA | 0 | 0.500 | 0.500 | 1.000 |
| | | | | 13 days | | | | | |
| 0.00% | 0.10 | | 4.8 | | | 0 | 0.463 | 0.537 | 0.000 | 0.537 |
| 10.00% | 0.12 | | 5.8 | | | 0 | 0.463 | 0.537 | 0.000 | 0.537 |
| 20.00% | 0.13 | | 6.2 | | | 0 | 0.459 | 0.541 | 0.000 | 0.541 |
| 30.00% | 0.33 | | 16.1 | | | 0 | 0.420 | 0.580 | 0.000 | 0.580 |
| 40.00% | 1.02 | 1.33 | 49.0 | 63.9 | | 0 | 0.244 | 0.573 | 0.183 | 0.756 |
| 50.00% | 1.90 | 0.25 | 90.5 | 11.9 | | 0 | 0.024 | 0.524 | 0.451 | 0.976 |
| 60.00% | 2.91 | 0.09 | | 4.3 | NA | 0 | 0.512 | 0.488 | 1.000 |
| 70.00% | 2.95 | 0.05 | | 2.4 | NA | 0 | 0.512 | 0.488 | 1.000 |
| 80.00% | 2.92 | 0.03 | | 1.4 | NA | 0 | 0.500 | 0.500 | 1.000 |
| 90.00% | 2.91 | 0.04 | | 1.9 | NA | 0 | 0.500 | 0.500 | 1.000 |

TABLE 4

Figure 4:
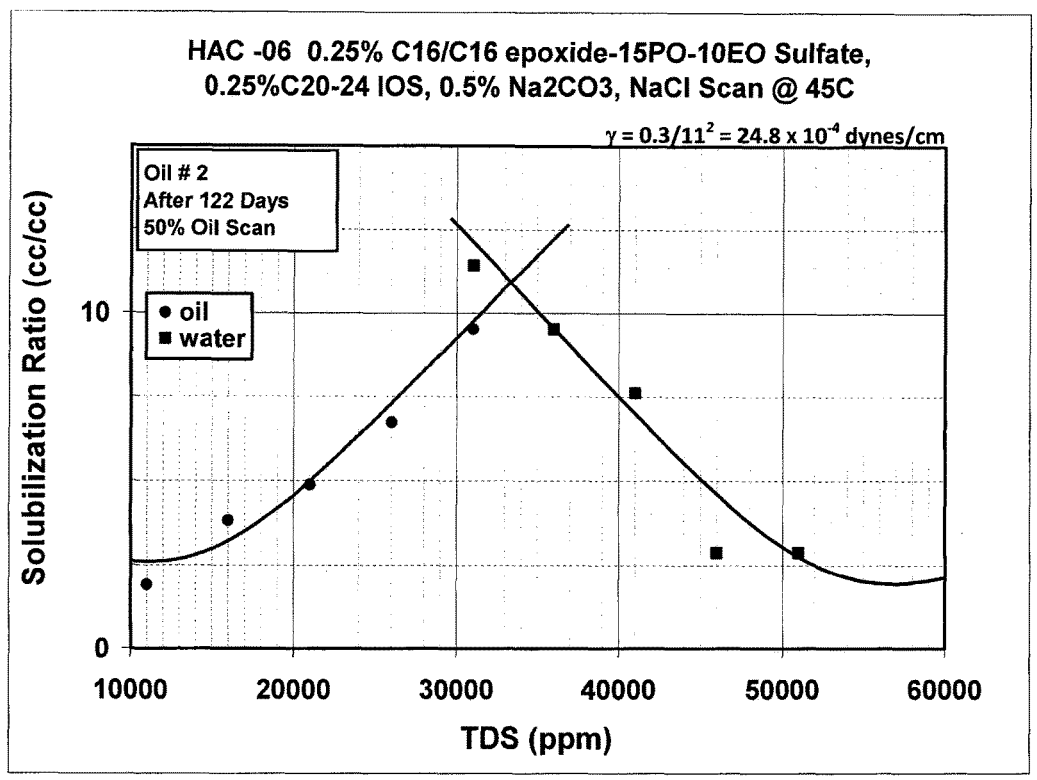
FIG. 4. Phase behavior plot for a study with HAC-06 0.25% C16 alcohol/C16 epoxide-15PO-10EO SO4, 0.25% C20-24 IOS, 0.5% $Na_2CO_3$, NaCl Scan at 45° C.

Phase behavior data recording sheet for the study described in FIG. 4.

| | | | | |
|---|---|---|---|---|
| Experiment | HAC-06 0.25% C16/C16 Epoxide-15PO-10EO SO4, 0.25% C20-24 IOS, 0.5% Na2CO3, NaCl Scan in Brine # 2 with Oil # 2 (50% Oil) | | | |
| Hydrocarbon | Oil # 2 | Hydrocarbon Density | g/cc | Typical hydrocarbon Densities: |
| Surfactant | C16/C16 Epoxide-15PO-10EO SO4 | Total Surfactant Conc. | 0.5 wt % | Octane |
| Co-Surfactant(1) | C20-24 IOS | Total Co-solvent Conc. | 0 wt % | Decane |
| Co-Solvent | | Polymer Conc. | 0 wt % | Mixed: Sep. 13, 2010 |
| Surfactant Conc. | 0.25 wt % | Na2CO3 Conc. | 0 wt % | |
| Co-surf(1) Conc. | 0.25 wt % | WOR | 1 | |
| t-pent Conc. | wt % | Temperature | 45 Celcius | |
| Butanol 2.15 EO | wt % | Tube Size | 5 mL | |
| NaCl:CaCl Ratio | | | | |

| Salinity (wt % NaC;) | TDS (ppm) | Aqueous Level | Hydrocarbon Level | Top of emulsion | Top Interface | Bottom Interface | Bottom of emulsion | Type | Volume of Oil Solublized (cc) | Volume of Water Solublized (cc) |
|---|---|---|---|---|---|---|---|---|---|---|
| | | Jan. 13, 2011 | | | | 122 days | | | | |
| 0.50% | 11000 | 2.90 | | | 2.88 | | | I | 0.02 | |
| 1.00% | 16000 | 2.91 | | | 2.87 | | | I | 0.04 | |
| 1.50% | 21000 | 2.95 | | | 2.90 | | | I | 0.05 | |
| 2.00% | 26000 | 2.92 | | | 2.85 | | | I | 0.07 | |
| 2.50% | 31000 | 2.90 | | | 2.80 | 3.02 | | III | 0.10 | 0.12 |
| 3.00% | 36000 | 2.90 | | | | 3.00 | | II | 2.90 | 0.10 |
| 3.50% | 41000 | 2.90 | | | | 2.98 | | II | 2.90 | 0.08 |
| 4.00% | 46000 | 2.92 | | | | 2.95 | | II | 2.92 | 0.03 |
| 4.50% | 51000 | 2.92 | | | | 2.95 | | II | 2.92 | 0.03 |
| | | Nov. 16, 2010 | | | | 64 days | | | | |
| 0.50% | 11000 | 2.90 | | | 2.90 | | | I | 0.00 | |
| 1.00% | 16000 | 2.91 | | | 2.90 | | | I | 0.01 | |
| 1.50% | 21000 | 2.95 | | | 2.90 | | | I | 0.05 | |
| 2.00% | 26000 | 2.92 | | | 2.85 | | | I | 0.07 | |
| 2.50% | 31000 | 2.90 | | | 2.80 | 3.01 | | III | 0.10 | 0.11 |
| 3.00% | 36000 | 2.90 | | | | 2.95 | | II | 2.90 | 0.05 |
| 3.50% | 41000 | 2.90 | | | | 2.98 | | II | 2.90 | 0.08 |
| 4.00% | 46000 | 2.92 | | | | 2.95 | | II | 2.92 | 0.03 |
| 4.50% | 51000 | 2.92 | | | | 2.95 | | II | 2.92 | 0.03 |

| Salinity (wt % NaC;) | TDS (ppm) | Aqueous Level | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ |
|---|---|---|---|---|---|---|---|---|---|
| | | Jan. 13, 2011 | | | | 122 days | | | |
| 0.50% | 11000 | 2.90 | 1.9 | | 0 | 0.576 | 0.424 | 0.000 | 0.424 |
| 1.00% | 16000 | 2.91 | 3.8 | | 0 | 0.574 | 0.426 | 0.000 | 0.426 |
| 1.50% | 21000 | 2.95 | 4.9 | | 0 | 0.580 | 0.420 | 0.000 | 0.420 |
| 2.00% | 26000 | 2.92 | 6.7 | | 0 | 0.570 | 0.430 | 0.000 | 0.430 |
| 2.50% | 31000 | 2.90 | 9.5 | 11.4 | 0 | 0.560 | 0.044 | 0.396 | 0.440 |
| 3.00% | 36000 | 2.90 | | 9.5 | NA | 0 | 0.600 | 0.400 | 1.000 |
| 3.50% | 41000 | 2.90 | | 7.6 | NA | 0 | 0.596 | 0.404 | 1.000 |
| 4.00% | 46000 | 2.92 | | 2.9 | NA | 0 | 0.590 | 0.410 | 1.000 |
| 4.50% | 51000 | 2.92 | | 2.9 | NA | 0 | 0.590 | 0.410 | 1.000 |
| | | Nov. 16, 2010 | | | | 64 days | | | |
| 0.50% | 11000 | 2.90 | 0.0 | | 0 | 0.580 | 0.420 | 0.000 | 0.420 |
| 1.00% | 16000 | 2.91 | 1.0 | | 0 | 0.580 | 0.420 | 0.000 | 0.420 |

TABLE 4-continued

Phase behavior data recording sheet for the study described in FIG. 4.

| | | | | | | | | | |
|---|---|---|---|---|---|---|---|---|---|
| 1.50% | 21000 | 2.95 | 4.9 | | 0 | 0.580 | 0.420 | 0.000 | 0.420 |
| 2.00% | 26000 | 2.92 | 6.7 | | 0 | 0.570 | 0.430 | 0.000 | 0.430 |
| 2.50% | 31000 | 2.90 | 9.5 | 10.5 | 0 | 0.560 | 0.042 | 0.398 | 0.440 |
| 3.00% | 36000 | 2.90 | | 4.8 | NA | 0 | 0.590 | 0.410 | 1.000 |
| 3.50% | 41000 | 2.90 | | 7.6 | NA | 0 | 0.596 | 0.404 | 1.000 |
| 4.00% | 46000 | 2.92 | | 2.9 | NA | 0 | 0.590 | 0.410 | 1.000 |
| 4.50% | 51000 | 2.92 | | 2.9 | NA | 0 | 0.590 | 0.410 | 1.000 |

TABLE 5

Figure 5:
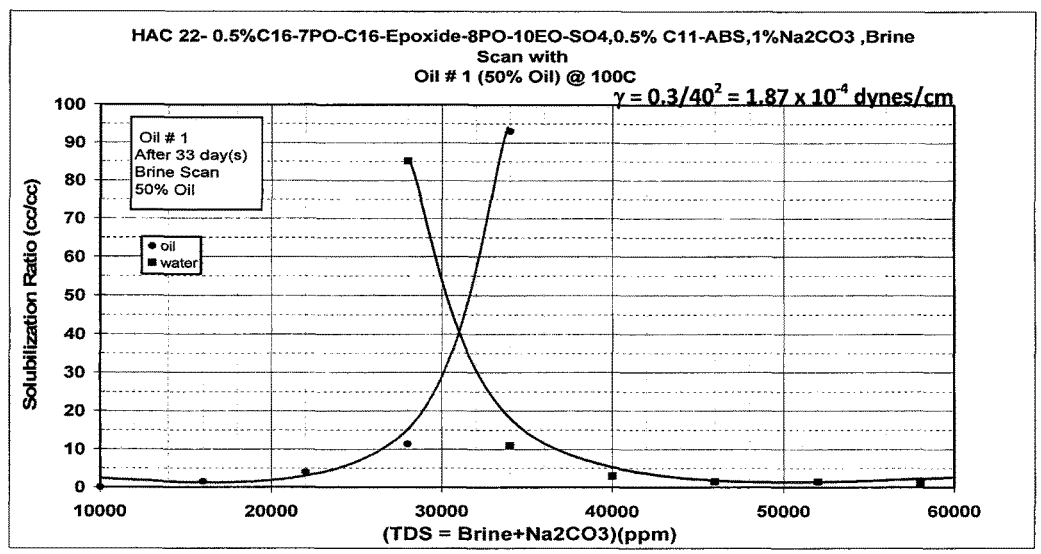
FIG. 5. Phase behavior plot for a study with HAC-22 0.5% C16-7PO alkoxylate/C16 Epoxide-8PO-10EO-SO4, 0.5% C11-ABS, 1% $Na_2CO_3$, Brine Scan with Oil #1 (50% Oil) at 100° C.

Phase behavior data recording sheet for the study described in FIG. 5.

| | | | | |
|---|---|---|---|---|
| Experiment | HAC 22-0.5% C16-7PO-C16-Epoxide-8PO-10EO-SO4, 0.5% C11-ABS, 1% Na2CO3, Brine Scan with Oil # 1 (50% Oil) @ 100 C. | | | |
| Hydrocarbon | Oil # 1 | Hydrocarbon Density | g/cc | Typical hydrocarbon Densities: |
| Surfactant | C16-7PO-C16-8PO-10EO-SO4 | Total Surfactant Conc. | 1 wt % | Octane |
| | | Total Alcohol Conc. | 0 wt % | Decane |
| Co-Surfactant(1) | C11-ABS | Polymer Conc. | 0 wt % | Mixed: Feb. 18, 2011 |
| Co-Solvent | | Na2CO3 Conc. | 0 wt % | |
| Surfactant Conc. | 0.5 | WOR | 1 | |
| Co-surf(1) Conc. | 0.5 wt % | Temperature | 100 Celcius | |
| t-pent Conc. | wt % | Tube Size | 5 mL | |
| alkali | varied wt % | | | |
| NaCl:CaCl Ratio | | | | |

| Salinity (% of Brine) | TDS in ppm (from Brine + Na2CO3) | Aqueous Level | Hydrocarbon Level | Top of emulsion | Top Interface | Bottom Interface | Bottom of emulsion | Type | Volume of Oil Solublized (cc) |
|---|---|---|---|---|---|---|---|---|---|
| | | Mar. 23, 2011 | | | | | 33 days | | |
| 0.00% | 10000 | 2.98 | 0.9 | | 2.98 | | | I | 0.00 |
| 10.00% | 16000 | 2.98 | 0.9 | | 2.95 | | | I | 0.03 |
| 20.00% | 22000 | 2.98 | 0.9 | | 2.90 | | | I | 0.08 |
| 30.00% | 28000 | 2.98 | 0.9 | | 2.75 | 4.70 | | III | 0.23 |
| 40.00% | 34000 | 2.98 | 0.9 | | 1.10 | 3.20 | | III | 1.88 |
| 50.00% | 40000 | 2.99 | 0.9 | | | 3.05 | | II | 2.99 |
| 60.00% | 46000 | 2.99 | 0.9 | | | 3.02 | | II | 2.99 |
| 70.00% | 52000 | 2.97 | 0.9 | | | 3.00 | | II | 2.97 |
| 80.00% | 58000 | 2.98 | 0.9 | | | 3.00 | | II | 2.98 |
| 90.00% | 64000 | 2.99 | 0.9 | | | 3.00 | | II | 2.99 |
| | | Feb. 18, 2011 | | | | | 0 days | | |
| 0.00% | 10000 | 2.98 | 0.9 | | 2.98 | | | I | 0.00 |
| 10.00% | 16000 | 2.98 | 0.9 | | 2.95 | | | I | 0.03 |
| 20.00% | 22000 | 2.98 | 0.9 | | 2.90 | | | I | 0.08 |
| 30.00% | 28000 | 2.98 | 0.9 | | 2.75 | 4.80 | | III | 0.23 |
| 40.00% | 34000 | 2.98 | 0.9 | | 1.05 | 3.50 | | III | 1.93 |
| 50.00% | 40000 | 2.99 | 0.9 | | | 3.05 | | II | 2.99 |
| 60.00% | 46000 | 2.99 | 0.9 | | | 3.02 | | II | 2.99 |
| 70.00% | 52000 | 2.97 | 0.9 | | | 3.00 | | II | 2.97 |
| 80.00% | 58000 | 2.98 | 0.9 | | | 3.00 | | II | 2.98 |
| 90.00% | 64000 | 2.99 | 0.9 | | | 3.00 | | II | 2.99 |

| Salinity (% of Brine) | TDS in ppm (from Brine + Na2CO3) | Aqueous Level | Volume of Water Solublized (cc) | Oil Sol. Ratio (cc/cc) | Water Sol. Ratio (cc/cc) | HC Sol. (mg/L) | Volume Fraction of Oil (Vo) | Volume Fraction of Microemulsion (Vme) | Volumn Fraction of Water (Vw) | Vw + Vme |
|---|---|---|---|---|---|---|---|---|---|---|
| | | Mar. 23, 2011 | | | | | 33 days | | | |
| 0.00% | 10000 | 2.98 | | 0.0 | | 0 | 0.507 | 0.493 | 0.000 | 0.493 |
| 10.00% | 16000 | 2.98 | | 1.5 | | 0 | 0.500 | 0.500 | 0.000 | 0.500 |
| 20.00% | 22000 | 2.98 | | 4.0 | | 0 | 0.488 | 0.512 | 0.000 | 0.512 |
| 30.00% | 28000 | 2.98 | 1.72 | 11.4 | 85.1 | 0 | 0.451 | 0.476 | 0.073 | 0.549 |
| 40.00% | 34000 | 2.98 | 0.22 | 93.1 | 10.9 | 0 | 0.049 | 0.512 | 0.439 | 0.951 |
| 50.00% | 40000 | 2.99 | 0.06 | | 3.0 | NA | 0 | 0.524 | 0.476 | 1.000 |
| 60.00% | 46000 | 2.99 | 0.03 | | 1.5 | NA | 0 | 0.517 | 0.483 | 1.000 |
| 70.00% | 52000 | 2.97 | 0.03 | | 1.5 | NA | 0 | 0.512 | 0.488 | 1.000 |
| 80.00% | 58000 | 2.98 | 0.02 | | 1.0 | NA | 0 | 0.512 | 0.488 | 1.000 |
| 90.00% | 64000 | 2.99 | 0.01 | | 0.5 | NA | 0 | 0.512 | 0.488 | 1.000 |
| | | Feb. 18, 2011 | | | | | 0 days | | | |
| 0.00% | 10000 | 2.98 | | 0.0 | | 0 | 0.507 | 0.493 | 0.000 | 0.493 |

TABLE 5-continued

Phase behavior data recording sheet for the study described in FIG. 5.

| | | | | | | | | | | |
|---|---|---|---|---|---|---|---|---|---|---|
| 10.00% | 16000 | 2.98 | | 1.5 | | 0 | 0.500 | 0.500 | 0.000 | 0.500 |
| 20.00% | 22000 | 2.98 | | 4.0 | | 0 | 0.488 | 0.512 | 0.000 | 0.512 |
| 30.00% | 28000 | 2.98 | 1.82 | 11.4 | 90.1 | 0 | 0.451 | 0.500 | 0.049 | 0.549 |
| 40.00% | 34000 | 2.98 | 0.52 | 95.5 | 25.7 | 0 | 0.037 | 0.598 | 0.366 | 0.963 |
| 50.00% | 40000 | 2.99 | 0.06 | | 3.0 | NA | 0 | 0.524 | 0.476 | 1.000 |
| 60.00% | 46000 | 2.99 | 0.03 | | 1.5 | NA | 0 | 0.517 | 0.483 | 1.000 |
| 70.00% | 52000 | 2.97 | 0.03 | | 1.5 | NA | 0 | 0.512 | 0.488 | 1.000 |
| 80.00% | 58000 | 2.98 | 0.02 | | 1.0 | NA | 0 | 0.512 | 0.488 | 1.000 |
| 90.00% | 64000 | 2.99 | 0.01 | | 0.5 | NA | 0 | 0.512 | 0.488 | 1.000 |

TABLE 6

Figure 6:
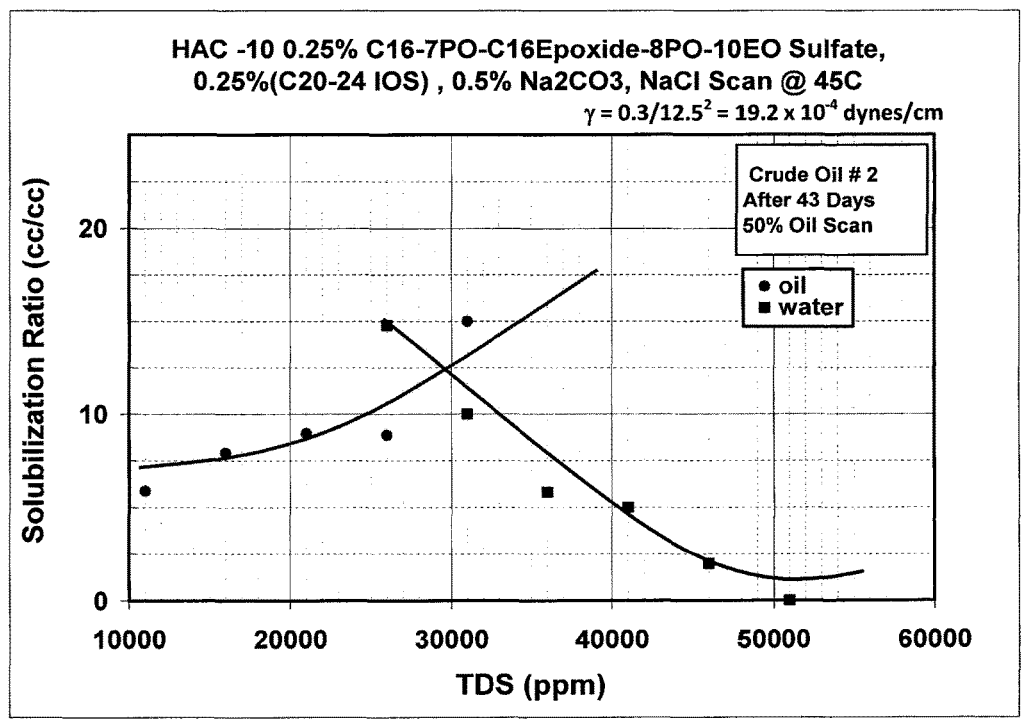
FIG. 6. Phase behavior plot for a study with HAC-10 0.25% C16-7PO alkoxylate/C16 Epoxide-8PO-10EO Sulfate, 0.25% (C20-24 IOS), 0.5% $Na_2CO_3$, NaCl Scan at 45° C.

Phase behavior data recording sheet for the study described in FIG. 6.

| | | | | |
|---|---|---|---|---|
| Experiment | HAC-10 0.25% C16-7PO-C16 Epoxide-8PO-10EO SO4, 0.25% C20-24 IOS, 0.5% Na2CO3, NaCl Scan in Brine # 2 with Oil # 2 (50% | | | |
| Hydrocarbon | Crude Oil # 2 | Hydrocarbon Density | g/cc | Typical hydrocarbon Densities: |
| Surfactant | C16-7PO-C16 Epoxide-8PO-10EO SO4 | Total Surfactant Conc. | 0.5 wt % | Octane |
| | | Total Co-solvent Conc. | 0 wt % | Decane |
| Co-Surfactant(1) | C20-24 IOS | Polymer Conc. | 0 wt % | Mixed: Dec. 1, 2010 Extended scan |
| Co-Solvent | | Na2CO3 Conc. | 0 wt % | |
| Surfactant Conc. | 0.25 wt % | WOR | 1 | |
| Co-surf(1) Conc. | 0.25 wt % | Temperature | 45 Celcius | |
| t-pent Conc. | wt % | Tube Size | 5 mL | |
| Butanol 2.15 EO | wt % | | | |
| NaCl:CaCl Ratio | | | | |

| Salinity (wt % NaC;) | TDS (ppm) | Aqueous Level | Hydrocarbon Level | Top of emulsion | Top Interface | Bottom Interface | Bottom of emulsion | Type | Volume of Oil Solublized (cc) | Volume of Water Solublized (cc) |
|---|---|---|---|---|---|---|---|---|---|---|
| | | Jan. 13, 2011 | | | | | 43 days | | | |
| 0.00% | 6000 | 2.95 | | | 2.90 | | | I | 0.05 | |
| 0.50% | 11000 | 2.96 | | | 2.90 | | | I | 0.06 | |
| 1.00% | 16000 | 2.98 | | | 2.90 | | | I | 0.08 | |
| 1.50% | 21000 | 2.99 | | | 2.90 | | | I | 0.09 | |
| 2.00% | 26000 | 2.97 | | | 2.88 | 3.12 | | III | 0.09 | 0.15 |
| 2.50% | 31000 | 3.00 | | | 2.85 | 3.10 | | III | 0.15 | 0.10 |
| 3.00% | 36000 | 2.94 | | | | 3.00 | | II | 2.94 | 0.06 |
| 3.50% | 41000 | 3.00 | | | | 3.05 | | II | 3.00 | 0.05 |
| 4.00% | 46000 | 2.98 | | | | 3.00 | | II | 2.98 | 0.02 |
| 4.50% | 51000 | 3.00 | | | | 3.00 | | II | 3.00 | 0.00 |
| | | Dec. 13, 2010 | | | | | 12 days | | | |
| 0.00% | 6000 | 2.95 | | | 2.90 | | | I | 0.05 | |
| 0.50% | 11000 | 2.96 | | | 2.90 | | | I | 0.06 | |
| 1.00% | 16000 | 2.98 | | | 2.90 | | | I | 0.08 | |
| 1.50% | 21000 | 2.99 | | | 2.90 | | | I | 0.09 | |
| 2.00% | 26000 | 2.97 | | | 2.88 | 3.10 | | III | 0.09 | 0.13 |
| 2.50% | 31000 | 3.00 | | | 2.80 | 3.10 | | III | 0.20 | 0.10 |
| 3.00% | 36000 | 2.94 | | | | 3.00 | | II | 2.94 | 0.06 |
| 3.50% | 41000 | 3.00 | | | | 3.05 | | II | 3.00 | 0.05 |
| 4.00% | 46000 | 2.98 | | | | 3.00 | | II | 2.98 | 0.02 |
| 4.50% | 51000 | 3.00 | | | | 3.00 | | II | 3.00 | 0.00 |

| Salinity (wt % NaC;) | TDS (ppm) | Aqueous Level | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volume Fraction of Water ($V_w$) | $V_w + V_{me}$ |
|---|---|---|---|---|---|---|---|---|---|
| | | Jan. 13, 2011 | | | | 43 days | | | |
| 0.00% | 6000 | 2.95 | 4.9 | | 0 | 0.580 | 0.420 | 0.000 | 0.420 |
| 0.50% | 11000 | 2.96 | 5.9 | | 0 | 0.580 | 0.420 | 0.000 | 0.420 |
| 1.00% | 16000 | 2.98 | 7.9 | | 0 | 0.580 | 0.420 | 0.000 | 0.420 |
| 1.50% | 21000 | 2.99 | 9.0 | | 0 | 0.580 | 0.420 | 0.000 | 0.420 |
| 2.00% | 26000 | 2.97 | 8.9 | 14.8 | 0 | 0.576 | 0.048 | 0.376 | 0.424 |
| 2.50% | 31000 | 3.00 | 15.0 | 10.0 | 0 | 0.570 | 0.050 | 0.380 | 0.430 |
| 3.00% | 36000 | 2.94 | | 5.8 | NA | 0 | 0.600 | 0.400 | 1.000 |
| 3.50% | 41000 | 3.00 | | 5.0 | NA | 0 | 0.610 | 0.390 | 1.000 |
| 4.00% | 46000 | 2.98 | | 2.0 | NA | 0 | 0.600 | 0.400 | 1.000 |
| 4.50% | 51000 | 3.00 | | 0.0 | NA | 0 | 0.600 | 0.400 | 1.000 |
| | | Dec. 13, 2010 | | | | 12 days | | | |
| 0.00% | 6000 | 2.95 | 4.9 | | 0 | 0.580 | 0.420 | 0.000 | 0.420 |
| 0.50% | 11000 | 2.96 | 5.9 | | 0 | 0.580 | 0.420 | 0.000 | 0.420 |

TABLE 6-continued

Phase behavior data recording sheet for the study described in FIG. 6.

|        |       |      |      |      |    |       |       |       |       |
|--------|-------|------|------|------|----|-------|-------|-------|-------|
| 1.00%  | 16000 | 2.98 | 7.9  |      | 0  | 0.580 | 0.420 | 0.000 | 0.420 |
| 1.50%  | 21000 | 2.99 | 9.0  |      | 0  | 0.580 | 0.420 | 0.000 | 0.420 |
| 2.00%  | 26000 | 2.97 | 8.9  | 12.8 | 0  | 0.576 | 0.044 | 0.380 | 0.424 |
| 2.50%  | 31000 | 3.00 | 20.0 | 10.0 | 0  | 0.560 | 0.060 | 0.380 | 0.440 |
| 3.00%  | 36000 | 2.94 |      | 5.8  | NA | 0     | 0.600 | 0.400 | 1.000 |
| 3.50%  | 41000 | 3.00 |      | 5.0  | NA | 0     | 0.610 | 0.390 | 1.000 |
| 4.00%  | 46000 | 2.98 |      | 2.0  | NA | 0     | 0.600 | 0.400 | 1.000 |
| 4.50%  | 51000 | 3.00 |      | 0.0  | NA | 0     | 0.600 | 0.400 | 1.000 |

TABLE 7

Figure 7:
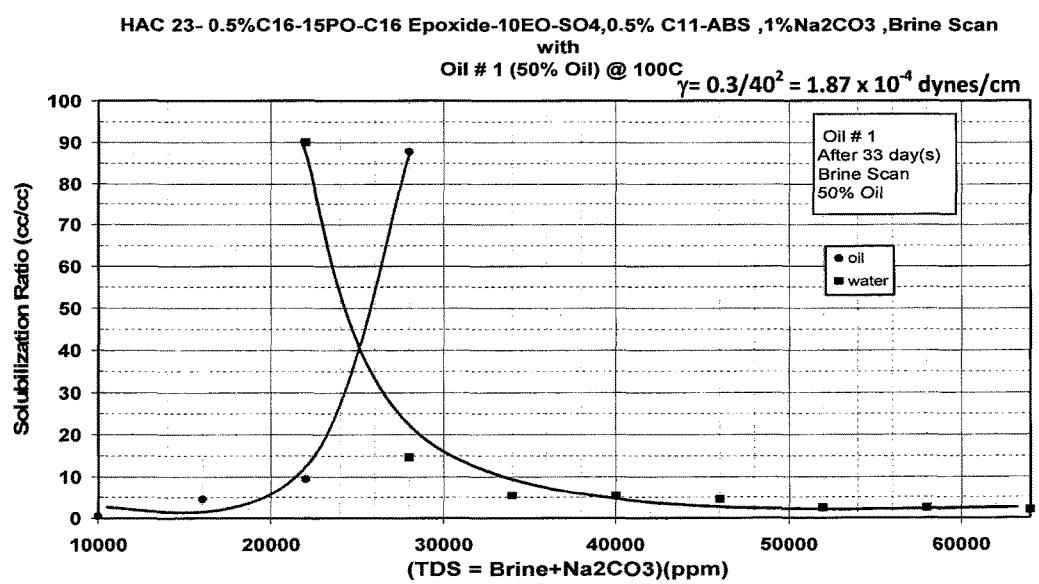
FIG. 7. Phase behavior plot for a study with HAC-23 0.5% C16-15PO alkoxylate/C16 Epoxide-10EO-SO4, 0.5% C11-ABS, 1% $Na_2CO_3$, Brine Scan with Oil #1 (50% Oil) at 100° C.

Phase behavior data recording sheet for the study described in FIG. 7.

| | | | | |
|---|---|---|---|---|
| Experiment | HAC 23-0.5% C16-15PO-C16 Epoxide-10EO-SO4, 0.5% C11-ABS, 1 Scan with Oil # 1 (50% Oil) @ 100 C. | | | |
| Hydrocarbon | Oil # 1 | Hydrocarbon Density | 1 | g/cc | Typical |
| Surfactant | C16-15PO-C16Epoxide-10EO-SO4 | Total Surfactant Conc. | 1 | wt % | Octane |
| Co-Surfactant(1) | C11-ABS | Total Alcohol Conc. | 0 | wt % | Decane |
| Co-Solvent | | Polymer Conc. | 0 | wt % | Mixed: |
| Surfactant Conc. | 0.5 | Na2CO3 Conc. | 0 | wt % | |
| Co-surf(1) Conc. | 0.5 | wt % | WOR | 1 | |
| t-pent Conc. | | wt % | Temperature | 100 | Celcius |
| alkali | varied | wt % | Tube Size | 5 | mL |
| NaCl:CaCl Ratio | | | | | |

| Salinity (% of Brine) | TDS in ppm (from Brine + Na2CO3) | Aqueous Level | Hydro-carbon Level | Top of emulsion | Top Interface | Bottom Inter face | Bottom of emulsion | Type | Volume of Oil Solublized (cc) | Volume of Water Solublized (cc) | Oil Sol. Ratio (cc/cc) | Water Sol. Ratio (cc/cc) | HC Sol. (mg/L) |
|---|---|---|---|---|---|---|---|---|---|---|---|---|---|
| | Mar. 23, 2011 | | | | | | | 33 days | | | | | |
| 0.00%  | 10000 | 2.91 | 0.9 | 2.90 |      |      | I   | 0.01 |      | 0.5  |      | 0  |
| 10.00% | 16000 | 2.99 | 0.9 | 2.90 |      |      | I   | 0.09 |      | 4.5  |      | 0  |
| 20.00% | 22000 | 2.99 | 0.9 | 2.78 | 4.80 |      | III | 0.21 | 1.81 | 10.4 | 90.0 | 0  |
| 30.00% | 28000 | 2.95 | 0.9 | 1.15 | 3.28 |      | III | 1.80 | 0.33 | 87.8 | 16.1 | 0  |
| 40.00% | 34000 | 2.99 | 0.9 |      | 3.10 |      | II  | 2.99 | 0.11 |      | 5.5  | NA |
| 50.00% | 40000 | 2.99 | 0.9 |      | 3.10 |      | II  | 2.99 | 0.11 |      | 5.5  | NA |
| 60.00% | 46000 | 2.99 | 0.9 |      | 3.08 |      | II  | 2.99 | 0.09 |      | 4.5  | NA |
| 70.00% | 52000 | 2.95 | 0.9 |      | 3.00 |      | II  | 2.95 | 0.05 |      | 2.4  | NA |
| 80.00% | 58000 | 2.95 | 0.9 |      | 3.00 |      | II  | 2.95 | 0.05 |      | 2.4  | NA |
| 90.00% | 64000 | 2.91 | 0.9 |      | 2.95 |      | II  | 2.91 | 0.04 |      | 1.9  | NA |
| | Mar. 3, 2011 | | | | | | | 13 days | | | | | |
| 0.00%  | 10000 | 2.91 | 0.9 | 2.88 |      |      | I   | 0.03 |      | 1.4  |      | 0  |
| 10.00% | 16000 | 2.99 | 0.9 | 2.90 |      |      | I   | 0.09 |      | 4.5  |      | 0  |
| 20.00% | 22000 | 2.99 | 0.9 | 2.78 | 4.80 |      | III | 0.21 | 1.81 | 10.4 | 90.0 | 0  |
| 30.00% | 28000 | 2.95 | 0.9 | 1.00 | 3.50 |      | III | 1.95 | 0.55 | 95.1 | 26.8 | 0  |
| 40.00% | 34000 | 2.99 | 0.9 |      | 3.15 |      | II  | 2.99 | 0.16 |      | 8.0  | NA |
| 50.00% | 40000 | 2.99 | 0.9 |      | 3.05 |      | II  | 2.99 | 0.06 |      | 3.0  | NA |
| 60.00% | 46000 | 2.99 | 0.9 |      | 3.05 |      | II  | 2.99 | 0.06 |      | 3.0  | NA |
| 70.00% | 52000 | 2.95 | 0.9 |      | 3.00 |      | II  | 2.95 | 0.05 |      | 2.4  | NA |
| 80.00% | 58000 | 2.95 | 0.9 |      | 3.00 |      | II  | 2.95 | 0.05 |      | 2.4  | NA |
| 90.00% | 64000 | 2.91 | 0.9 |      | 2.95 |      | II  | 2.91 | 0.04 |      | 1.9  | NA |

TABLE 8

Figure 8:
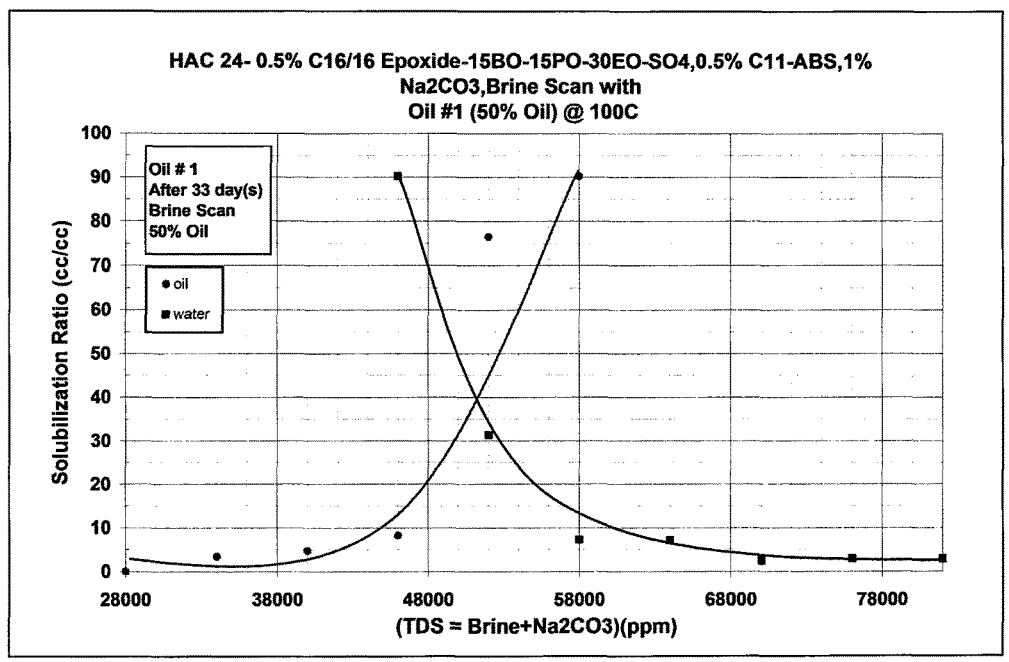
FIG. 8. Phase behavior plot for a study with HAC-24 0.5% C16 alcohol/C16 Epoxide-15BO-15PO-30EO-SO4, 0.5% C11-ABS, 1% Na2CO3, Brine Scan with Oil #1 (50% Oil) at 100° C.

Phase behavior data recording sheet for the study described in FIG. 8.

| | | | | |
|---|---|---|---|---|
| Experiment | HAC 24-0.5% C16/16 Epoxide-15BO-15PO-30EO-SO4, 0.5% C11-ABS, 1% Na2CO3, Brine Scan with Oil #1 (50% Oil) @ 100 C. | | | |
| Hydrocarbon | Oil # 1 | Hydrocarbon Density | g/cc | Typical hydrocarbon Densities: |
| Surfactant | C16/16 Epoxide-15BO-15PO-30EO-SO4 | Total Surfactant Conc. | 1 wt % | Octane |
| Co-Surfactant(1) | C11-ABS | Total Alcohol Conc. | 0 wt % | Decane |
| Co-Solvent | | Polymer Conc. | 0 wt % | Mixed: Feb. 18, 2011 |
| Surfactant Conc. | 0.5 | Na2CO3 Conc. | 0 wt % | |
| Co-surf(1) Conc. | 0.5 wt % | WOR | 1 | |
| t-pent Conc. | wt % | Temperature | 100 Celcius | |

TABLE 8-continued

Phase behavior data recording sheet for the study described in FIG. 8.

| alkali | varied | wt % | Tube Size | | 5 | mL |
|---|---|---|---|---|---|---|
| NaCl:CaCl Ratio | | | | | | |

| Salinity (% of SUTIB) | TDS in ppm (from SSUTIB) | Aqueous Level | Hydrocarbon Level | Top of emulsion | Top Interface | Bottom Interface | Bottom of emulsion | Type | Volume of Oil Solublized (cc) | Volume of Water Solublized (cc) |
|---|---|---|---|---|---|---|---|---|---|---|
| | | Mar. 23, 2011 | | | | | 33 days | | | |
| 30.00% | 28000 | 2.90 | 0.9 | | 2.90 | | | I | 0.00 | |
| 40.00% | 34000 | 2.95 | 0.9 | | 2.88 | | | I | 0.07 | |
| 50.00% | 40000 | 2.90 | 0.9 | | 2.80 | | | I | 0.10 | |
| 60.00% | 46000 | 2.95 | 0.9 | | 2.78 | 4.80 | | III | 0.17 | 1.85 |
| 70.00% | 52000 | 2.96 | 0.9 | | 1.40 | 3.60 | | III | 1.56 | 0.64 |
| 80.00% | 58000 | 2.95 | 0.9 | | 1.10 | 3.10 | | III | 1.85 | 0.15 |
| 90.00% | 64000 | 2.90 | 0.9 | | | 3.05 | | II | 2.90 | 0.15 |
| 100.00% | 70000 | 2.97 | 0.9 | | | 3.02 | | II | 2.97 | 0.05 |
| 110.00% | 76000 | 2.96 | 0.9 | | | 3.02 | | II | 2.96 | 0.06 |
| 120.00% | 82000 | 2.94 | 0.9 | | | 3.00 | | II | 2.94 | 0.06 |
| | | Mar. 3, 2011 | | | | | 13 days | | | |
| 30.00% | 28000 | 2.90 | 0.9 | | 2.90 | | | I | 0.00 | |
| 40.00% | 34000 | 2.95 | 0.9 | | 2.88 | | | I | 0.07 | |
| 50.00% | 40000 | 2.90 | 0.9 | | 2.80 | | | I | 0.10 | |
| 60.00% | 46000 | 2.95 | 0.9 | | 2.80 | 4.80 | | III | 0.15 | 1.85 |
| 70.00% | 52000 | 2.96 | 0.9 | | 1.10 | 3.90 | | III | 1.86 | 0.94 |
| 80.00% | 58000 | 2.95 | 0.9 | | 1.00 | 3.10 | | III | 1.95 | 0.15 |
| 90.00% | 64000 | 2.90 | 0.9 | | | 3.05 | | II | 2.90 | 0.15 |
| 100.00% | 70000 | 2.97 | 0.9 | | | 3.02 | | II | 2.97 | 0.05 |
| 110.00% | 76000 | 2.96 | 0.9 | | | 3.02 | | II | 2.96 | 0.06 |
| 120.00% | 82000 | 2.94 | 0.9 | | | 3.00 | | II | 2.94 | 0.06 |

| Salinity (% of SUTIB) | TDS in ppm (from SSUTIB) | Aqueous Level | Oil Sol. Ratio (cc/cc) | Water Sol. Ratio (cc/cc) | HC Sol. (mg/L) | Volume Fraction of Oil (Vo) | Volume Fraction of Microemulsion (Vme) | Volumn Fraction of Water (Vw) | Vw + Vme |
|---|---|---|---|---|---|---|---|---|---|
| | | Mar. 23, 2011 | | | | 33 days | | | |
| 30.00% | 28000 | 2.90 | 0.0 | | 0 | 0.488 | 0.512 | 0.000 | 0.512 |
| 40.00% | 34000 | 2.95 | 3.4 | | 0 | 0.483 | 0.517 | 0.000 | 0.517 |
| 50.00% | 40000 | 2.90 | 4.8 | | 0 | 0.463 | 0.537 | 0.000 | 0.537 |
| 60.00% | 46000 | 2.95 | 8.3 | 90.2 | 0 | 0.459 | 0.493 | 0.049 | 0.541 |
| 70.00% | 52000 | 2.96 | 76.5 | 31.4 | 0 | 0.122 | 0.537 | 0.341 | 0.878 |
| 80.00% | 58000 | 2.95 | 90.2 | 7.3 | 0 | 0.049 | 0.488 | 0.463 | 0.951 |
| 90.00% | 64000 | 2.90 | | 7.1 | NA | 0 | 0.524 | 0.476 | 1.000 |
| 100.00% | 70000 | 2.97 | | 2.5 | NA | 0 | 0.517 | 0.483 | 1.000 |
| 110.00% | 76000 | 2.96 | | 2.9 | NA | 0 | 0.517 | 0.483 | 1.000 |
| 120.00% | 82000 | 2.94 | | 2.9 | NA | 0 | 0.512 | 0.488 | 1.000 |
| | | Mar. 3, 2011 | | | | 13 days | | | |
| 30.00% | 28000 | 2.90 | 0.0 | | 0 | 0.488 | 0.512 | 0.000 | 0.512 |
| 40.00% | 34000 | 2.95 | 3.4 | | 0 | 0.483 | 0.517 | 0.000 | 0.517 |
| 50.00% | 40000 | 2.90 | 4.8 | | 0 | 0.463 | 0.537 | 0.000 | 0.537 |
| 60.00% | 46000 | 2.95 | 7.3 | 90.2 | 0 | 0.463 | 0.488 | 0.049 | 0.537 |
| 70.00% | 52000 | 2.96 | 91.2 | 46.1 | 0 | 0.049 | 0.683 | 0.268 | 0.951 |
| 80.00% | 58000 | 2.95 | 95.1 | 7.3 | 0 | 0.024 | 0.512 | 0.463 | 0.976 |
| 90.00% | 64000 | 2.90 | | 7.1 | NA | 0 | 0.524 | 0.476 | 1.000 |
| 100.00% | 70000 | 2.97 | | 2.5 | NA | 0 | 0.517 | 0.483 | 1.000 |
| 110.00% | 76000 | 2.96 | | 2.9 | NA | 0 | 0.517 | 0.483 | 1.000 |
| 120.00% | 82000 | 2.94 | | 2.9 | NA | 0 | 0.512 | 0.488 | 1.000 |

TABLE 9

Figure 9:
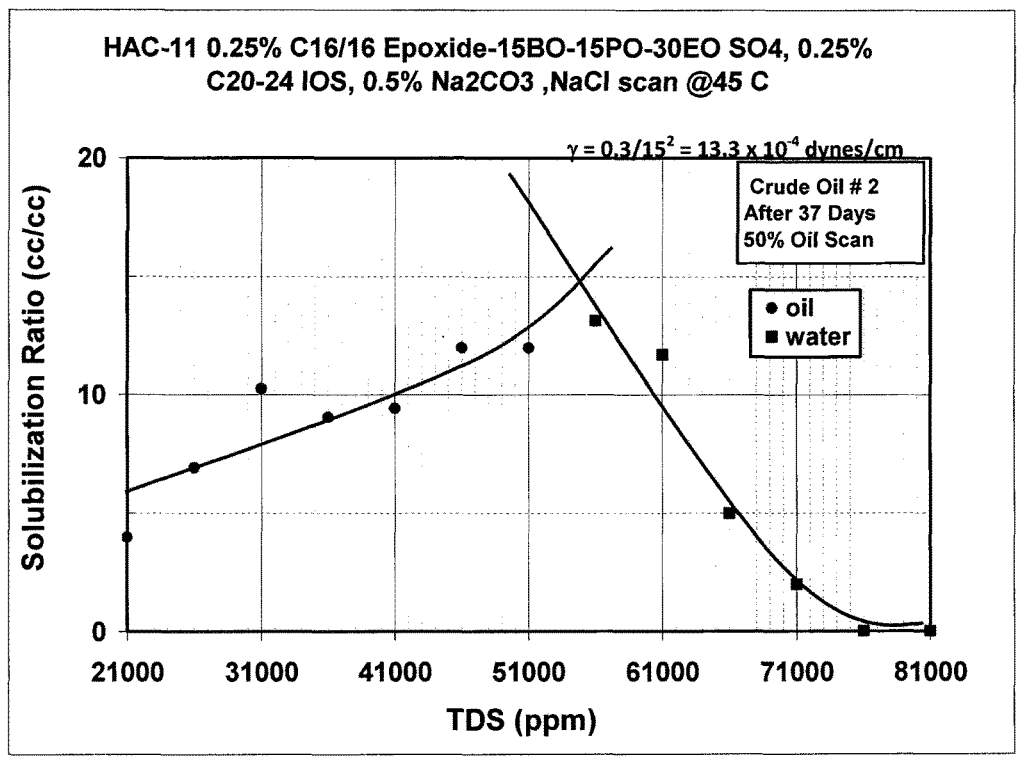
FIG. 9. Phase behavior plot for a study with HAC-11 0.25% C16 alcohol/C16 Epoxide-15BO-15PO-30EO SO4, 0.25% C20-24 IOS, 0.5% $Na_2CO_3$, NaCl scan at 45° C.

Phase behavior data recording sheet for the study described in FIG. 9.

| Experiment | HAC-11 0.25% C16/16 epoxide-15BO-30EO SO4, 0.25% C20-24 IOS, 0.5% Na2CO3, NaCl scan in Brine # 2 With oil # 2 (50% oil) | | | | |
|---|---|---|---|---|---|
| Hydrocarbon | Crude Oil # 2 | | Hydrocarbon Density | | g/cc | Typical hydrocarbon Densities: |
| Surfactant | C16/16 epoxide-15BO-30EO SO4 | | Total Surfactant Conc. | 0.5 | wt % | Octane |
| Co-Surfactant(1) | C20-24 IOS | | Total Co-solvent Conc. | 0 | wt % | Decane |
| Co-Solvent | | | Polymer Conc. | 0 | wt % | Mixed: Dec. 7, 2010 |
| Surfactant Conc. | 0.25 | wt % | Na2CO3 Conc. | 0 | wt % | |
| Co-surf(1) Conc. | 0.25 | wt % | WOR | 1 | | |
| t-pent Conc. | | wt % | Temperature | 45 | Celcius | |

TABLE 9-continued

Phase behavior data recording sheet for the study described in FIG. 9.

Butanol 2.15 EO  wt %  Tube Size  5  mL
NaCl:CaCl Ratio

| Salinity (wt % NaC;) | TDS (ppm) | Aqueous Level | Hydro-carbon Level | Top of emulsion | Top Interface | Bottom Interface | Bottom of emulsion | Type | Volume of Oil Solublized (cc) | Volume of Water Solublized (cc) |
|---|---|---|---|---|---|---|---|---|---|---|
| | | Jan. 13, 2011 | | | | | 37 days | | | |
| 1.50% | 21000 | 2.99 | | | 2.95 | | | I | 0.04 | |
| 2.00% | 26000 | 2.97 | | | 2.90 | | | I | 0.07 | |
| 2.50% | 31000 | 3.05 | | | 2.95 | | | I | 0.10 | |
| 3.00% | 36000 | 3.01 | | | 2.92 | | | I | 0.09 | |
| 3.50% | 41000 | 3.09 | | | 3.00 | | | I | 0.09 | |
| 4.00% | 46000 | 3.00 | | | 2.88 | | | I | 0.12 | |
| 4.50% | 51000 | 3.00 | | | 2.88 | | | I | 0.12 | |
| 5.00% | 56000 | 3.02 | | | | 3.15 | | II | 3.02 | 0.13 |
| 5.50% | 61000 | 2.95 | | | | 3.07 | | II | 2.95 | 0.12 |
| 6.00% | 66000 | 3.00 | | | | 3.05 | | II | 3.00 | 0.05 |
| 6.50% | 71000 | 3.00 | | | | 3.02 | | II | 3.00 | 0.02 |
| 7.00% | 76000 | 3.00 | | | | 3.00 | | II | 3.00 | 0.00 |
| 7.50% | 81000 | 3.00 | | | | 3.00 | | II | 3.00 | 0.00 |
| | | Dec. 16, 2010 | | | | | 9 days | | | |
| 1.50% | 21000 | 2.99 | | | 2.95 | | | I | 0.04 | |
| 2.00% | 26000 | 2.97 | | | 2.90 | | | I | 0.07 | |
| 2.50% | 31000 | 3.05 | | | 2.98 | | | I | 0.07 | |
| 3.00% | 36000 | 3.01 | | | 2.95 | | | I | 0.06 | |
| 3.50% | 41000 | 3.09 | | | 3.00 | | | I | 0.09 | |
| 4.00% | 46000 | 3.00 | | | 2.85 | | | I | 0.15 | |
| 4.50% | 51000 | 3.00 | | | 2.85 | | | I | 0.15 | |
| 5.00% | 56000 | 3.02 | | | | 3.25 | | II | 3.02 | 0.23 |
| 5.50% | 61000 | 2.95 | | | | 3.10 | | II | 2.95 | 0.15 |
| 6.00% | 66000 | 3.00 | | | | 3.10 | | II | 3.00 | 0.10 |
| 6.50% | 71000 | 3.00 | | | | 3.05 | | II | 3.00 | 0.05 |
| 7.00% | 76000 | 3.00 | | | | 3.00 | | II | 3.00 | 0.00 |
| 7.50% | 81000 | 3.00 | | | | 3.00 | | II | 3.00 | 0.00 |

| Salinity (wt % NaC;) | TDS (ppm) | Aqueous Level | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ |
|---|---|---|---|---|---|---|---|---|---|
| | | Jan. 13, 2011 | | | | | 37 days | | |
| 1.50% | 21000 | 2.99 | 4.0 | | 0 | 0.590 | 0.410 | 0.000 | 0.410 |
| 2.00% | 26000 | 2.97 | 6.9 | | 0 | 0.580 | 0.420 | 0.000 | 0.420 |
| 2.50% | 31000 | 3.05 | 10.3 | | 0 | 0.590 | 0.410 | 0.000 | 0.410 |
| 3.00% | 36000 | 3.01 | 9.0 | | 0 | 0.584 | 0.416 | 0.000 | 0.416 |
| 3.50% | 41000 | 3.09 | 9.4 | | 0 | 0.600 | 0.400 | 0.000 | 0.400 |
| 4.00% | 46000 | 3.00 | 12.0 | | 0 | 0.576 | 0.424 | 0.000 | 0.424 |
| 4.50% | 51000 | 3.00 | 12.0 | | 0 | 0.576 | 0.424 | 0.000 | 0.424 |
| 5.00% | 56000 | 3.02 | | 13.1 | NA | 0 | 0.630 | 0.370 | 1.000 |
| 5.50% | 61000 | 2.95 | | 11.7 | NA | 0 | 0.614 | 0.386 | 1.000 |
| 6.00% | 66000 | 3.00 | | 5.0 | NA | 0 | 0.610 | 0.390 | 1.000 |
| 6.50% | 71000 | 3.00 | | 2.0 | NA | 0 | 0.604 | 0.396 | 1.000 |
| 7.00% | 76000 | 3.00 | | 0.0 | NA | 0 | 0.600 | 0.400 | 1.000 |
| 7.50% | 81000 | 3.00 | | 0.0 | NA | 0 | 0.600 | 0.400 | 1.000 |
| | | Dec. 16, 2010 | | | | | 9 days | | |
| 1.50% | 21000 | 2.99 | 4.0 | | 0 | 0.590 | 0.410 | 0.000 | 0.410 |
| 2.00% | 26000 | 2.97 | 6.9 | | 0 | 0.580 | 0.420 | 0.000 | 0.420 |
| 2.50% | 31000 | 3.05 | 7.2 | | 0 | 0.596 | 0.404 | 0.000 | 0.404 |
| 3.00% | 36000 | 3.01 | 6.0 | | 0 | 0.590 | 0.410 | 0.000 | 0.410 |
| 3.50% | 41000 | 3.09 | 9.4 | | 0 | 0.600 | 0.400 | 0.000 | 0.400 |
| 4.00% | 46000 | 3.00 | 15.0 | | 0 | 0.570 | 0.430 | 0.000 | 0.430 |
| 4.50% | 51000 | 3.00 | 15.0 | | 0 | 0.570 | 0.430 | 0.000 | 0.430 |
| 5.00% | 56000 | 3.02 | | 23.2 | NA | 0 | 0.650 | 0.350 | 1.000 |
| 5.50% | 61000 | 2.95 | | 14.6 | NA | 0 | 0.620 | 0.380 | 1.000 |
| 6.00% | 66000 | 3.00 | | 10.0 | NA | 0 | 0.620 | 0.380 | 1.000 |
| 6.50% | 71000 | 3.00 | | 5.0 | NA | 0 | 0.610 | 0.390 | 1.000 |
| 7.00% | 76000 | 3.00 | | 0.0 | NA | 0 | 0.600 | 0.400 | 1.000 |
| 7.50% | 81000 | 3.00 | | 0.0 | NA | 0 | 0.600 | 0.400 | 1.000 |

TABLE 10

Figure 10:
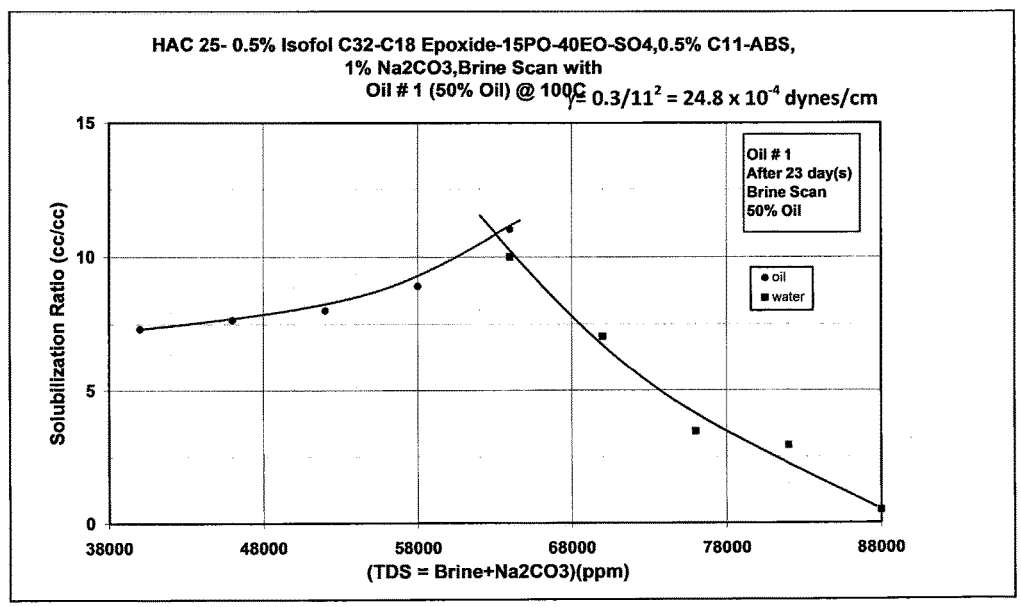
FIG. 10. Phase behavior plot for a study with HAC-25 0.5% Isofol C32 alcohol-C18 Epoxide-15PO-40EO-SO4, 0.5% C11-ABS, 1% Na2CO3, Brine Scan with Oil #1 (50% Oil) at 100° C.

Phase behavior data recording sheet for the study described in FIG. 10.

| Experiment | | HAC 25 0.5% Isofol C32-C18 Epoxide-15PO-40EO-SO4, 0.5% C11-ABS, 1% Na2CO3, Brine Scan with Oil # 1 (50% Oil scan) | | |
|---|---|---|---|---|
| Hydrocarbon | Oil # 1 | Hydrocarbon Density | 1 | g/cc |
| Surfactant | Isofol C32-C18 Epoxide-15PO-40EO-SO4 | Total Surfactant Conc. | 0 | wt % |
| Co-Surfactant(1) | C11-ABS | Total Alcohol Conc. | 0 | wt % |
| Co-Solvent | | Polymer Conc. | 0 | wt % |
| Surfactant Conc. | 0.5 wt % | Na2CO3 Conc. | 1 | wt % |
| Co-surf(1) Conc. | 0.5 wt % | WOR | 1 | |
| t-pent Conc. | wt % | Temperature | 100 | Celcius |
| alkali | varied | Tube Size | 5 | mL |
| NaCl:CaCl Ratio | | | | |

Typical hydrocarbon Densities: Octane, Decane
Mixed: Feb. 28, 2011

| Salinity (% of SUTIB) | TDS in ppm (from SSUTIB) | Aqueous Level | Hydro-carbon Level | Top of emulsion | Top Interface | Bottom Interface | Bottom of emulsion | Type | Volume of Oil Solubilized (cc) | Volume of Water Solubilized (cc) | Oil Sol. Ratio (cc/cc) | Water Sol. Ratio (cc/cc) | HC Sol. (mg/L) | Volume Fraction of Oil (Vo) | Volume Fraction of Microemulsion (Vme) | Volumn Fraction of Water (Vw) | Vw + Vme |
|---|---|---|---|---|---|---|---|---|---|---|---|---|---|---|---|---|---|
| | | Mar. 23, 2011 | | | | | | | | | | | | | | | |
| 50.00% | 40000 | 2.95 | 0.9 | | 2.80 | | | I | 0.15 | | 7.3 | | 0 | 0.463 | 0.537 | 0.000 | 0.537 |
| 60.00% | 46000 | 3.04 | 0.9 | | 2.89 | | | I | 0.15 | | 7.7 | | 0 | 0.485 | 0.515 | 0.000 | 0.515 |
| 70.00% | 52000 | 3.00 | 0.9 | | 2.84 | | | I | 0.16 | | 8.0 | | 0 | 0.473 | 0.527 | 0.000 | 0.527 |
| 80.00% | 58000 | 2.98 | 0.9 | | 2.80 | | | I | 0.18 | | 8.9 | | 0 | 0.463 | 0.537 | 0.000 | 0.537 |
| 90.00% | 64000 | 3.00 | 0.9 | | 2.78 | 3.20 | | III | 0.22 | 0.20 | 11.0 | 10.0 | 0 | 0.459 | 0.102 | 0.439 | 0.541 |
| 100.00% | 70000 | 3.01 | 0.9 | | | 3.15 | | II | 3.01 | 0.14 | | 7.0 | NA | 0 | 0.549 | 0.451 | 1.000 |
| 110.00% | 76000 | 2.98 | 0.9 | | | 3.05 | | II | 2.98 | 0.07 | | 3.5 | NA | 0 | 0.524 | 0.476 | 1.000 |
| 120.00% | 82000 | 2.96 | 0.9 | | | 3.02 | | II | 2.96 | 0.06 | | 2.9 | NA | 0 | 0.517 | 0.483 | 1.000 |
| 130.00% | 88000 | 2.94 | 0.9 | | | 2.95 | | II | 2.94 | 0.01 | | 0.5 | NA | 0 | 0.500 | 0.500 | 1.000 |
| | | Mar. 7, 2011 | | | | | | | | | | | | | | | |
| 50.00% | 40000 | 2.98 | 0.9 | | 2.85 | | | I | 0.13 | | 6.4 | | 0 | 0.476 | 0.524 | 0.000 | 0.524 |
| 60.00% | 46000 | 3.02 | 0.9 | | 2.95 | | | I | 0.07 | | 3.5 | | 0 | 0.500 | 0.500 | 0.000 | 0.500 |
| 70.00% | 52000 | 3.00 | 0.9 | | 2.90 | | | I | 0.10 | | 5.0 | | 0 | 0.488 | 0.512 | 0.000 | 0.512 |
| 80.00% | 58000 | 2.98 | 0.9 | | 2.85 | | | I | 0.13 | | 6.4 | | 0 | 0.476 | 0.524 | 0.000 | 0.524 |
| 90.00% | 64000 | 3.00 | 0.9 | | 2.90 | 3.25 | | III | 0.10 | 0.25 | 5.0 | 12.5 | 0 | 0.488 | 0.085 | 0.427 | 0.512 |
| 100.00% | 70000 | 3.01 | 0.9 | | | 3.15 | | II | 3.01 | 0.14 | | 7.0 | NA | 0 | 0.549 | 0.451 | 1.000 |
| 110.00% | 76000 | 2.98 | 0.9 | | | 3.10 | | II | 2.98 | 0.12 | | 5.9 | NA | 0 | 0.537 | 0.463 | 1.000 |
| 120.00% | 82000 | 2.96 | 0.9 | | | 3.10 | | II | 2.96 | 0.14 | | 6.9 | NA | 0 | 0.537 | 0.463 | 1.000 |
| 130.00% | 88000 | 2.94 | 0.9 | | | 3.10 | | II | 2.94 | 0.16 | | 7.8 | NA | 0 | 0.537 | 0.463 | 1.000 |

TABLE 11

Figure 11:
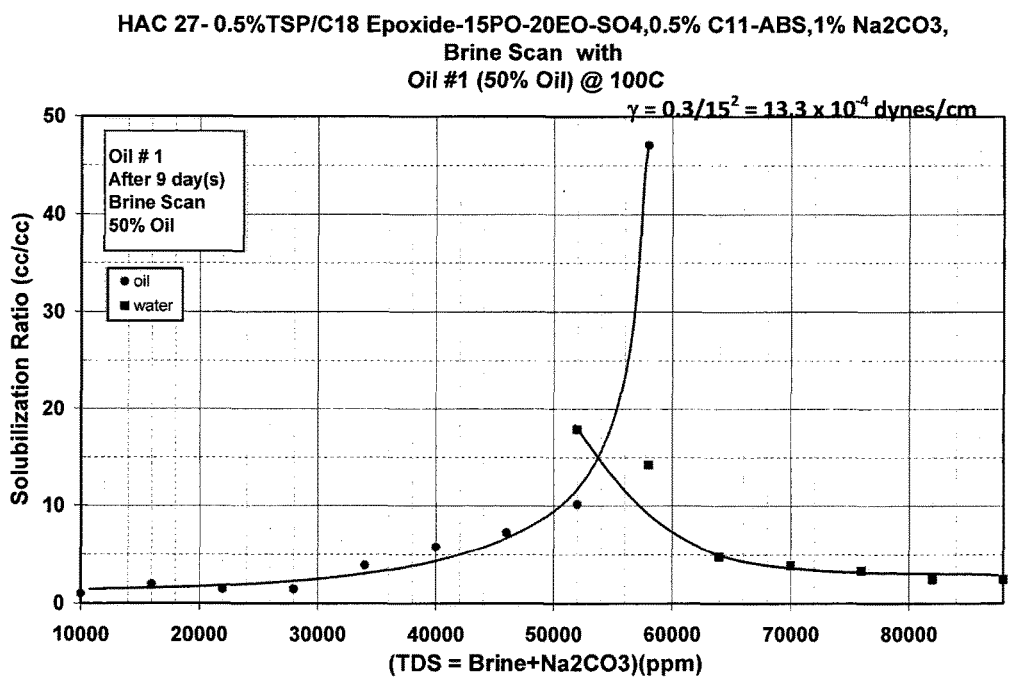
FIG. 11. Phase behavior plot for a study with HAC-27 0.5% TSP/C18 Epoxide-15PO-20EO-SO4, 0.5% C11-ABS, 1% $Na_2CO_3$, Brine Scan with Oil #1 (50% Oil) at 100° C.

Phase behavior data recording sheet for the study described in FIG. 11.

| Experiment | | HAC 27 0.5% TSP-C18 Epoxide-15PO-20EO-SO4, 0.5% C11-ABS, 1% Na2CO3, Brine Scan with Oil #1 (50% Oil scan) | | | | |
|---|---|---|---|---|---|---|
| Hydrocarbon | Oil #1 | Hydrocarbon Density | 1 | g/cc | Typical hydrocarbon Densities: | |
| Surfactant | TSP-C18 Epoxide-15PO-20EO-SO4 | Total Surfactant Conc. | 0 | wt % | Octane | |
| Co-Surfactant(1) | C11-ABS | Total Alcohol Conc. | 0 | wt % | Decane | |
| Co-Solvent | | Polymer Conc. | 0 | wt % | Mixed: Mar. 22, 2011 | |
| Surfactant Conc. | 0.5 wt % | Na2CO3 Conc. | 1 | wt % | | |
| Co-surf(1) Conc. | 0.5 wt % | WOR | 1 | | | |
| t-pent Conc. | | Temperature | 100 | Celcius | | |
| alkali | varied | Tube Size | 5 | mL | | |
| NaCl:CaCl Ratio | | | | | | |

| Salinity (% of SUTIB) | TDS in ppm (from SSUTIB) | Aqueous Level | Hydrocarbon Level | Top of emulsion | Top Interface | Bottom Interface | Bottom of emulsion | Type | Volume of Oil Solublized (cc) | Volume of Water Solublized (cc) | Oil Sol. Ratio (cc/cc) | Water Sol. Ratio (cc/cc) | HC Sol. (mg/L) | Volume Fraction of Oil (Vo) | Volume Fraction of Microemulsion (Vme) | Volume Fraction of Water (Vw) | Vw + Vme |
|---|---|---|---|---|---|---|---|---|---|---|---|---|---|---|---|---|---|
| | | Mar. 31, 2011 | | | | | | | | 9 days | | | | | | | |
| 0.00% | 10000 | 2.95 | 0.9 | 2.93 | | | | I | 0.02 | | 1.0 | | 0 | 0.495 | 0.505 | 0.000 | 0.505 |
| 10.00% | 16000 | 2.94 | 0.9 | 2.90 | | | | I | 0.04 | | 1.9 | | 0 | 0.488 | 0.512 | 0.000 | 0.512 |
| 20.00% | 22000 | 2.93 | 0.9 | 2.90 | | | | I | 0.03 | | 1.4 | | 0 | 0.488 | 0.512 | 0.000 | 0.512 |
| 30.00% | 28000 | 2.91 | 0.9 | 2.88 | | | | I | 0.03 | | 1.4 | | 0 | 0.483 | 0.517 | 0.000 | 0.517 |
| 40.00% | 34000 | 2.93 | 0.9 | 2.85 | | | | I | 0.08 | | 3.9 | | 0 | 0.476 | 0.524 | 0.000 | 0.524 |
| 50.00% | 40000 | 2.92 | 0.9 | 2.80 | | | | I | 0.12 | | 5.8 | | 0 | 0.463 | 0.537 | 0.000 | 0.537 |
| 60.00% | 46000 | 2.93 | 0.9 | 2.78 | | | | I | 0.15 | | 7.2 | | 0 | 0.459 | 0.541 | 0.000 | 0.541 |
| 70.00% | 52000 | 2.93 | 0.9 | 2.72 | | 3.30 | | III | 0.21 | 0.37 | 10.1 | 17.9 | 0 | 0.444 | 0.141 | 0.415 | 0.556 |
| 80.00% | 58000 | 2.96 | 0.9 | 2.00 | | 3.25 | | III | 0.96 | 0.29 | 47.1 | 14.2 | 0 | 0.268 | 0.305 | 0.427 | 0.732 |
| 90.00% | 64000 | 2.90 | 0.9 | | | 3.00 | | II | 2.90 | 0.10 | | 4.8 | 0 | 0 | 0.512 | 0.488 | 1.000 |
| 100.00% | 70000 | 2.92 | 0.9 | | | 3.00 | | II | 2.92 | 0.08 | | 3.8 | NA | 0 | 0.512 | 0.488 | 1.000 |
| 110.00% | 76000 | 2.91 | 0.9 | | | 2.98 | | II | 2.91 | 0.07 | | 3.3 | NA | 0 | 0.507 | 0.493 | 1.000 |
| 120.00% | 82000 | 2.93 | 0.9 | | | 2.98 | | II | 2.93 | 0.05 | | 2.4 | NA | 0 | 0.507 | 0.493 | 1.000 |
| 130.00% | 88000 | 2.95 | 0.9 | | | 3.00 | | II | 2.95 | 0.05 | | 2.4 | NA | 0 | 0.512 | 0.488 | 1.000 |
| | | Mar. 23, 2011 | | | | | | | | 1 days | | | | | | | |
| 0.00% | 10000 | 2.95 | 0.9 | 2.90 | | | | I | 0.05 | | 2.4 | | 0 | 0.488 | 0.512 | 0.000 | 0.512 |
| 10.00% | 16000 | 2.94 | 0.9 | 2.85 | | | | I | 0.09 | | 4.4 | | 0 | 0.476 | 0.524 | 0.000 | 0.524 |
| 20.00% | 22000 | 2.93 | 0.9 | 2.80 | | | | I | 0.13 | | 6.3 | | 0 | 0.463 | 0.537 | 0.000 | 0.537 |
| 30.00% | 28000 | 2.91 | 0.9 | 2.70 | | | | I | 0.21 | | 10.0 | | 0 | 0.439 | 0.561 | 0.000 | 0.561 |
| 40.00% | 34000 | 2.93 | 0.9 | 2.65 | | | | I | 0.28 | | 13.5 | | 0 | 0.427 | 0.573 | 0.000 | 0.573 |
| 50.00% | 40000 | 2.92 | 0.9 | 2.60 | | | | I | 0.32 | | 15.4 | | 0 | 0.415 | 0.585 | 0.000 | 0.585 |
| 60.00% | 46000 | 2.93 | 0.9 | 2.60 | | | | I | 0.33 | | 15.9 | | 0 | 0.415 | 0.585 | 0.000 | 0.585 |
| 70.00% | 52000 | 2.93 | 0.9 | 2.50 | | | | I | 0.43 | | 20.8 | | 0 | 0.390 | 0.610 | 0.000 | 0.610 |
| 80.00% | 58000 | 2.96 | 0.9 | | | 4.50 | | II | 2.96 | 1.54 | | 75.5 | NA | 0 | 0.878 | 0.122 | 1.000 |
| 90.00% | 64000 | 2.90 | 0.9 | | | 4.40 | | II | 2.90 | 1.50 | | 71.4 | NA | 0 | 0.854 | 0.146 | 1.000 |
| 100.00% | 70000 | 2.92 | 0.9 | | | 4.35 | | II | 2.92 | 1.43 | | 68.8 | NA | 0 | 0.841 | 0.159 | 1.000 |
| 110.00% | 76000 | 2.91 | 0.9 | | | 4.30 | | II | 2.91 | 1.39 | | 66.5 | NA | 0 | 0.829 | 0.171 | 1.000 |
| 120.00% | 82000 | 2.93 | 0.9 | | | 4.20 | | II | 2.93 | 1.27 | | 61.4 | NA | 0 | 0.805 | 0.195 | 1.000 |
| 130.00% | 88000 | 2.95 | 0.9 | | | 4.10 | | II | 2.95 | 1.15 | | 56.1 | NA | 0 | 0.780 | 0.220 | 1.000 |

TABLE 12

Figure 12:
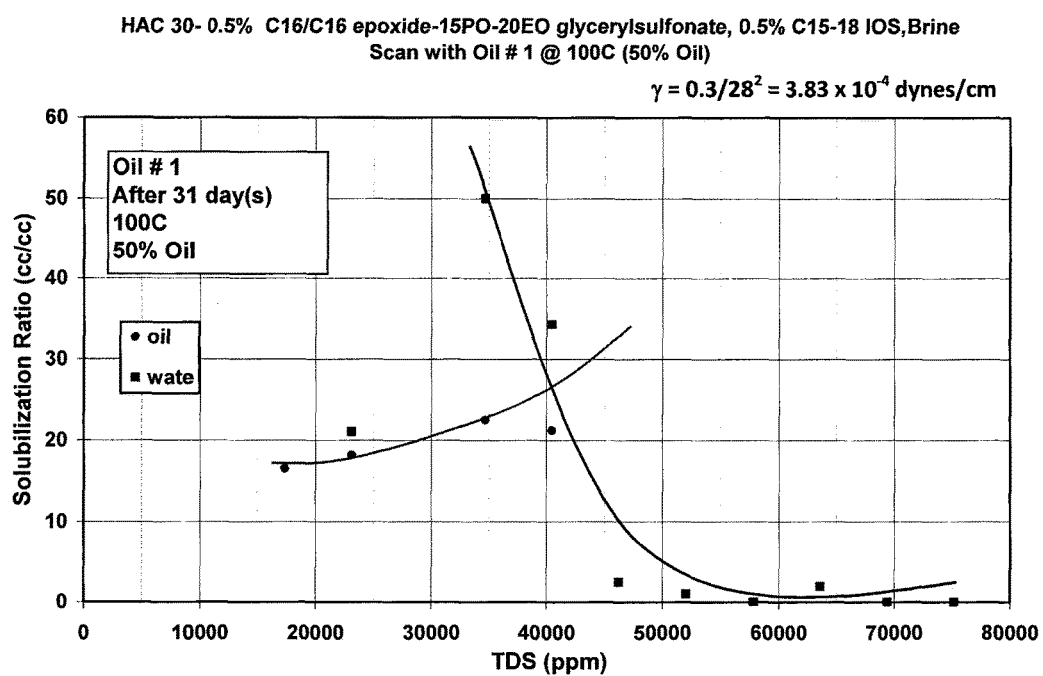
FIG. 12. Phase behavior plot for a study with HAC-30 0.5% C16 alcohol/C16 epoxide-15PO-20EO glycerylsulfonate, 0.5% C15-18 IOS, Brine Scan with Oil #1 at 100° C. (50% Oil).
Figure 13:
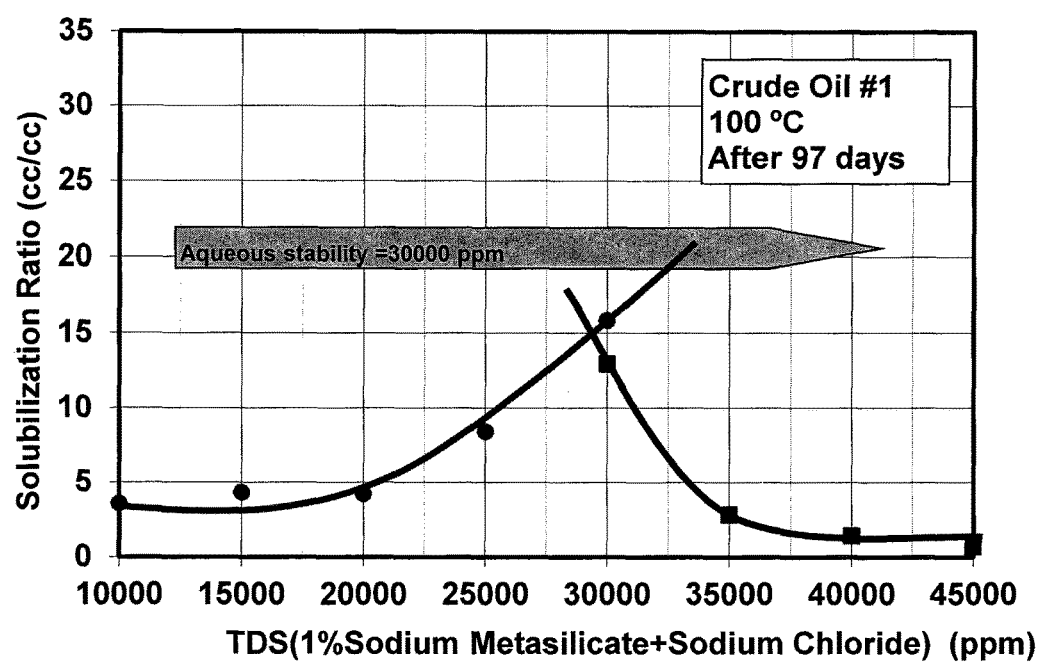
FIG. 13. Phase behavior plot for a study with 0.25% C16 alcohol/C16 epoxide-15PO-10EO carboxylate, 0.25% C20-24 IOS, 0.5% IBA-3EO Brine Scan with Oil #1 at 100° C. (30% Oil).

Phase behavior data recording sheet for the study described in FIG. 12.

| | | | | | |
|---|---|---|---|---|---|
| Experiment | HAC 30-0.5% C16/C16 epoxide-15PO-20EO glycerylsulfonate, 0.5% C15-18 IOS, Brine Scan with Oil # 1 @ 100 C. (50% Oil) | | | | |
| Hydrocarbon | Oil # 1 | Hydrocarbon Density | | g/cc | Typical hydrocarbon Densities: |
| Surfactant | C32-15PO-20EO Glyceryl sulfonate | Total Surfactant Conc. | 1 | wt % | Octane |
| | | Total Alcohol Conc. | | wt % | Decane |
| Co-Surfactant(1) | C15-18 IOS | Polymer Conc. | 0 | wt % | Mixed: Mar. 7, 2011 |
| Co-Solvent | | Na2CO3 Conc. | 0 | wt % | |
| Surfactant Conc. | 0.5 wt % | WOR | 1 | | |
| Co-surf(1) Conc. | 0.5 wt % | Temperature | 100 | Celcius | |
| t-pent Conc. | wt % | Tube Size | 5 | mL | |
| Neodol 25-12 | wt % | | | | |
| NaCl:CaCl Ratio | | | | | |

| Salinity (% of SUTIB) | TDS in ppm | Aqueous Level | Hydrocarbon Level | Top of emulsion | Top Interface | Bottom Interface | Bottom of emulsion | Type | Volume of Oil Solublized (cc) | Volume of Water Solublized (cc) |
|---|---|---|---|---|---|---|---|---|---|---|
| | | Apr. 7, 2011 | | | | | 31 days | | | |
| 30.00% | 17345 | 2.94 | 0.9 | | 2.60 | | | I | 0.34 | |
| 40.00% | 23127 | 2.91 | 0.9 | | 2.53 | 3.35 | | III | 0.38 | 0.44 |
| 50.00% | 28909 | 3.00 | 0.9 | | | | | I | 3.00 | |
| 60.00% | 34690 | 3.00 | 0.9 | | 2.55 | 4.00 | | III | 0.45 | 1.00 |
| 70.00% | 40472 | 3.02 | 0.9 | | 2.60 | 3.70 | | III | 0.42 | 0.68 |
| 80.00% | 46254 | 3.00 | 0.9 | | | 3.05 | | II | 3.00 | 0.05 |
| 90.00% | 52035 | 3.00 | 0.9 | | | 3.02 | | II | 3.00 | 0.02 |
| 100.00% | 57817 | 3.05 | 0.9 | | | 3.05 | | II | 3.05 | 0.00 |
| 110.00% | 63599 | 2.95 | 0.9 | | | 2.99 | | II | 2.95 | 0.04 |
| 120.00% | 69380 | 3.00 | 0.9 | | | | | I | 3.00 | |
| 130.00% | 75162 | 3.07 | 0.9 | | | | | I | 3.07 | |

| Salinity (% of SUTIB) | TDS in ppm | Aqueous Level | Oil Sol. Ratio (cc/cc) | Water Sol. Ratio (cc/cc) | HC Sol. (mg/L) | Volume Fraction of Oil (Vo) | Volume Fraction of Microemulsion (Vme) | Fraction of Water (Vw) | Vw + Vme |
|---|---|---|---|---|---|---|---|---|---|
| | | Apr. 7, 2011 | | | | 31 days | | | |
| 30.00% | 17345 | 2.94 | 16.5 | | 0 | 0.415 | 0.200 | 0.385 | 0.585 |
| 40.00% | 23127 | 2.91 | 18.2 | | 0 | 0.398 | 0.200 | 0.402 | 0.602 |
| 50.00% | 28909 | 3.00 | | | 0 | −0.220 | 0.354 | 0.866 | 1.220 |
| 60.00% | 34690 | 3.00 | 22.5 | 50.0 | 0 | 0.402 | 0.354 | 0.244 | 0.598 |
| 70.00% | 40472 | 3.02 | 21.2 | 34.3 | 0 | 0.415 | 0.268 | 0.317 | 0.585 |
| 80.00% | 46254 | 3.00 | | 2.5 | NA | 0 | 0.524 | 0.476 | 1.000 |
| 90.00% | 52035 | 3.00 | | 1.0 | NA | 0 | 0.517 | 0.483 | 1.000 |
| 100.00% | 57817 | 3.05 | | 0.0 | NA | 0 | 0.524 | 0.476 | 1.000 |
| 110.00% | 63599 | 2.95 | | 2.0 | NA | 0 | 0.510 | 0.490 | 1.000 |
| 120.00% | 69380 | 3.00 | | | 0 | −0.220 | 1.220 | 0.000 | 1.220 |
| 130.00% | 75162 | 3.07 | | | 0 | −0.220 | 1.220 | 0.000 | 1.220 |

TABLE 13

IFT values for the different surfactant compositions provided herein.

| Surfactant System | FIG. | Solubilization Ratio (cc/cc) | IFT ($\gamma$) using Chun-Huh's relation (dynes/cm) |
|---|---|---|---|
| HAC-20 0.5% Isofol-C32-15PO-10EO-SO4, 0.5% C11-ABS, 1% Na$_2$CO$_3$, Brine Scan with Oil #1 (50%) at 100° C. | 1 | 40 | $1.87 \times 10^{-4}$ |
| HAC-07 0.25% Isofol C32-15PO-10EO SO4, 0.25% 20-24 IOS, 0.5% Na$_2$CO$_3$, NaCl Scan at 45° C. | 2 | 12.3 | $19.8 \times 10^{-4}$ |
| HAC-21 0.5% C16/C16 Epoxide-15PO-10EO-SO4, 0.5% C11-ABS, 1% Na$_2$CO3, Brine Scan with Oil #1(50% Oil) at 100° C. | 3 | 40 | $1.87 \times 10^{-4}$ |
| HAC-06 0.25% C16/C16 epoxide-15PO-10EO SO4, 0.25% C20-24 IOS, 0.5% Na$_2$CO$_3$, NaCl Scan at 45° C.; | 4 | 11 | $24.8 \times 10^{-4}$ |
| HAC-22 0.5% C16-7PO-C16-Epoxide-8PO-10EO-SO4, 0.5% C11-ABS, 1% Na$_2$CO$_3$, Brine Scan with Oil #1 (50% Oil) at 100° C. | 5 | 40 | $1.87 \times 10^{-4}$ |
| HAC-10 0.25% C16-7PO-C16 Epoxide-8PO-10EO Sulfate, 0.25% (C20-24 IOS), 0.5% Na$_2$CO$_3$, NaCl Scan at 45° C.; | 6 | 12.5 | $19.2 \times 10^{-4}$ |
| HAC-23 0.5% C16-15PO-C16 Epoxide-10EO-SO4, 0.5% C11-ABS, 1% Na$_2$CO$_3$, Brine Scan with Oil # 1 (50% Oil) at 100° C. | 7 | 40 | $1.87 \times 10^{-4}$ |
| HAC-24 0.5% C16/16 Epoxide-15BO-15PO-30EO-SO4, 0.5% C11-ABS, 1% Na$_2$CO$_3$, Brine Scan with Oil #1 (50% Oil) at 100° C. | 8 | 40 | $1.87 \times 10^{-4}$ |

TABLE 13-continued

IFT values for the different surfactant compositions provided herein.

| Surfactant System | FIG. | Solubilization Ratio (cc/cc) | IFT ($\gamma$) using Chun-Huh's relation (dynes/cm) |
|---|---|---|---|
| HAC-11 0.25% C16/16 Epoxide-15BO-15PO-30EO SO4, 0.25% C20-24 IOS, 0.5% Na$_2$CO$_3$, NaCl scan at 45° C. | 9 | 15 | $13.3 \times 10^{-4}$ |
| HAC-25 0.5% Isofol C32-C18 Epoxide-15PO-40EO-SO4, 0.5% C11-ABS, 1% Na$_2$CO$_3$, Brine Scan with Oil #1 (50% Oil) at 100° C. | 10 | 11 | $24.8 \times 10^{-4}$ |
| HAC-27 0.5% TSP/C18 Epoxide-15PO-20EO-SO4, 0.5% C11-ABS, 1% Na$_2$CO$_3$, Brine Scan with Oil #1 at 100° C. | 11 | 15 | $13.3 \times 10^{-4}$ |
| HAC-30 0.5% C16/C16 epoxide-15PO-20EO glyceryl sulfonate, 0.5% C15-18 IOS, Brine Scan with Oil # 1 at 100° C. (50% Oil) | 12 | 28 | $3.83 \times 10^{-4}$ |
| 0.25% C16C16-Epoxide-15PO-10EO-Carboxylate, 0.25% 20-24-IOS, 0.5% IBA-3EO | 13 | 15 | |

VII. Embodiments

Embodiment 1. A compound having the formula:

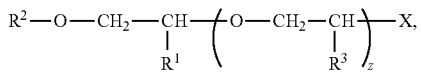

wherein, $R^1$ is $R^{10}$-substituted or unsubstituted $C_8$-$C_{50}$ alkyl, $R^4$-substituted or unsubstituted heteroalkyl, $R^4$-substituted or unsubstituted aryl or $R^4$-substituted or unsubstituted cycloalkyl; $R^4$ is $R^5$-substituted or unsubstituted $C_1$-$C_{50}$ alkyl, $R^5$-substituted or unsubstituted heteroalkyl, $R^5$-substituted or unsubstituted aryl or $R^5$-substituted or unsubstituted cycloalkyl; $R^5$ is $R^6$-substituted or unsubstituted $C_1$-$C_{50}$ alkyl, $R^6$-substituted or unsubstituted heteroalkyl, $R^6$-substituted or unsubstituted aryl or $R^6$-substituted or unsubstituted cycloalkyl; $R^6$ is $R^7$-substituted or unsubstituted $C_1$-$C_{50}$ alkyl, $R^7$-substituted or unsubstituted heteroalkyl, $R^7$-substituted or unsubstituted aryl or $R^7$-substituted or unsubstituted cycloalkyl; $R^7$ is $R^8$-substituted or unsubstituted $C_1$-$C_{50}$ alkyl, $R^8$-substituted or unsubstituted heteroalkyl, $R^8$-substituted or unsubstituted aryl or $R^8$-substituted or unsubstituted cycloalkyl; $R^8$ is $R^9$-substituted or unsubstituted $C_1$-$C_{50}$ alkyl, $R^9$-substituted or unsubstituted heteroalkyl, $R^9$-substituted or unsubstituted aryl or $R^9$-substituted or unsubstituted cycloalkyl; $R^9$ is unsubstituted $C_1$-$C_{50}$ alkyl, unsubstituted heteroalkyl, unsubstituted aryl or unsubstituted cycloalkyl; $R^{10}$ is unsubstituted hetreroalkyl, unsubstituted aryl or unsubstituted cycloalkyl; $R^2$ is $R^{10a}$-substituted or unsubstituted $C_8$-$C_{50}$ alkyl, $R^{4a}$-substituted or unsubstituted heteroalkyl, $R^{4a}$-substituted or unsubstituted aryl or $R^{4a}$-substituted or unsubstituted cycloalkyl; $R^{4a}$ is $R^{5a}$-substituted or unsubstituted $C_1$-$C_{50}$ alkyl, $R^{5a}$-substituted or unsubstituted heteroalkyl, $R^{5a}$-substituted or unsubstituted aryl or $R^{5a}$-substituted or unsubstituted cycloalkyl; $R^{5a}$ is $R^{6a}$-substituted or unsubstituted $C_1$-$C_{50}$ alkyl, $R^{6a}$-substituted or unsubstituted heteroalkyl, $R^{6a}$-substituted or unsubstituted aryl or $R^{6a}$-substituted or unsubstituted cycloalkyl; $R^{6a}$ is $R^{7a}$-substituted or unsubstituted $C_1$-$C_{50}$ alkyl, $R^{7a}$-substituted or unsubstituted heteroalkyl, $R^{7a}$-substituted or unsubstituted aryl or $R^{7a}$-substituted or unsubstituted cycloalkyl; $R^{7a}$ is $R^{8a}$-substituted or unsubstituted $C_1$-$C_{50}$ alkyl, $R^{8a}$-substituted or unsubstituted heteroalkyl, $R^{8a}$-substituted or unsubstituted aryl or $R^{5a}$-substituted or unsubstituted cycloalkyl; $R^{8a}$ is $R^{9a}$-substituted or unsubstituted $C_1$-$C_{50}$ alkyl, $R^{9a}$-substituted or unsubstituted heteroalkyl, $R^{9a}$-substituted or unsubstituted aryl or $R^{9a}$-substituted or unsubstituted cycloalkyl; $R^{9a}$ is unsubstituted $C_1$-$C_{50}$ alkyl, unsubstituted heteroalkyl, unsubstituted aryl or unsubstituted cycloalkyl; $R^{10a}$ is unsubstituted heteroalkyl, unsubstituted aryl or unsubstituted cycloalkyl; $R^3$ is independently hydrogen or unsubstituted $C_1$-$C_6$ alkyl; z is an integer from 2 to 100; X is

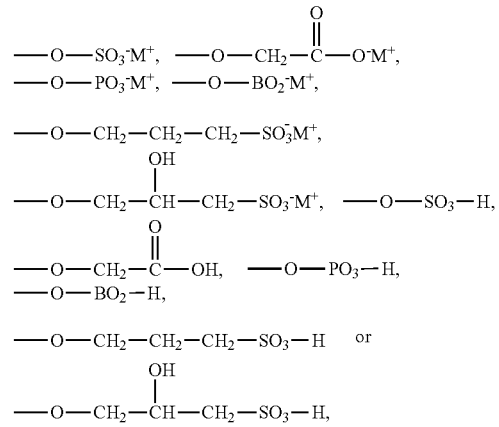

and $M^+$ is a monovalent, divalent or trivalent cation.

Embodiment 2. The compound of embodiment 1, wherein $R^1$ is branched or linear unsubstituted $C_8$-$C_{50}$ alkyl.

Embodiment 3. The compound of embodiment 1, wherein $R^1$ is branched or linear unsubstituted $C_{10}$-$C_{50}$ alkyl.

Embodiment 4. The compound of embodiment 1, wherein $R^1$ is branched unsubstituted $C_{10}$-$C_{50}$ alkyl.

Embodiment 5. The compound of embodiment 1, wherein $R^1$ is branched unsubstituted $C_{12}$-$C_{50}$ alkyl.

Embodiment 6. The compound of embodiment 1, wherein $R^1$ is branched unsubstituted $C_{14}$-$C_{30}$ alkyl.

Embodiment 7. The compound of embodiment 1, wherein $R^2$ is branched or linear unsubstituted $C_{10}$-$C_{50}$ alkyl, $R^{4a}$-substituted $C_{10}$-$C_{50}$ heteroalkyl, or $R^{4a}$-substituted phenyl.

Embodiment 8. The compound of embodiment 1, wherein $R^2$ is branched or linear unsubstituted $C_{14}$-$C_{50}$ alkyl, $R^{4a}$-substituted $C_{20}$-$C_{50}$ heteroalkyl, $(C_6H_5-CH_2CH_2)_3C_6H_2-$, $(C_6H_5-CH_2CH_2)_2C_6H_3-$, $(C_6H_5-CH_2CH_2)_1C_6H_4-$, or $R^{4a}$-substituted or unsubstituted naphthyl.

Embodiment 9. The compound of embodiment 1, wherein $R^2$ is branched unsubstituted $C_{20}$-$C_{50}$ alkyl or linear unsubstituted $C_{16}$-$C_{40}$ alkyl.

Embodiment 10. The compound of embodiment 1, wherein $R^2$ is branched $R^{4a}$-substituted $C_{30}$-$C_{50}$ heteroalkyl.

Embodiment 11. The compound of embodiment 1, wherein $R^2$ is branched $R^{4a}$-substituted $C_{14}$-$C_{50}$ heteroalkyl.

Embodiment 12. The compound of embodiment 1, wherein $R^3$ is independently hydrogen or unsubstituted $C_1$-$C_2$ alkyl.

Embodiment 13. The compound of embodiment 1, wherein z is 5 to 150.

Embodiment 14. The compound of embodiment 1, wherein z is 10 to 100.

Embodiment 15. The compound of embodiment 1, wherein $M^+$ is $Na^+$, $K^+$, $NH_4^+$, $Ca^{+2}$, $Mg^{+2}$ or $Ba^{+2}$.

Embodiment 16. The compound of embodiment 1 having the formula:

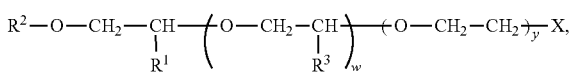

wherein $R^3$ is independently unsubstituted $C_1$-$C_4$ alkyl; y is an integer from 1 to 50; and w is an integer from 0 to 60.

Embodiment 17. The compound of embodiment 16, wherein $R^2$ is unsubstituted tristyrylphenyl.

Embodiment 18. The compound of embodiment 16, wherein $R^3$ is independently methyl or ethyl.

Embodiment 19. The compound of embodiment 1 having the formula:

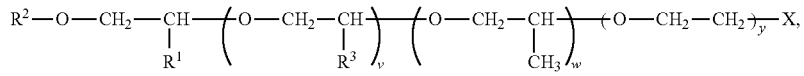

wherein $R^3$ is ethyl; y is an integer from 1 to 30; w is an integer from 0 to 30; and v is an integer from 0 to 30.

Embodiment 20. The compound of embodiment 1 having the formula:

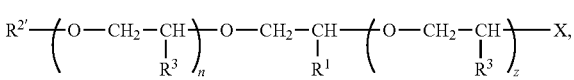

wherein $R^{2'}$ is linear unsubstituted $C_{10}$-$C_{60}$ alkyl; R is independently hydrogen or unsubstituted $C_1$-$C_4$ alkyl; n is an integer from 0 to 50; and z is an integer from 5 to 25.

Embodiment 21. The compound of embodiment 20, wherein $R^3$ is independently hydrogen or methyl.

Embodiment 22. The compound of embodiment 1 having the formula:

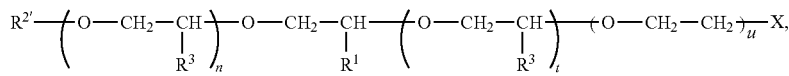

wherein $R^3$ is independently methyl or ethyl; n is an integer from 0 to 50; t is an integer from 0 to 30; and u is an integer from 5 to 30.

Embodiment 23. An aqueous composition comprising a co-surfactant and the compound of one of embodiments 1 to 22.

Embodiment 24. The aqueous composition of embodiment 23, wherein said co-surfactant is an anionic surfactant, a non-ionic surfactant, or a cationic surfactant.

Embodiment 25. The aqueous composition of embodiment 23, wherein said co-surfactant is an internal olefin sulfonate (IOS), an alfa olefin sulfonate (AOS), an alkyl aryl sulfonate (ARS), an alkane sulfonate, a petroleum sulfonate, an alkyl diphenyl oxide (di)sulfonate, an alcohol sulfate, an alkoxy sulfate, an alkoxy sulfonate, an alcohol phosphate, an alkoxy phosphate, a sulfosuccinate ester, an alcohol ethoxylate, an alkyl phenol ethoxylate, a quaternary ammonium salt, a betaine or sultaine.

Embodiment 26. The aqueous composition of embodiment 23, wherein said co-surfactant is a $C_{10}$-$C_{30}$ internal olefin sulfate (IOS) or a $C_8$-$C_{30}$ alkyl benzene sulfonate (ABS).

Embodiment 27. The aqueous composition of embodiment 23, further comprising an alkali agent.

Embodiment 28. The aqueous composition of embodiment 27, wherein said alkali agent is NaOH, KOH, LiOH, $Na_2CO_3$, $NaHCO_3$, Na-metaborate, Na silicate, Na orthosilicate, or $NH_4OH$.

Embodiment 29. The aqueous composition of embodiment 23, further comprising a viscosity enhancing water-soluble polymer.

Embodiment 30. The aqueous composition of embodiment 23, further comprising a co-solvent.

Embodiment 31. The aqueous composition of embodiment 23, further comprising a gas.

Embodiment 32. The aqueous composition of embodiment 23, wherein said compound is present in an amount sufficient to increase the solubility of said co-surfactant in said aqueous composition relative to the absence of said compound.

Embodiment 33. The aqueous composition of embodiment 23, wherein said co-surfactant is present in an amount sufficient to increase the solubility of said compound in said aqueous composition relative to the absence of said co-surfactant.

Embodiment 34. The aqueous composition of embodiment 23 having a pH of less than 13.

Embodiment 35. The aqueous composition of embodiment 23 having a pH of less than 10.

Embodiment 36. The aqueous composition of embodiment 23 having a pH of less than 8.

Embodiment 37. The aqueous composition of embodiment 23 having a salinity of at least 10,000 ppm.

Embodiment 38. The aqueous composition of embodiment 23 having a salinity of at least 50,000 ppm.

Embodiment 39. The aqueous composition of embodiment 23 having a salinity of at least 100,000 ppm.

Embodiment 40. The aqueous composition of embodiment 23, wherein the temperature of said aqueous composition is at least 40° C.

Embodiment 41. The aqueous composition of embodiment 23, wherein the temperature of said aqueous composition is at least 100° C.

Embodiment 42. An emulsion composition comprising an unrefined petroleum phase and an aqueous, wherein said aqueous phase comprises the compound of one of embodiments 1 to 22.

Embodiment 43. The emulsion composition of embodiment 42, further comprising a co-surfactant.

Embodiment 44. The emulsion composition of embodiment 42, wherein the emulsion composition is a microemulsion.

Embodiment 45. The biphasic composition of embodiment 42, wherein the oil and water solubilization ratios of the aqueous phase are insensitive to the combined concentration of $Ca^{+2}$ and $Mg^{+2}$ combined within in the aqueous phase.

Embodiment 46. The biphasic composition of embodiment 42, wherein the oil and water solubilization ratios of the aqueous phase are insensitive to the salinity of the water within the aqueous phase.

Embodiment 47. A method of displacing a hydrocarbon material in contact with a solid material, said method comprising: (i) contacting a hydrocarbon material with the compound of one of embodiments 1 to 22, wherein said hydrocarbon material is in contact with a solid material; (ii) allowing said hydrocarbon material to separate from said solid material thereby displacing said hydrocarbon material in contact with said solid material.

Embodiment 48. The method of embodiment 47, further comprising contacting the solid material with the compound.

Embodiment 49. The method of embodiment 47, wherein said hydrocarbon material is unrefined petroleum in a petroleum reservoir and said solid material is a natural solid material in a petroleum reservoir.

Embodiment 50. The method of embodiment 49, wherein said method is an enhanced oil recovery method.

Embodiment 51. The method of embodiment 47, wherein said natural solid material is rock or regolith.

Embodiment 52. The method of embodiment 51, wherein said regolith is soil.

Embodiment 53. The method of embodiment 47, wherein said compound forms part of an aqueous composition comprising a co-surfactant and said hydrocarbon material is an unrefined petroleum material.

Embodiment 54. The method of embodiment 53, wherein an emulsion forms after said contacting.

Embodiment 55. The method of embodiment 54, wherein said method further comprises allowing an unrefined petroleum acid within said unrefined petroleum material to enter into said emulsion, thereby converting said unrefined petroleum acid into a surfactant.

Embodiment 56. The method of embodiment 53, wherein said co-surfactant is an internal olefin sulfonate (IOS), an alfa olefin sulfonate (AOS), an alkyl aryl sulfonate (ARS), an alkane sulfonate, a petroleum sulfonate, an alkyl diphenyl ether (di)sulfonate, an alcohol sulfate, an alkoxy sulfate, an alcohol phosphate, an alkoxy phosphate, a sulfosuccinate ester, an alcohol ethoxylate, an alkyl phenol ethoxylate or a quaternary ammonium salt.

Embodiment 57. The method of embodiment 53, wherein said co-surfactant is a $C_{10}$-$C_{30}$ internal olefin sulfate or a $C_8$-$C_{30}$ alkyl benzene sulfonate.

Embodiment 58. The method of embodiment 53, wherein said aqueous composition further comprises a viscosity enhancing polymer.

Embodiment 59. A method of converting an unrefined petroleum acid into a surfactant, said method comprising: (i) contacting a petroleum material with an aqueous composition thereby forming an emulsion in contact with said petroleum material, wherein said aqueous composition comprises the compound of one of embodiments 1 to 22 and a co-surfactant; (ii) allowing an unrefined petroleum acid within said unrefined petroleum material to enter into said emulsion, thereby converting said unrefined petroleum acid into a surfactant.

Embodiment 60. The method of embodiment 59, wherein said reactive petroleum material is in a petroleum reservoir.

Embodiment 61. A method of making a compound of one of embodiments 1 to 22, the method comprising: contacting an epoxide compound with an alcohol thereby forming an epoxide-alcohol mixture; increasing the temperature of said epoxide-alcohol mixture thereby forming an epoxide-alcohol adduct; contacting said epoxide-alcohol adduct with a $C_1$-$C_4$ alkoxide thereby forming a alkoxylated hydrophobe; and contacting said alkoxylated hydrophobe with one or more anionic functional groups thereby forming said compound.

What is claimed is:
1. A compound having the formula:

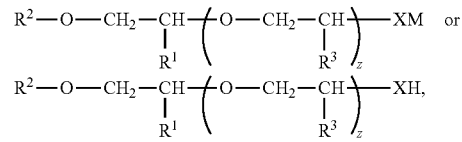

wherein
$R^1$ is branched unsubstituted $C_{14}$-$C_{30}$ alkyl;
$R^2$ is $R^{10a}$-substituted or unsubstituted $C_8$-$C_{50}$ alkyl, $R^{4a}$-substituted or unsubstituted heteroalkyl, $R^{4a}$-substituted or unsubstituted aryl or $R^{4a}$-substituted or unsubstituted cycloalkyl;
$R^{4a}$ is $R^{5a}$-substituted or unsubstituted $C_1$-$C_{50}$ alkyl, $R^{5a}$-substituted or unsubstituted heteroalkyl, $R^{5a}$-substituted or unsubstituted aryl or $R^{5a}$-substituted or unsubstituted cycloalkyl;
$R^{5a}$ is $R^{6a}$-substituted or unsubstituted $C_1$-$C_{50}$ alkyl, $R^{6a}$-substituted or unsubstituted heteroalkyl, $R^{6a}$-substituted or unsubstituted aryl or $R^{6a}$-substituted or unsubstituted cycloalkyl;
$R^{6a}$ is $R^{7a}$-substituted or unsubstituted $C_1$-$C_{50}$ alkyl, $R^{7a}$-substituted or unsubstituted heteroalkyl, $R^{7a}$-substituted or unsubstituted aryl or $R^{7a}$-substituted or unsubstituted cycloalkyl;
$R^{7a}$ is $R^{8a}$-substituted or unsubstituted $C_1$-$C_{50}$ alkyl, $R^{8a}$-substituted or unsubstituted heteroalkyl, $R^{8a}$-substituted or unsubstituted heteroalkyl, $R^{8a}$-substituted or unsubstituted aryl or $R^{8a}$-substituted or unsubstituted cycloalkyl;
$R^{8a}$ is $R^{9a}$-substituted or unsubstituted $C_1$-$C_{50}$ alkyl, $R^{9a}$-substituted or unsubstituted heteroalkyl, $R^{9a}$-substituted or unsubstituted aryl or $R^{9a}$-substituted or unsubstituted cycloalkyl;
$R^{9a}$ is unsubstituted $C_1$-$C_{50}$ alkyl, unsubstituted heteroalkyl, unsubstituted aryl or unsubstituted cycloalkyl;

$R^{10a}$ is unsubstituted heteroalkyl, unsubstituted aryl or unsubstituted cycloalkyl;

$R^3$ is independently hydrogen or unsubstituted $C_1$-$C_6$ alkyl;

z is an integer from 2 to 100;

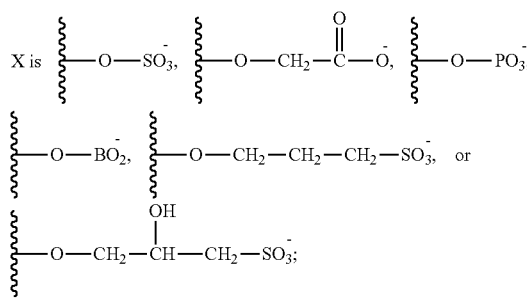

and

M is a monovalent, divalent or trivalent cation.

2. The compound of claim 1, wherein $R^1$ is branched or linear unsubstituted $C_8$-$C_{50}$ alkyl.

3. The compound of claim 1, wherein $R^1$ is branched unsubstituted $C_{10}$-$C_{50}$ alkyl.

4. The compound of claim 1, wherein $R^2$ is branched or linear unsubstituted $C_{10}$-$C_{50}$ alkyl, $R^{4a}$-substituted $C_{10}$-$C_{50}$ heteroalkyl, or $R^{4a}$-substituted phenyl.

5. The compound of claim 1, wherein $R^2$ is branched unsubstituted $C_{20}$-$C_{50}$ alkyl or linear unsubstituted $C_{16}$-$C_{40}$ alkyl.

6. The compound of claim 1, wherein $R^2$ is branched $R^{4a}$-substituted $C_{14}$-$C_{50}$ heteroalkyl.

7. The compound of claim 1, wherein $R^3$ is independently hydrogen or unsubstituted $C_1$-$C_2$ alkyl.

8. The compound of claim 1, wherein z is 10 to 100.

9. The compound of claim 1, wherein M is $Na^+$, $K^+$, $NH_4^+$, $Ca^{+2}$, $Mg^{+2}$ or $Ba^{+2}$.

10. The compound of claim 1 having the formula:

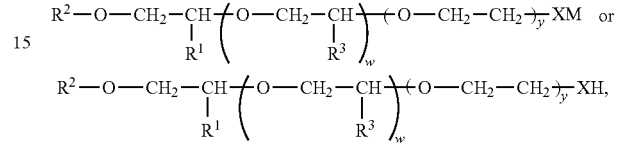

wherein $R^3$ is independently unsubstitued $C_1$-$C_4$ alkyl;

y is an integer from 1 to 50; and w is an integer from 0 to 60.

11. The compound of claim 10, wherein $R^2$ is unsubstituted tristyrylphenyl.

12. The compound of claim 10, wherein $R^3$ is independently methyl or ethyl.

13. The compound of claim 1 having the formula:

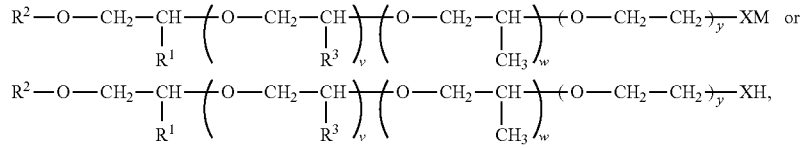

wherein $R^3$ is ethyl;

y is an integer from 1 to 30;

w is an integer from 0 to 30; and v is an integer from 0 to 30.

14. The compound of claim 1 having the formula:

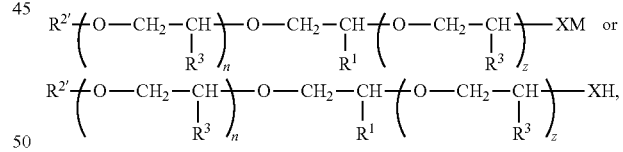

wherein $R^{2'}$ is linear unsubstituted $C_{10}$-$C_{60}$ alkyl;

$R^3$ is independently hydrogen or unsubstitued $C_1$-$C_4$ alkyl;

n is an integer from 0 to 50; and z is an integer from 5 to 25.

15. The compound of claim 1 having the formula:

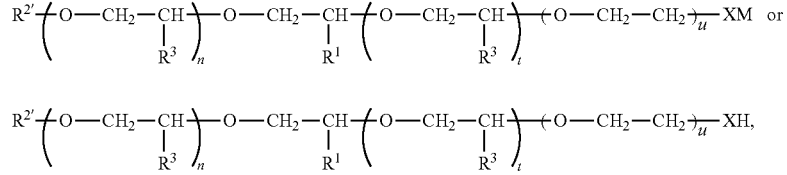

wherein

R³ is independently methyl or ethyl;
n is an integer from 0 to 50;
t is an integer from 0 to 30; and
u is an integer from 5 to 30.

16. An aqueous composition comprising a co-surfactant and the compound of claim 1.

17. The aqueous composition of claim 16, further comprising an alkali agent.

18. The aqueous composition of claim 16 having a pH of less than 13.

19. The aqueous composition of claim 16 having a pH of less than 8.

20. The aqueous composition of claim 16 having a salinity of at least 10,000 ppm.

21. The aqueous composition of claim 16, wherein the temperature of said aqueous composition is at least 40° C.

22. An emulsion composition comprising an unrefined petroleum phase and an aqueous, wherein said aqueous phase comprises the compound of claim 1.

23. The emulsion composition of claim 22, further comprising a co-surfactant.

24. The biphasic composition of claim 22, wherein the oil and water solubilization ratios of the aqueous phase are insensitive to the combined concentration of $Ca^{+2}$ and $Mg^{+2}$ combined within in the aqueous phase.

25. The biphasic composition of claim 22, wherein the oil and water solubilization ratios of the aqueous phase are insensitive to the salinity of the water within the aqueous phase.

26. A method of displacing a hydrocarbon material in contact with a solid material, said method comprising:
    (i) contacting a hydrocarbon material with the compound of claim 1, wherein said hydrocarbon material is in contact with a solid material;
    (ii) allowing said hydrocarbon material to separate from said solid material thereby displacing said hydrocarbon material in contact with said solid material.

27. The method of claim 26, further comprising contacting the solid material with the compound.

28. The method of claim 27, wherein said method is an enhanced oil recovery method.

29. A method of converting an unrefined petroleum acid into a surfactant, said method comprising:
    (i) contacting a petroleum material with an aqueous composition thereby forming an emulsion in contact with said petroleum material, wherein said aqueous composition comprises the compound of claim 1 and a co-surfactant;
    (ii) allowing an unrefined petroleum acid within said unrefined petroleum material to enter into said emulsion, thereby converting said unrefined petroleum acid into a surfactant.

30. A compound having the formula:

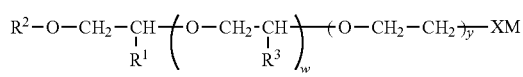

or

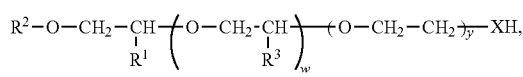

wherein $R^1$ is $R^{10}$-substituted or unsubstituted $C_8$-$C_{50}$ alkyl, $R^4$-substituted or unsubstituted heteroalkyl, $R^4$-substituted or unsubstituted aryl or $R^4$-substituted or unsubstituted cycloalkyl;

$R^4$ is $R^5$-substituted or unsubstituted $C_1$-$C_{50}$ alkyl, $R^5$-substituted or unsubstituted heteroalkyl, $R^5$-substituted or unsubstituted aryl or $R^5$-substituted or unsubstituted cycloalkyl;

$R^5$ is $R^6$-substituted or unsubstituted $C_1$-$C_{50}$ alkyl, $R^6$-substituted or unsubstituted heteroalkyl, $R^6$-substituted or unsubstituted aryl or $R^6$-substituted or unsubstituted cycloalkyl;

$R^6$ is $R^7$-substituted or unsubstituted $C_1$-$C_{50}$ alkyl, $R^7$-substituted or unsubstituted heteroalkyl, $R^7$-substituted or unsubstituted aryl or $R^7$-substituted or unsubstituted cycloalkyl;

$R^7$ is $R^8$-substituted or unsubstituted $C_1$-$C_{50}$ alkyl, $R^8$-substituted or unsubstituted heteroalkyl, $R^8$-substituted or unsubstituted heteroalkyl, $R^8$-substituted or unsubstituted aryl or $R^8$-substituted or unsubstituted cycloalkyl;

$R^8$ is $R^9$-substituted or unsubstituted $C_1$-$C_{50}$ alkyl, $R^9$-substituted or unsubstituted heteroalkyl, $R^9$-substituted or unsubstituted aryl or $R^9$-substituted or unsubstituted cycloalkyl;

$R^9$ is unsubstituted $C_1$-$C_{50}$ alkyl, unsubstituted heteroalkyl, unsubstituted aryl or unsubstituted cycloalkyl;

$R^{10}$ is unsubstituted hetreroalkyl, unsubstituted aryl or unsubstituted cycloalkyl;

$R^2$ is unsubstituted tristyrylphenyl;
$R^3$ is independently unsubstitued $C_1$-$C_4$ alkyl;
y is an integer from 1 to 50;
w is an integer from 0 to 60;

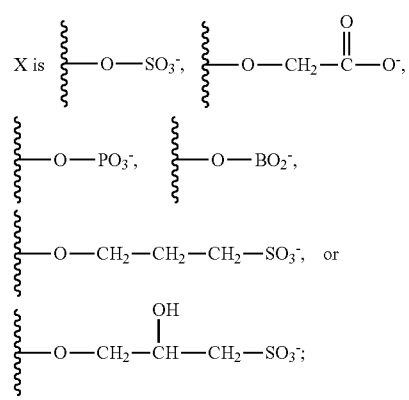

and

M is a monovalent, divalent or trivalent cation.

* * * * *